US011396538B2

(12) United States Patent
Rickles et al.

(10) Patent No.: US 11,396,538 B2
(45) Date of Patent: Jul. 26, 2022

(54) ANTIBODIES TO CENTRIN-1, METHODS OF MAKING, AND USES THEREOF

(71) Applicants: RadImmune Therapeutics, Inc., Tarrytown, NY (US); Albert Einstein College of Medicine, Bronx, NY (US)

(72) Inventors: David J. Rickles, Manhattan Beach, CA (US); Ekaterina Dadachova, Saskatoon (CA); Ruth A. Bryan, New Rochelle, NY (US)

(73) Assignees: RADIMMUNE THERAPEUTICS, INC., Tarrytown, NY (US); ALBERT EINSTEIN COLLEGE OF MEDICINE, Bronx, NY (US)

( * ) Notice: Subject to any disclaimer, the term of this patent is extended or adjusted under 35 U.S.C. 154(b) by 0 days.

(21) Appl. No.: 16/955,751

(22) PCT Filed: Dec. 20, 2018

(86) PCT No.: PCT/US2018/066971
§ 371 (c)(1),
(2) Date: Jun. 18, 2020

(87) PCT Pub. No.: WO2019/126594
PCT Pub. Date: Jun. 27, 2019

(65) Prior Publication Data
US 2020/0317766 A1 Oct. 8, 2020

Related U.S. Application Data

(60) Provisional application No. 62/753,665, filed on Oct. 31, 2018, provisional application No. 62/608,495, filed on Dec. 20, 2017.

(51) Int. Cl.
*A61K 51/10* (2006.01)
*C07K 16/18* (2006.01)
*A61K 39/00* (2006.01)

(52) U.S. Cl.
CPC .......... *C07K 16/18* (2013.01); *A61K 51/1018* (2013.01); *A61K 51/1096* (2013.01); *A61K 2039/505* (2013.01); *C07K 2317/33* (2013.01); *C07K 2317/34* (2013.01); *C07K 2317/565* (2013.01)

(58) Field of Classification Search
None
See application file for complete search history.

(56) References Cited

U.S. PATENT DOCUMENTS

| 6,103,481 A | 8/2000 | Schatten et al. |
| 8,519,104 B2 | 8/2013 | Alper |
| 8,617,554 B2 | 12/2013 | Roberts et al. |

(Continued)

OTHER PUBLICATIONS

Errabolu et al., Cloning of a cDNA encoding human centrin, an EF-hand protein of centrosomes and mitotic spindle poles. J Cell Sci (1994) 107 (1): 9-16. (Year: 1994).*

(Continued)

*Primary Examiner* — Aurora M Fontainhas
(74) *Attorney, Agent, or Firm* — Cooley LLP

(57) ABSTRACT

Provided herein are antibodies that specifically bind Centrin-1 and methods of making the same, for use the treatment, prevention, detection, imaging, and diagnosis of cancers including pancreatic and prostate cancer.

20 Claims, 19 Drawing Sheets

Specification includes a Sequence Listing.

(56) References Cited

U.S. PATENT DOCUMENTS

| | | |
|---|---|---|
| 2011/0086349 A1 | 4/2011 | Anjomshoaa et al. |
| 2011/0200627 A1 | 8/2011 | Cunningham et al. |
| 2014/0294891 A1 | 10/2014 | Szalay et al. |
| 2016/0130343 A1 | 5/2016 | Kamogawa et al. |

OTHER PUBLICATIONS

Pulvermuller et al., Calcium-Dependent Assembly of Centrin-G-Protein Complex in Photoreceptor Cells, Molecular and Cellular Biology/ vol. 22, No. 7, Apr. 2002, 2194-2203 (Year: 2002).*

Abnova: "CETN1 monoclonal antibody (M05), clone 4C12", Dec. 19, 2017 (Dec. 19, 2017), XP055834640, Retrieved from the Internet: URL:https://www.abnova.com/PDFServer/outputs/H00001068-M05.pdf.

Extended European Search Report dated Sep. 3, 2021, for EP Application No. 18 891 539.1, filed on Dec. 20, 2018, 9 pages.

International Search Report dated Jun. 10, 2019, for PCT Application No. PCT/US2018/066971, filed on Dec. 20, 2018, 5 pages.

Jiao, R. et al. (2019). "Evaluation of novel highly specific antibodies to cancer testis antigen Centrin-1 for radioimmunoimaging and radioimmunotherapy of pancreatic cancer," Cancer Med. 8:5289-5300.

Kim, J.J. et al. (2013). "CETN1 is a cancer testis antigen with expression in prostate and pancreatic cancers," Biomarker Research 1:22.

Libusova, L. et al. (2005). "Distinct localization of a beta-tubulin epitope in the Tetrahymena thermophila and Paramecium caudatum cortex," Protoplasma 225:157-167.

Novusbio: "Product Datasheet Centrin 1 Antibody (2A6) H00001068-M01" Dec. 19, 2017 (Dec. 19, 2017), XP55834638, Retrieved from the Internet: URL:https://www.novusbio.com/PDFs/H00001068-M01.pdf.

Written Opinion of the International Searching Authority dated Jun. 10, 2019, for PCT Application No. PCT/US2018/066971, filed on Dec. 20, 2018, 5 pages.

Zallocchi, M. et al. (2009). "Localization and expression of clarin-1, the Clrnl gene product, in auditory hair cells and photoreceptors," Hearing Research 255:109-120.

* cited by examiner

FIG. 1

Centrin 1 human (SEQ ID NO: 57)

```
MASGFKKPSA ASTGQRKRVA PKPELTEDQK QEVREAFDLF DVDGSGTIDA KELKVAMRAL
         10         20         30         40         50         60
GFEPRKEEMK KMISEVDREG TGKISPNDFL AVMTQKMSEK DTKEEILKAF RLFDDDETGK
         70         80         90        100        110        120
ISFKNLKRVA NELGENLTDE ELQEMIDEAD RDGDGEVNEE EFLRIMKKTS LY
        130        140        150        160        170
```

Centrin 1 mouse (SEQ ID NO: 58)

```
MASTFRKSNV ASTSYRKVG PKPELTEDQK QEVREAFDLF DSDGSGTIDV KELKVAMRAL
         10         20         30         40         50         60
GFEPRKEEMK RMISEVDKEA TGKISFNDFL AVMTQRMAEK DTKEEILKAF RLFDDDETGK
         70         80         90        100        110        120
ISFKNLKRVA NELGENLTDE ELQEMIDEAD RDGDGEVNEE EFLKIMKKTN LY
        130        140        150        160        170
```

Centrin 2 human (SEQ ID NO: 59)

```
MASNFKKANM ASSSQKRMS PKPELTEEQK QEIREAFDLF DADGTGTIDV KELKVAMRAL
         10         20         30         40         50         60
GFEPKKEEIK KMISEIDKEG TGKMNFGDFL TVMTQKMSEK DTKEEILKAF RLFDDDETGK
         70         80         90        100        110        120
ISFKNLKRVA KELGENLTDE ELQEMIDEAD RDGDGEVSEQ EFLRIMKKTS LY
        130        140        150        160        170
```

FIG. 1
continued

Centrin 1 human vs Centrin 2 human    (SEQ ID NO: 57 vs. SEQ ID NO: 59)

```
1 MASGFKKPSA  ASTQQRKVA   PKPELTEDQK  QEVREAFDLF  DVDGSGTIDA  KELKVAMRAL
2 MASNFKKANM  ASSSQRKRMS  PKPELTEEQK  QEIREAFDLF  DADGTGTIDV  KELKVAMRAL

1 GFEPRKEEMK  KMISEVDREG  TGKISFNDFL  AVMTQKMSEK  DTKEEILKAF  RLFDDDETGK
2 GFEPRKEEIK  KMISEIDKEG  TGKMNFGDFL  TVMTQKMSEK  DTKEEILKAF  RLFDDDETGK

1 ISFKNLKRVA  NELGENLTDE  ELQEMIDEAD  RDGDGEVNEE  EFLRIMKKTS  LY
2 ISFKNLKRVA  KELGENLTDE  ELQEMIDEAD  RDGDGEVSEQ  EFLRIMKKTS  LY
```

Centrin 1 human vs Centrin 1 mouse    (SEQ ID NO: 57 vs. SEQ ID NO: 58)

```
h MASGFKKPSA  ASTQQRKVA   PKPELTEDQK  QEVREAFDLF  DVDGSGTIDA  KELKVAMRAL
m MASTFRKSMV  ASTSIKRVG   PKPELTEDQK  QEVREAFDLF  DSDSSGTIDV  KELKVAMRAL h GFEPRKEEMK  KMISEVDREG  TGKISFNDFL  AVMTQKMSEK  DTKEEILKAF  RLFDDDETGK
m GFEPRKEEMK  RMISEVDKEA  TGKISFNDFL  AVMTQKMAEK  DTKEEILKAF  RLFDDDETGK h ISFKNLKRVA  NELGENLTDE  ELQEMIDEAD  RDGDGEVNEE  EFLRIMKKTS  LY
m ISFKNLKRVA  NELGESLTDE  ELQEMIDEAD  RDGDGEVNEE  EFLKIMKKTN  LY
```

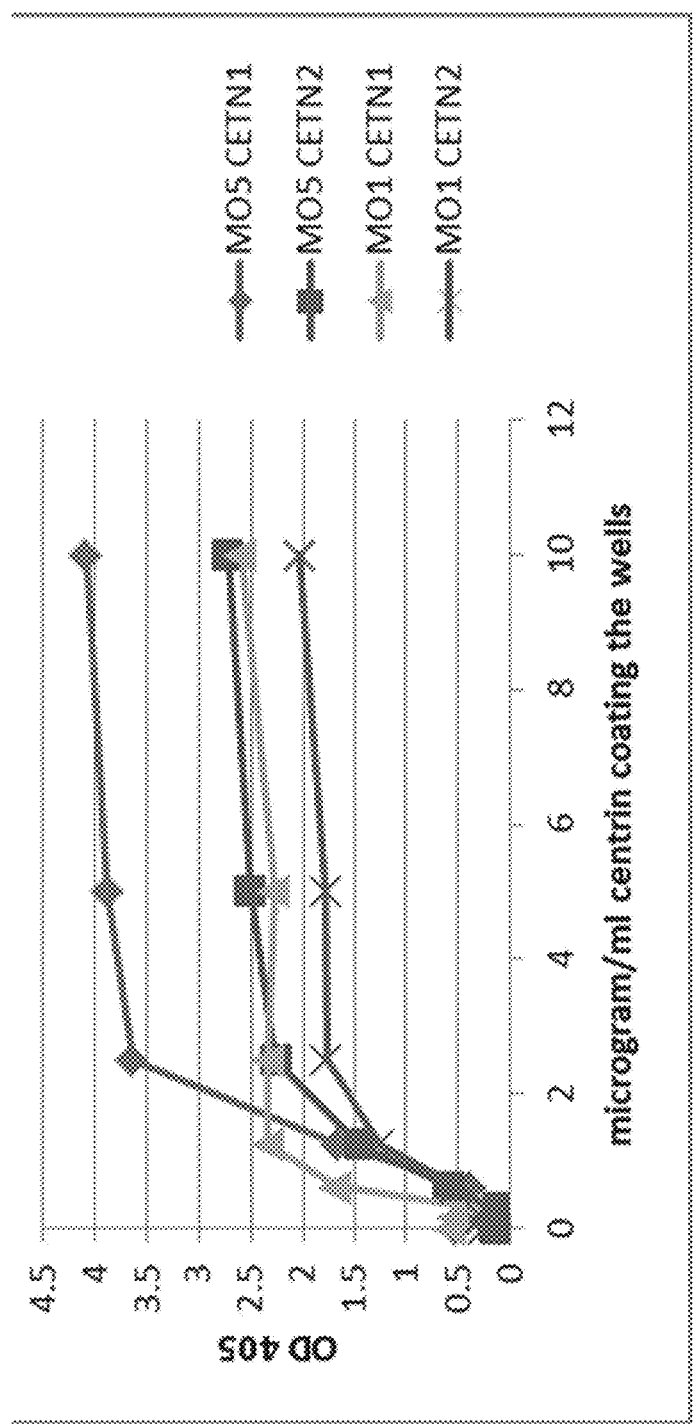
FIG. 2 is a graph showing the results of a titration study of commercially available anti-Centrin 1 antibodies (MO1 and MO5) to determine an optimal concentration for coating wells in ELISA assays.

13A

13B

14A

14B

15A

15B

ANTIBODIES TO CENTRIN-1, METHODS OF MAKING, AND USES THEREOF

CROSS REFERENCE

This application is a U.S. national stage application, filed under 35 U.S.C. § 371, of International Application No. PCT/US2018/066971, filed on Dec. 20, 2018, which claims the benefit under 35 U.S.C. § 119(e) of U.S. Provisional Patent Application No. 62/753,665, filed Oct. 31, 2018, and U.S. Provisional Patent Application No. 62/608,495, filed Dec. 20, 2017. The contents of these applications are incorporated herein by reference in their entireties.

REFERENCE TO SEQUENCE LISTING

This application is being filed electronically via EFS-Web and includes an electronically submitted sequence listing in .txt format. The .txt file contains a sequence listing entitled RADM_003_02US_SeqList ST25.txt created on Jun. 18, 2020, and having a size of 17.6 kilobytes. The sequence listing contained in this .txt file is part of the specification and is incorporated herein by reference in its entirety.

BACKGROUND

Pancreatic ductal adenocarcinoma (PDAC) accounts for more than 90% of pancreatic malignancies, and it is the fourth leading cause of cancer death in the United States with a median survival of less than 6 months and a very low survival rate. The cancer rapidly disseminates to the lymphatic system and distant organs, and because of its aggressive nature, the disease is often already at an incurable stage when it is first diagnosed. Unlike most other solid malignancies, a biopsy of the pancreas is a very invasive procedure, and it is recommended only when a mass suspected to be PDAC is causing an obstruction, or when there is evidence of metastasis and tissue biopsy is necessary to direct chemotherapy.

Prostate cancer is the second most common cancer in men after skin cancer, and one of the leading causes of cancer death among men. The most frequent form of prostate cancer is prostatic adenocarcinoma, which accounts for 90 to 95% of prostate cancer. Although prostatic adenocarcinoma can be detected early by measuring elevated levels of prostate-specific antigen (PSA) in the blood, PSA levels may be affected by different factors, such as an enlarged prostate, older age, prostatitis, and the intake of various drugs, which in turn affect the reliability of the test.

Accordingly, there is a strong need in the art for the development of detection, diagnostic and therapeutic options for pancreatic ductal adenocarcinoma and prostate cancer. Provided herein are compositions and methods that can address this need.

SUMMARY

Centrins are multi-functional calcium-binding phosphoproteins with four Ca2+-binding domains that in all eukaryotes are localized in the centrosomes. Centrin-1 is normally expressed only during neonatal development and in adult testis tissue, but is expressed in some tumor tissues. (Kim et al., Biomark Res. 1: 22 (2013)).

Current detection and treatment of pancreatic and prostate cancer are hampered by the relative lack of specificity of anti-Centrin-1 antibodies available on the market, which do not sufficiently discriminate between Centrin-1 and a related family member, Centrin-2, for effective use in oncology biomarker detection and treatment. Sequencing of Centrin-1 and Centrin-2 showed as high as about 80% homology between the two proteins (FIG. 1), further underlining the challenge in developing antibodies that can specifically bind to Centrin-1.

Provided herein are antibodies that bind Centrin-1 with specificity (Centrin-1 antibodies), and exhibit reduced, little, or no binding to Centrin-2. Also provided herein are methods of making, and methods of use of such antibodies. Methods of use include treatment and detection of cancer, including pancreatic cancer and prostate cancer.

More specifically, in one aspect proved herein is a Centrin-1 antibody that specifically binds Centrin-1. In some embodiments, the antibody is a monoclonal antibody. In some embodiments, the antibody is a polyclonal antibody. In some embodiments, the antibody is a heterogeneous mixture of antibodies that bind Centrin-1, comprising two or more Centrin-1 antibodies. In some embodiments, the antibody is a homogenous mixture of identical Centrin-1 antibodies.

In some embodiments the antibody binds Centrin-1 with at least a 2-fold higher binding affinity relative to its binding to Centrin-2. In some embodiments antibody binds Centrin-1 with at least a 5-fold higher binding affinity relative to its binding to Centrin-2. In some embodiments the antibody binds Centrin-1 with at least a 7-fold higher binding affinity relative to its binding to Centrin-2. In some embodiments the antibody binds exhibits little or no binding to Centrin-2. In some embodiments the antibody is an IgG isotype. In some embodiments the antibody is an IgG1 isotype. In some embodiments the antibody is an IgM isotype.

In some embodiments, the Centrin-1 antibody comprises a VH and a VL, wherein the VH comprises a CDR1 comprising the amino acid sequence set forth in SEQ ID NO. 2 or SEQ ID NO: 40, a CDR2 comprising the amino acid sequence set forth in SEQ ID NO. 3 or SEQ ID NO: 41, and a CDR3 comprising the amino acid sequence set forth in SEQ ID NO. 4 or SEQ ID NO: 42; wherein the VL comprises a CDR1 comprising the amino acid sequence set forth in SEQ ID NO. 10, or SEQ ID NO: 46 or SEQ ID NO: 47, a CDR2 comprising the amino acid sequence set forth in SEQ ID NO. 11 or SEQ ID NO: 48, and a CDR3 comprising the amino acid sequence set forth in SEQ ID NO. 12 or SEQ ID NO: 49.

In some embodiments, the Centrin-1 antibody comprises a VH and a VL, wherein the VH comprises a CDR1 comprising the amino acid sequence set forth in SEQ ID NO. 2 or SEQ ID NO: 40, a CDR2 comprising the amino acid sequence set forth in SEQ ID NO. 3 or SEQ ID NO: 41, and a CDR3 comprising the amino acid sequence set forth in SEQ ID NO. 4 or SEQ ID NO: 42; and wherein the VL comprises a CDR1 comprising the amino acid sequence set forth in SEQ ID NO. 14, SEQ ID NO. 50 or SEQ ID NO. 51; a CDR2 comprising the amino acid sequence set forth in SEQ ID NO. 15 or SEQ ID NO. 52; and a CDR3 comprising the amino acid sequence set forth in SEQ ID NO. 16 or SEQ ID NO. 53.

In some embodiments, the Centrin-1 antibody comprises a VH and a VL, wherein the VH comprises a CDR1 comprising the amino acid sequence set forth in SEQ ID NO. 2 or SEQ ID NO: 40, a CDR2 comprising the amino acid sequence set forth in SEQ ID NO. 3 or SEQ ID NO: 41, and a CDR3 comprising the amino acid sequence set forth in SEQ ID NO. 4 or SEQ ID NO: 42; and wherein the VL comprises a CDR1 comprising the amino acid sequence set forth in SEQ ID NO. 18 or SEQ ID NO. 54, a CDR2 comprising the amino acid sequence set forth in SEQ ID NO. 19 or SEQ ID NO. 55, and a CDR3 comprising the amino acid sequence set forth in SEQ ID NO. 20 or SEQ ID NO. 56.

In some embodiments, the Centrin-1 antibody comprises a VH and a VL, wherein the VH comprises a CDR1 comprising the amino acid sequence set forth in SEQ ID NO. 6 or SEQ ID NO: 43, a CDR2 comprising the amino acid sequence set forth in SEQ ID NO. 7 or SEQ ID NO: 44, and a CDR3 comprising the amino acid sequence set forth in SEQ ID NO. 8 or SEQ ID NO: 45; and wherein the VL comprises a CDR1 comprising the amino acid sequence set forth in SEQ ID NO. 10, or SEQ ID NO: 46 or SEQ ID NO: 47, a CDR2 comprising the amino acid sequence set forth in SEQ ID NO. 11 or SEQ ID NO: 48, and a CDR3 comprising the amino acid sequence set forth in SEQ ID NO. 12 or SEQ ID NO: 49.

In some embodiments, the Centrin-1 antibody comprises a VH and a VL, wherein the VH comprises a CDR1 comprising the amino acid sequence set forth in SEQ ID NO. 6 or SEQ ID NO: 43, a CDR2 comprising the amino acid sequence set forth in SEQ ID NO. 7 or SEQ ID NO: 44, and a CDR3 comprising the amino acid sequence set forth in SEQ ID NO. 8 or SEQ ID NO: 45; and wherein the VL comprises a CDR1 comprising the amino acid sequence set forth in SEQ ID NO. 14, SEQ ID NO. 50 or SEQ ID NO. 51; a CDR2 comprising the amino acid sequence set forth in SEQ ID NO. 15 or SEQ ID NO. 52; and a CDR3 comprising the amino acid sequence set forth in SEQ ID NO. 16 or SEQ ID NO. 53.

In some embodiments, the Centrin-1 antibody comprises a VH and a VL, wherein the VH comprises a CDR1 comprising the amino acid sequence set forth in SEQ ID NO. 6 or SEQ ID NO: 43, a CDR2 comprising the amino acid sequence set forth in SEQ ID NO. 7 or SEQ ID NO: 44, and a CDR3 comprising the amino acid sequence set forth in SEQ ID NO. 8 or SEQ ID NO: 45; and wherein the VL comprises a CDR1 comprising the amino acid sequence set forth in SEQ ID NO. 18 or SEQ ID NO. 54, a CDR2 comprising the amino acid sequence set forth in SEQ ID NO. 19 or SEQ ID NO. 55, and a CDR3 comprising the amino acid sequence set forth in SEQ ID NO. 20 or SEQ ID NO. 56.

In some embodiments, the Centrin-1 antibody comprises a heavy chain variable region (VH) comprising the amino acid sequence of SEQ ID NO: 1, SEQ ID NO: 5, or humanized versions thereof.

In some embodiments, the Centrin-1 antibody comprises a light chain variable region (VL) comprising the amino acid sequence of SEQ ID NO: 9, SEQ ID NO: 13, SEQ ID NO: 17, or humanized versions thereof.

In some embodiments, the Centrin-1 antibody comprises a VH comprising the amino acid sequence of SEQ ID NO. 1 or a humanized version thereof; and a VL comprising the amino acid sequence of SEQ ID NO. 9 or a humanized version thereof.

In some embodiments, the Centrin-1 antibody comprises a VH comprising the amino acid sequence of SEQ ID NO. 5 or a humanized version thereof; and a VL comprising the amino acid sequence of SEQ ID NO. 9 or a humanized version thereof.

In some embodiments, the Centrin-1 antibody comprises a VH comprising the amino acid sequence of SEQ ID NO. 1 or a humanized version thereof; and a VL comprising the amino acid sequence of SEQ ID NO. 13 or a humanized version thereof.

In some embodiments, the Centrin-1 antibody comprises a VH comprising the amino acid sequence of SEQ ID NO. 5 or a humanized version thereof; and a VL comprising the amino acid sequence of SEQ ID NO. 13 or a humanized version thereof.

In some embodiments, the Centrin-1 antibody comprises a VH comprising the amino acid sequence of SEQ ID NO. 1 or a humanized version thereof; and a VL comprising the amino acid sequence of SEQ ID NO. 17 or a humanized version thereof.

In some embodiments, the Centrin-1 antibody comprises a VH comprising the amino acid sequence of SEQ ID NO. 5 or a humanized version thereof; and a VL comprising the amino acid sequence of SEQ ID NO.17 or a humanized version thereof.

In some embodiments, the Centrin-1 antibody comprises a VH, said VH comprising at least one, and up to three, of the CDR sequences of SEQ ID NO: 2, SEQ ID NO: 40, SEQ ID NO: 6, SEQ ID NO: 43, SEQ ID NO: 3, SEQ ID NO: 41, SEQ ID NO: 7, SEQ ID NO: 44, SEQ ID NO: 4, SEQ ID NO: 42, SEQ ID NO: 8 or SEQ ID NO: 45.

In some embodiments, the Centrin-1 antibody comprises a VL, said VL comprising at least one, and up to three, of the CDR sequences of SEQ ID NO: 10, SEQ ID NO: 46, SEQ ID NO: 47, SEQ ID NO: 14, SEQ ID NO: 50, SEQ ID NO: 51, SEQ ID NO: 18, SEQ ID NO: 54, SEQ ID NO: 11, SEQ ID NO: 48, SEQ ID NO: 15, SEQ ID NO: 52, SEQ ID NO: 19, SEQ ID NO: 55, SEQ ID NO: 12, SEQ ID NO: 49, SEQ ID NO: 16, SEQ ID NO: 53, SEQ ID NO: 20 or SEQ ID NO: 56.

In some embodiments, provided herein is a Centrin-1 antibody comprising the HCDRs and LCDRs of Combination 1 of Table 1c.

In some embodiments, provided herein is a Centrin-1 antibody comprising the HCDRs and LCDRs of Combination 2 of Table 1c.

In some embodiments, provided herein is a Centrin-1 antibody comprising the HCDRs and LCDRs of Combination 3 of Table 1c.

In some embodiments, provided herein is a Centrin-1 antibody comprising the HCDRs and LCDRs of Combination 4 of Table 1c.

In some embodiments, provided herein is a Centrin-1 antibody comprising the HCDRs and LCDRs of Combination 5 of Table 1c.

In some embodiments, provided herein is a Centrin-1 antibody comprising the HCDRs and LCDRs of Combination 6 of Table 1c.

In some embodiments the antibody is an antigen-binding fragment thereof. In some embodiments the antibody is a full length antibody. In some embodiments the antibody is conjugated to an agent. In some embodiments, the antibody selectively binds a Centrin-1 epitope, wherein the epitope comprises any one of the epitopes selected from the group consisting of SEQ ID NO: 21-39.

In some embodiments the antibody is conjugated to a detectable label. In some embodiments the antibody is conjugated to a radionuclide. In some embodiments, the antibody is conjugated to the radionuclide directly, while in other embodiments the antibody is conjugated to the radionuclide through a linker molecule. In some embodiments, the antibody is conjugated to the radionuclide through a linker, for example either randomly or in a site directed manner. In some embodiments the radionuclide is an α-emitting or a β-emitting radioisotope. In some embodiments the radionuclide comprises 213-Bismuth, 177-Lutetium, 212-Lead, 225 Actinium, 227-Thorium, 186-Rhenium, or 188-Rhenium. In some embodiments the antibody is conjugated to a cytotoxin. In some embodiments the antibody is bispecific. In some embodiments the antibody comprises a first specificity to Centrin-1 and a second specificity to an immune checkpoint inhibitor. In some embodiments the antibody is humanized. Also provided herein are pharmaceutical compositions comprising these antibodies and a pharmaceutically acceptable excipient.

In another aspect, provided herein is a method of treating a cancer in a subject in need thereof comprising administering to the subject in need thereof a therapeutically effective amount of these antibodies or compositions. In some embodiments the cancer is pancreatic cancer or prostate cancer. In some embodiments the pancreatic cancer is pancreatic ductal adenocarcinoma (PDAC). In some embodiments the prostate cancer is adenocarcinoma of the prostate. In some embodiments the administration is systemic, regional, local, or intracavity administration.

In another aspect, provided herein is a method of determining that a subject has, or is at risk for developing, cancer comprising contacting a biological sample from the subject with any one of the antibodies described herein, and determining that the subject has, or is at risk for developing, cancer if the relative level of Centrin-1 is higher than a control value. In a related aspect, provided herein is a method of detecting a cancer in a subject comprising administering to the subject any one of the antibodies described herein. In some embodiments the cancer is pancreatic cancer or prostate cancer. In some embodiments the pancreatic cancer is pancreatic ductal adenocarcinoma (PDAC). In some embodiments the subject has a family history of pancreatic ductal adenocarcinoma (PDAC). In some embodiments the prostate cancer is adenocarcinoma of the prostate. In some embodiments the subject is at risk of developing, is suspected to have developed or has developed pancreatic cancer or prostate cancer. In some embodiments the cancer is metastasized. In some embodiments the sample is a liquid biopsy, tissue biopsy, or blood sample. In some embodiments, these methods comprise administering a treatment to the subject.

Also provided herein are nucleic acid molecules, recombinant expression vectors, and host cells expressing any of the antibodies described herein. Also provided herein is a method of producing any of the antibodies described herein by growing a host cell comprising a recombinant expression vector comprising a nucleic acid molecule encoding any one of the antibodies disclosed herein under conditions permitting production of the antibody and recovering the produced antibody.

BRIEF DESCRIPTION OF THE DRAWINGS

FIG. 1 shows the amino acid sequences of human Centrin-1 (SEQ ID NO: 57), mouse Centrin-1 (SEQ ID NO: 58), human Centrin-2 (SEQ ID NO: 59), an alignment of the amino acid sequences of human Centrin-1 against human Centrin-2, and an alignment of the amino acid sequences of human Centrin-1 against mouse Centrin-1.

FIG. 2 is a graph showing the results of a titration of commercially available anti-Centrin-1 antibodies (M01 and M05) against Centrin-1 and Centrin-2 antigen on solid phase to determine an optimal concentration for coating wells in ELISA-based assays.

FIG. 9A shows results from microSPECT/CT imaging of MiaPaCa2 tumor-bearing mouse at about 1 hour, about 24 hours, about 48 hours, about 72 hours and about 168 hours post administration of 177Lu-labeled antibody produced by the 69-11 clone to Centrin-1. The arrows point to the tumors. FIG. 9B shows immunohistochemistry results of the MiaPaCa2 tumor stained with the antibody produced by the 69-11 clone. FIG. 9C shows immunohistochemistry results for the same tumor stained with isotype matching control MOPC21.

DETAILED DESCRIPTION OF THE INVENTION

Figure 3A:
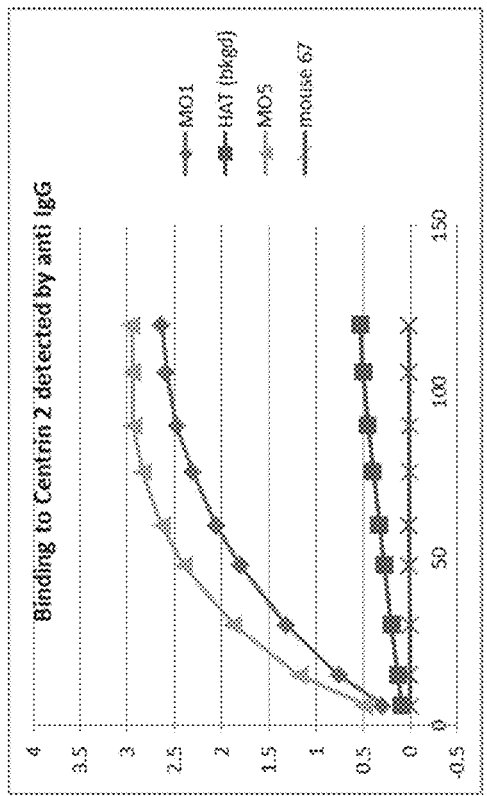
FIG. 3A (left panel) and 3B (right panel) are graphs comparing the binding of commercial antibodies M01 and M05 to Centrin-1 (left panel) and Centrin-2 (right panel) using capture ELISA. Background levels were determined using media from the cell culture (HAT). Antibodies from mouse 67 was used as a negative control.

Provided herein are antibodies that bind the Centrin-1 protein (the Centrin-1 protein may be interchangeably referred to herein as CETN1) with specificity, methods of making and methods of use of such antibodies. Methods of use include treatment and detection of cancer, including pancreatic cancer and prostate cancer.

Unless defined otherwise herein, all technical and scientific terms used herein have the same meaning as commonly understood by one of ordinary skill in the art to which this invention belongs.

Numeric ranges are inclusive of the numbers defining the range.

For purposes of interpreting this specification, the following definitions will apply and whenever appropriate, terms used in the singular will also include the plural and vice versa. In the event that any definition set forth below conflicts with any document incorporated herein by reference, the definition set forth shall control.

As used herein, the singular form "a", "an", "the", and "antibody" includes plural references unless indicated otherwise.

It is understood that aspects and embodiments of the invention described herein include "comprising," "consisting," and "consisting essentially of" aspects and embodiments.

The term "about" as used herein refers to the usual error range for the respective value readily known to the skilled person in this technical field. Reference to "about" a value or parameter herein includes (and describes) embodiments that are directed to that value or parameter per se. As used herein, the term "about" when preceding a numerical value indicates the value plus or minus a range of 10%. For example, "about 100" encompasses 90 and 110.

The terms "treat," "treatment," and "treating," as used herein, refer to an approach for obtaining beneficial or desired results, for example, clinical results. For the purposes of this disclosure, beneficial or desired results may include inhibiting, reducing or suppressing the progression of cancer; ameliorating, or reducing the development of symptoms of a disease or disorder; or a combination thereof.

The terms "CETN1" or "Centrin-1" may be used interchangeably and may refer to the gene encoding the Centrin protein; or the Centrin protein itself. Similarly, the terms "CETN2" or "Centrin-2" may be used interchangeably and may refer to the gene encoding the Centrin protein; or the Centrin protein itself.

Other definitions of terms may appear throughout the specification.

Centrin-1 Antibodies

Provided herein are antibodies that specifically bind to mammalian Centrin-1. In some embodiments, the Centrin-1 is human Centrin-1.

The term "antibody" as used herein throughout is in the broadest sense and includes, but is not limited to, a monoclonal antibody, a mixture of heterogeneous antibodies that each bind Centrin-1, polyclonal antibody, human antibody, humanized antibody, non-human antibody, chimeric antibody, bispecific antibody, multi-specific antibody, antigen-binding fragments of the antibody (e.g Fab fragment, a Fab'2 fragment, a CDR or a ScFv) that retain specificity for a Centrin-1 antigen.

In some embodiments the disclosure provides a homogenous mixture of Centrin-1 binding antibodies.

In some embodiments the disclosure provides a heterogeneous mixture of Centrin-1 binding antibodies, wherein the heterogeneous mixture comprises two or more of the Cetrin-1 antibodies provided herein.

In some embodiments the disclosure provides a composition comprising a homogenous mixture of Centrin-1 antibodies. In some embodiments, the disclosure provides a composition comprising a heterogeneous mixture of Centrin-1 antibodies, wherein the heterogeneous mixture comprises two or more Centrin-1 antibodies of the disclosure.

Table 1a provides exemplary amino acid sequences of heavy chain variable regions (VH) and light chain variable regions (VL) of Centrin-1 antibodies of the disclosure.

TABLE 1a

| SEQ ID NO: | Amino acid sequence | Description |
|---|---|---|
| 1 | QVQLQQSGAELVRPGSSVKISCKASGY VFSRYWMNWVKQRPGQGLEWIGQIYP GDGDTDYNGEFKGKATLTADRSSSTAY MQLSSLTSEDSAVYFCAREFAYWGQGT LVTVSA | VH of a Centrin-1 antibody |
| 5 | EVKLVESGGGLVQPGGSLRLSCATSGFT FTDYYMSWVRQPPGKALEWLGFIRNK ANGYTTEYSASVKGRFTISRDNSQSILY LQMNTLRAEDSATYYCARAGNYGGFD VWGAGTTVTVSS | VH of a Centrin-1 antibody |
| 9 | DIVMTQSHKFMSTSVGDRVSITCKASQ DVGTAVAWYQQKPGQSPKLLIYWAST RHTGVPDRFTGSGSGTDFTLTISNVQSE DLADYFCQQYSSYPYTFGGGTKLEIK | VL of a Centrin-1 antibody |
| 13 | SIVMTQTPKFLLVSAGDRVTITCKASQS VSNDVAWYQQKPGQSPKLLIYYASNRY TGVPDRFTGSGYGTDFTFTISTVQAEDL AVYFCQQDYNSPFTFGGGTKLEIK | VL of a Centrin-1 antibody |
| 17 | DIQMTQSPSSLSIFLGGKVTITCKASQDI NKHIAWYQHRPGKSPWLLIHYTSTLQP GIPSRFSGSGSGRDYSLSIINLEPEDFATY YCLQYDNLWTFGGGTKLEIK | VL of a Centrin-1 antibody |

Table 1b provides exemplary amino acid sequences of predicted complementary determining regions (CDRs) of the VHs and VLs of the Centrin-1 antibodies of the disclosure. As used herein throughout HCDR1, HCDR2, and HCDR3 refer to the CDR1, CDR2, and CDR3 of a VH; and LCDR1, LCDR2, and LCDR3 refer to CDR1, CDR2 and CDR3 of a VL.

TABLE 1b

| SEQ ID NO: | Amino acid sequence | Description |
|---|---|---|
| 2 | YVFSRYWMN | HCDR1 of SEQ ID NO: 1 |
| 40 | RYWMN | HCDR1 of SEQ ID NO: 1 |
| 3 | WIGQIYPGDGDTDY | HCDR2 of SEQ ID NO: 1 |
| 41 | IYPGDGDTDYNGEFKG | HCDR2 of SEQ ID NO: 1 |
| 4 | REFAY | HCDR3 of SEQ ID NO: 1 |
| 42 | EFAY | HCDR3 of SEQ ID NO: 1 |
| 6 | FTFTDYYMS | HCDR1 of SEQ ID NO: 5 |
| 43 | DYYMS | HCDR1 of SEQ ID NO: 5 |
| 7 | WLGFIRNKANGYTTEYSA | HCDR2 of SEQ ID NO: 5 |
| 44 | FIRNKANGYTTEYSASVKG | HCDR2 of SEQ ID NO: 5 |
| 8 | ARAGNYGGFDV | HCDR3 of SEQ ID NO: 5 |
| 45 | AGNYGGFDV | HCDR3 of SEQ ID NO: 5 |
| 10 | SQDVGTAVA | LCDR1 of SEQ ID NO: 9 |

TABLE 1b-continued

| SEQ ID NO: | Amino acid sequence | Description |
|---|---|---|
| 46 | QDVGTAVA | LCDR1 of SEQ ID NO: 9 |
| 47 | KASQDVGTAVA | LCDR1 of SEQ ID NO: 9 |
| 11 | LLIYWASTRHT | LCDR2 of SEQ ID NO: 9 |
| 48 | WASTRHT | LCDR2 of SEQ ID NO: 9 |
| 12 | QQYSSYPY | LCDR3 of SEQ ID NO: 9 |
| 49 | QQYSSYPYT | LCDR3 of SEQ ID NO: 9 |
| 14 | SQSVSNDVA | LCDR1 of SEQ ID NO: 13 |
| 50 | QSVSNDVA | LCDR1 of SEQ ID NO: 13 |
| 51 | KASQSVSNDVA | LCDR1 of SEQ ID NO: 13 |
| 15 | LLIYYASNRYT | LCDR2 of SEQ ID NO: 13 |
| 52 | YASNRYT | LCDR2 of SEQ ID NO: 13 |
| 16 | QQDYNSPF | LCDR3 of SEQ ID NO: 13 |
| 53 | QQDYNSPFT | LCDR3 of SEQ ID NO: 13 |
| 18 | QDINKHIA | LCDR1 of SEQ ID NO: 17 |
| 54 | KASQDINKHIA | LCDR1 of SEQ ID NO: 17 |
| 19 | WLLIHYTSTLQP | LCDR2 of SEQ ID NO: 17 |
| 55 | TSTLQP | LCDR2 of SEQ ID NO: 17 |
| 20 | LQYDNLW | LCDR3 of SEQ ID NO: 17 |
| 56 | LQYDNLWT | LCDR3 of SEQ ID NO: 17 |

Table 1c lists exemplary combinations of HCDRs and LCDRs present in VHs and VLs of Centrin-1 antibodies.

TABLE 1c

| Combination No. | VH | VL |
|---|---|---|
| Combination No. 1 | HCDR1: SEQ ID NO: 2 or 40; HCDR2: SEQ ID NO: 3 or 41; HCDR3: SEQ ID NO: 4 or 42 | LCDR1: SEQ ID NO: 10, 46 or 47; LCDR2: SEQ ID NO: 11 or 48 LCDR3: SEQ ID NO: 12 or 49 |
| Combination No. 2 | HCDR1: SEQ ID NO: 2 or 40; HCDR2: SEQ ID NO: 3 or 41; HCDR3: SEQ ID NO: 4 or 42 | LCDR1: SEQ ID NO: 14, 50 or 51; LCDR2: SEQ ID NO: 15 or 52 LCDR3: SEQ ID NO: 16 or 53 |
| Combination No. 3 | HCDR1: SEQ ID NO: 2 or 40; HCDR2: SEQ ID NO: 3 or 41; HCDR3: SEQ ID NO: 4 or 42 | LCDR1: SEQ ID NO: 18 or 54; LCDR2: SEQ ID NO: 19 or 55 LCDR3: SEQ ID NO: 20 or 56 |
| Combination No. 4 | HCDR1: SEQ ID NO: 6 or 43; HCDR2: SEQ ID NO: 7 or 44; HCDR3: SEQ ID NO: 8 or 45 | LCDR1: SEQ ID NO: 10, 46 or 47; LCDR2: SEQ ID NO: 11 or 48 LCDR3: SEQ ID NO: 12 or 49 |
| Combination No. 5 | HCDR1: SEQ ID NO: 6 or 43; HCDR2: SEQ ID NO: 7 or 44; HCDR3: SEQ ID NO: 8 or 45 | LCDR1: SEQ ID NO: 14, 50 or 51; LCDR2: SEQ ID NO: 15 or 52 LCDR3: SEQ ID NO: 16 or 53 |
| Combination No. 6 | HCDR1: SEQ ID NO: 6 or 43; HCDR2: SEQ ID NO: 7 or 44; HCDR3: SEQ ID NO: 8 or 45 | LCDR1: SEQ ID NO: 18 or 54; LCDR2: SEQ ID NO: 19 or 55 LCDR3: SEQ ID NO: 20 or 56 |

In some embodiments, the Centrin-1 antibody comprises any one of the VHs and/or any of the VLs listed in Table 1a. In some embodiments, the Centrin-1 antibody comprises a VH comprising the amino acid sequence of SEQ ID NO: 1 or SEQ ID NO: 5. In some embodiments, the Centrin-1 antibody comprises a VL comprising the amino acid sequence of SEQ ID NO: 9, SEQ ID NO: 13, or SEQ ID NO: 17. In some embodiments, the Centrin-1 antibody comprises a VH comprising the amino acid sequence of SEQ ID NO: for SEQ ID NO: 5; and comprises a VL comprising the amino acid sequence of SEQ ID NO: 9, SEQ ID NO: 13, or SEQ ID NO: 17.

In some embodiments, the VH of the Centrin-1 antibody comprises any one or more of the HCDRs listed in Table 1b. In exemplary embodiments, the VH of the Centrin-1 antibody comprises a HCDR1 comprising SEQ ID NO: 2, SEQ ID NO. 40, SEQ ID NO: 6 or SEQ ID NO: 43; a HCDR2 comprising SEQ ID NO: 3, SEQ ID NO: 41, SEQ ID NO.

7, or SEQ ID NO. 44; and/or a HCDR3 comprising SEQ ID NO. 4, SEQ ID NO. 42, SEQ ID NO. 8 or SEQ ID NO. 45.

In some embodiments, the VL of the Centrin-1 antibody comprises any one or more of the LCDRs listed in Table 1b. In exemplary embodiments, the VL of the Centrin-1 antibody comprises an LCDR1 comprising SEQ ID NO. 10, SEQ ID NO. 46, SEQ ID NO. 47, SEQ ID NO. 14, SEQ ID NO. 50, SEQ ID NO. 51, SEQ ID NO. 18 or SEQ ID NO. 54; an LCDR2 comprising SEQ ID NO. 11, SEQ ID NO. 48, SEQ ID NO. 15, or SEQ ID NO. 52, SEQ ID NO. 19, or SEQ ID NO. 55; and/or a LCDR3 comprising SEQ ID NO. 12, SEQ ID NO. 49, SEQ ID NO. 16, SEQ ID NO. 20 or SEQ ID NO. 56.

In some embodiments, the VH of the Centrin-1 antibody comprises any one or more of the HCDRs listed in Table 1b and the VL of the Centrin-1 antibody comprises any one or more of the LCDRs listed in Table 1b.

In some embodiments, the VH of the Centrin-1 antibody comprises a HCDR1 comprising SEQ ID NO. 2, SEQ ID NO. 40, SEQ ID NO. 6 or SEQ ID NO. 43; a HCDR2 comprising SEQ ID NO. 3, SEQ ID NO. 41, SEQ ID NO. 7, or SEQ ID NO. 44; and/or a HCDR3 comprising SEQ ID NO. 4, SEQ ID NO. 42, SEQ ID NO. 8 or SEQ ID NO. 45; and the VL of the Centrin-1 antibody comprises an LCDR1 comprising SEQ ID NO. 10, SEQ ID NO. 46, SEQ ID NO. 47, SEQ ID NO. 14, SEQ ID NO. 50, SEQ ID NO. 51, SEQ ID NO. 18 or SEQ ID NO. 54; an LCDR2 comprising SEQ ID NO. 11, SEQ ID NO. 48, SEQ ID NO. 15, or SEQ ID NO. 52, SEQ ID NO. 19, or SEQ ID NO. 55; and/or an LCDR3 comprising SEQ ID NO. 12, SEQ ID NO. 49, SEQ ID NO. 16, SEQ ID NO. 53, SEQ ID NO. 20 or SEQ ID NO. 56.

In some embodiments, the Centrin-1 antibody comprises HCDRs and LCDRs in any one of the combinations 1 through 6 listed in Table 1c. For example in some embodiments the Centrin-1 antibody comprises the HCDRs and the LCDRs of Combination 1 of Table 1c, the Centrin-1 antibody comprises the HCDRs and the LCDRs of Combination 2 of Table 1c, the Centrin-1 antibody comprises the HCDRs and the LCDRs of Combination 3 of Table 1c, the Centrin-1 antibody comprises the HCDRs and the LCDRs of Combination 4 of Table 1c, the Centrin-1 antibody comprises the HCDRs and the LCDRs of Combination 5 of Table 1c, or the Centrin-1 antibody comprises the HCDRs and the LCDRs of Combination 6 of Table 1c.

In some embodiments, the Centrin-1 antibody is a humanized antibody that specifically binds to Centrin-1. Any one of the antibodies described above can be humanized.

In some embodiments, the Centrin-1 antibody that is humanized comprises any one of the VHs and/or any of the VLs listed in Table 1a. In some embodiments, the Centrin-1 antibody that is humanized comprises a VH comprising the amino acid sequence of SEQ ID NO: 1 or SEQ ID NO: 5. In some embodiments, the Centrin-1 antibody that is humanized comprises a VL comprising the amino acid sequence of SEQ ID NO: 9, SEQ ID NO: 13, or SEQ ID NO: 17. In some embodiments, the Centrin-1 antibody that is humanized comprises a VH comprising the amino acid sequence of SEQ ID NO: for SEQ ID NO: 5; and comprises a VL comprising the amino acid sequence of SEQ ID NO: 9, SEQ ID NO: 13, or SEQ ID NO: 17.

In some embodiments, the VH of the humanized Centrin-1 antibody comprises any one or more of the HCDRs listed in Table 1b. In exemplary embodiments, the VH of the humanized Centrin-1 antibody comprises a HCDR1 comprising SEQ ID NO. 2, SEQ ID NO. 40, SEQ ID NO. 6 or SEQ ID NO. 43; a HCDR2 comprising SEQ ID NO. 3, SEQ ID NO. 41, SEQ ID NO. 7, or SEQ ID NO. 44; and/or an HCDR3 comprising SEQ ID NO. 4, SEQ ID NO. 42, SEQ ID NO. 8 or SEQ ID NO. 45.

In some embodiments, the VL of the humanized Centrin-1 antibody comprises any one or more of the LCDRs listed in Table 1b. In exemplary embodiments, the VL of the humanized Centrin-1 antibody comprises an LCDR1 comprising SEQ ID NO. 10, SEQ ID NO. 46, SEQ ID NO. 47, SEQ ID NO. 14, SEQ ID NO. 50, SEQ ID NO. 51, SEQ ID NO. 18 or SEQ ID NO. 54; an LCDR2 comprising SEQ ID NO. 11, SEQ ID NO. 48, SEQ ID NO. 15, or SEQ ID NO. 52, SEQ ID NO. 19, or SEQ ID NO. 55; and/or an LCDR3 comprising SEQ ID NO. 12, SEQ ID NO. 49, SEQ ID NO. 16, SEQ ID NO. 53, SEQ ID NO. 20 or SEQ ID NO. 56.

In some embodiments, the VH of the humanized Centrin-1 antibody comprises any one or more of the HCDRs listed in Table 1b and the VL of the humanized Centrin-1 antibody comprises any one or more of the LCDRs listed in Table 1b.

In some embodiments, the VH of the humanized Centrin-1 antibody comprises a HCDR1 comprising SEQ ID NO. 2, SEQ ID NO. 40, SEQ ID NO. 6 or SEQ ID NO. 43; a HCDR2 comprising SEQ ID NO. 3, SEQ ID NO. 41, SEQ ID NO. 7, or SEQ ID NO. 44; and/or an HCDR3 comprising SEQ ID NO. 4, SEQ ID NO. 42, SEQ ID NO. 8 or SEQ ID NO. 45; and the VL of the humanized Centrin-1 antibody comprises an LCDR1 comprising SEQ ID NO. 10, SEQ ID NO. 46, SEQ ID NO. 47, SEQ ID NO. 14, SEQ ID NO. 50, SEQ ID NO. 51, SEQ ID NO. 18 or SEQ ID NO. 54; an LCDR2 comprising SEQ ID NO. 11, SEQ ID NO. 48, SEQ ID NO. 15, or SEQ ID NO. 52, SEQ ID NO. 19, or SEQ ID NO. 55; and/or an LCDR3 comprising SEQ ID NO. 12, SEQ ID NO. 49, SEQ ID NO. 16, SEQ ID NO. 53, SEQ ID NO. 20 or SEQ ID NO. 56.

In some embodiments, the humanized Centrin-1 antibody comprises HCDRs and LCDRs in any one of the combinations 1 through 6 listed in Table 1c. For example in some embodiments the humanized Centrin-1 antibody comprises the HCDRs and the LCDRs of Combination 1 of Table 1c, the humanized Centrin-1 antibody comprises the HCDRs and the LCDRs of Combination 2 of Table 1c, the humanized Centrin-1 antibody comprises the HCDRs and the LCDRs of Combination 3 of Table 1c, the humanized Centrin-1 antibody comprises the HCDRs and the LCDRs of Combination 4 of Table 1c, the humanized Centrin-1 antibody comprises the HCDRs and the LCDRs of Combination 5 of Table 1c, or the humanized Centrin-1 antibody comprises the HCDRs and the LCDRs of Combination 6 of Table 1c.

In some embodiments, the antibody is a chimeric antibody that specifically binds to Centrin-1. In some exemplary embodiments, the antibody is a chimeric mouse-human antibody. The chimeric mouse-human antibody can comprise human variable regions and mouse constant regions. Any one of the antibodies described above can be made into a chimeric antibody.

In some embodiments, the Centrin-1 antibody that is chimeric comprises any one of the VHs and/or any of the VLs listed in Table 1a, or humanized versions thereof. In some embodiments, the Centrin-1 antibody that is chimeric comprises a VH comprising the amino acid sequence of SEQ ID NO: 1, SEQ ID NO: 5; or humanized versions thereof. In some embodiments, the Centrin-1 antibody that is chimeric comprises a VL comprising the amino acid sequence of SEQ ID NO: 9, SEQ ID NO: 13, SEQ ID NO: 17; or humanized versions thereof. In some embodiments, the Centrin-1 antibody that is chimeric comprises a VH comprising the amino acid sequence of SEQ ID NO: 1, SEQ ID NO: 5, or humanized versions thereof; and comprises a VL comprising the amino acid sequence of SEQ ID NO: 9, SEQ ID NO: 13, SEQ ID NO: 17; or humanized versions thereof.

In some embodiments, the VH of the chimeric Centrin-1 antibody comprises any one or more of the HCDRs listed in Table 1b. In exemplary embodiments, the VH of the chimeric Centrin-1 antibody comprises a HCDR1 comprising SEQ ID NO. 2, SEQ ID NO. 40, SEQ ID NO. 6 or SEQ ID NO. 43; a HCDR2 comprising SEQ ID NO. 3, SEQ ID NO. 41, SEQ ID NO. 7, or SEQ ID NO. 44; and/or an HCDR3 comprising SEQ ID NO. 4, SEQ ID NO. 42, SEQ ID NO. 8 or SEQ ID NO. 45.

In some embodiments, the VL of the chimeric Centrin-1 antibody comprises any one or more of the LCDRs listed in Table 1b. In exemplary embodiments, the VL of the chimeric Centrin-1 antibody comprises an LCDR1 comprising SEQ ID NO. 10, SEQ ID NO. 46, SEQ ID NO. 47, SEQ ID NO. 14, SEQ ID NO. 50, SEQ ID NO. 51, SEQ ID NO. 18 or SEQ ID NO. 54; an LCDR2 comprising SEQ ID NO. 11, SEQ ID NO. 48, SEQ ID NO. 15, or SEQ ID NO. 52, SEQ ID NO. 19, or SEQ ID NO. 55; and/or an LCDR3 comprising SEQ ID NO. 12, SEQ ID NO. 49, SEQ ID NO. 16, SEQ ID NO. 53, SEQ ID NO. 20 or SEQ ID NO. 56.

In some embodiments, the VH of the chimeric Centrin-1 antibody comprises any one or more of the HCDRs listed in Table 1b and the VL of the chimeric Centrin-1 antibody comprises any one or more of the LCDRs listed in Table 1b.

In some embodiments, the VH of the chimeric Centrin-1 antibody comprises a HCDR1 comprising SEQ ID NO. 2, SEQ ID NO. 40, SEQ ID NO. 6 or SEQ ID NO. 43; a HCDR2 comprising SEQ ID NO. 3, SEQ ID NO. 41, SEQ ID NO. 7, or SEQ ID NO. 44; and/or an HCDR3 comprising SEQ ID NO. 4, SEQ ID NO. 42, SEQ ID NO. 8 or SEQ ID NO. 45; and the VL of the chimeric Centrin-1 antibody comprises an LCDR1 comprising SEQ ID NO. 10, SEQ ID NO. 46, SEQ ID NO. 47, SEQ ID NO. 14, SEQ ID NO. 50, SEQ ID NO. 51, SEQ ID NO. 18 or SEQ ID NO. 54; an LCDR2 comprising SEQ ID NO. 11, SEQ ID NO. 48, SEQ ID NO. 15, or SEQ ID NO. 52, SEQ ID NO. 19, or SEQ ID NO. 55; and/or an LCDR3 comprising SEQ ID NO. 12, SEQ ID NO. 49, SEQ ID NO. 16, SEQ ID NO. 53, SEQ ID NO. 20 or SEQ ID NO. 56.

In some embodiments, the chimeric Centrin-1 antibody comprises HCDRs and LCDRs in any one of the combinations 1 through 6 listed in Table 1c. For example in some embodiments the chimeric Centrin-1 antibody comprises the HCDRs and the LCDRs of Combination 1 of Table 1c, the chimeric Centrin-1 antibody comprises the HCDRs and the LCDRs of Combination 2 of Table 1c, the chimeric Centrin-1 antibody comprises the HCDRs and the LCDRs of Combination 3 of Table 1c, the chimeric Centrin-1 antibody comprises the HCDRs and the LCDRs of Combination 4 of Table 1c, the chimeric Centrin-1 antibody comprises the HCDRs and the LCDRs of Combination 5 of Table 1c, or the chimeric Centrin-1 antibody comprises the HCDRs and the LCDRs of Combination 6 of Table 1c.

In other exemplary embodiments, the Centrin-1 antibody is a bispecific antibody. For example, the bispecific antibody can comprise a first specificity to Centrin-1 and a second specificity to an immune checkpoint inhibitor, e.g. CTLA4, PD-1, or PD-L1. Any one of the antibodies described above can used in the context of a bispecific antibody.

In some embodiments, the Centrin-1 antibody that is bispecific comprises any one of the VHs and/or any of the VLs listed in Table 1a, or humanized versions thereof. In some embodiments, the Centrin-1 antibody that is bispecific comprises a VH comprising the amino acid sequence of SEQ ID NO: 1, SEQ ID NO: 5; or humanized versions thereof. In some embodiments, the Centrin-1 antibody that is bispecific comprises a VL comprising the amino acid sequence of SEQ ID NO: 9, SEQ ID NO: 13, SEQ ID NO: 17; or humanized versions thereof. In some embodiments, the Centrin-1 antibody that is bispecific comprises a VH comprising the amino acid sequence of SEQ ID NO: 1, SEQ ID NO: 5, or humanized versions thereof; and comprises a VL comprising the amino acid sequence of SEQ ID NO: 9, SEQ ID NO: 13, SEQ ID NO: 17; or humanized versions thereof.

In some embodiments, the VH of the bispecific Centrin-1 antibody comprises any one or more of the HCDRs listed in Table 1b. In exemplary embodiments, the VH of the bispecific Centrin-1 antibody comprises a HCDR1 comprising SEQ ID NO. 2, SEQ ID NO. 40, SEQ ID NO. 6 or SEQ ID NO. 43; a HCDR2 comprising SEQ ID NO. 3, SEQ ID NO. 41, SEQ ID NO. 7, or SEQ ID NO. 44; and/or an HCDR3 comprising SEQ ID NO. 4, SEQ ID NO. 42, SEQ ID NO. 8 or SEQ ID NO. 45.

In some embodiments, the VL of the bispecific Centrin-1 antibody comprises any one or more of the LCDRs listed in Table 1b. In exemplary embodiments, the VL of the bispecific Centrin-1 antibody comprises an LCDR1 comprising SEQ ID NO. 10, SEQ ID NO. 46, SEQ ID NO. 47, SEQ ID NO. 14, SEQ ID NO. 50, SEQ ID NO. 51, SEQ ID NO. 18 or SEQ ID NO. 54; an LCDR2 comprising SEQ ID NO. 11, SEQ ID NO. 48, SEQ ID NO. 15, or SEQ ID NO. 52, SEQ ID NO. 19, or SEQ ID NO. 55; and/or an LCDR3 comprising SEQ ID NO. 12, SEQ ID NO. 49, SEQ ID NO. 16, SEQ ID NO. 53, SEQ ID NO. 20 or SEQ ID NO. 56.

In some embodiments, the VH of the bispecific Centrin-1 antibody comprises any one or more of the HCDRs listed in Table 1b and the VL of the bispecific Centrin-1 antibody comprises any one or more of the LCDRs listed in Table 1b.

In some embodiments, the VH of the bispecific Centrin-1 antibody comprises a HCDR1 comprising SEQ ID NO. 2, SEQ ID NO. 40, SEQ ID NO. 6 or SEQ ID NO. 43; a HCDR2 comprising SEQ ID NO. 3, SEQ ID NO. 41, SEQ ID NO. 7, or SEQ ID NO. 44; and/or an HCDR3 comprising SEQ ID NO. 4, SEQ ID NO. 42, SEQ ID NO. 8 or SEQ ID NO. 45; and the VL of the bispecific Centrin-1 antibody comprises an LCDR1 comprising SEQ ID NO. 10, SEQ ID NO. 46, SEQ ID NO. 47, SEQ ID NO. 14, SEQ ID NO. 50, SEQ ID NO. 51, SEQ ID NO. 18 or SEQ ID NO. 54; an LCDR2 comprising SEQ ID NO. 11, SEQ ID NO. 48, SEQ ID NO. 15, or SEQ ID NO. 52, SEQ ID NO. 19, or SEQ ID NO. 55; and/or an LCDR3 comprising SEQ ID NO. 12, SEQ ID NO. 49, SEQ ID NO. 16, SEQ ID NO. 53, SEQ ID NO. 20 or SEQ ID NO. 56.

In some embodiments, the bispecific Centrin-1 antibody comprises HCDRs and LCDRs in any one of the combinations 1 through 6 listed in Table 1c. For example in some embodiments the bispecific Centrin-1 antibody comprises the HCDRs and the LCDRs of Combination 1 of Table 1c, the bispecific Centrin-1 antibody comprises the HCDRs and the LCDRs of Combination 2 of Table 1c, the bispecific Centrin-1 antibody comprises the HCDRs and the LCDRs of Combination 3 of Table 1c, the bispecific Centrin-1 antibody comprises the HCDRs and the LCDRs of Combination 4 of Table 1c, the bispecific Centrin-1 antibody comprises the HCDRs and the LCDRs of Combination 5 of Table 1c, or the bispecific Centrin-1 antibody comprises the HCDRs and the LCDRs of Combination 6 of Table 1c.

The Centrin-1 antibodies of the disclosure can be any of an IgA, IgD, IgE, IgG, or IgM antibody. The IgG antibody can be an IgG1, IgG2, IgG2a, IgG2b, IgG3 or IgG4 antibody. A combination of any of these antibodies can also be used. In some embodiments, the Centrin-1 antibody is an IgG1 antibody.

In some embodiments, the Centrin-1 IgG1 antibody comprises any one of the VHs and/or any of the VLs listed in Table 1a, or humanized versions thereof. In some embodiments, the Centrin-1 IgG1 antibody comprises a VH comprising the amino acid sequence of SEQ ID NO: 1, SEQ ID NO: 5; or humanized versions thereof. In some embodiments, the Centrin-1 IgG1 antibody comprises a VL comprising the amino acid sequence of SEQ ID NO: 9, SEQ ID NO: 13, SEQ ID NO: 17; or humanized versions thereof. In some embodiments, the Centrin-1 IgG1 antibody comprises a VH comprising the amino acid sequence of SEQ ID NO: 1, SEQ ID NO: 5, or humanized versions thereof; and comprises a VL comprising the amino acid sequence of SEQ ID NO: 9, SEQ ID NO: 13, SEQ ID NO: 17; or humanized versions thereof.

In some embodiments, the VH of the Centrin-1 IgG1 antibody comprises any one or more of the HCDRs listed in Table 1b. In exemplary embodiments, the VH of the Centrin-1 IgG1 antibody comprises a HCDR1 comprising SEQ ID NO. 2, SEQ ID NO. 40, SEQ ID NO. 6 or SEQ ID NO. 43; a HCDR2 comprising SEQ ID NO. 3, SEQ ID NO. 41, SEQ ID NO. 7, or SEQ ID NO. 44; and/or an HCDR3 comprising SEQ ID NO. 4, SEQ ID NO. 42, SEQ ID NO. 8 or SEQ ID NO. 45.

In some embodiments, the VL of the Centrin-1 IgG1 antibody comprises any one or more of the LCDRs listed in Table 1b. In exemplary embodiments, the VL of the Centrin-1 IgG1 antibody comprises an LCDR1 comprising SEQ ID NO. 10, SEQ ID NO. 46, SEQ ID NO. 47, SEQ ID NO. 14, SEQ ID NO. 50, SEQ ID NO. 51, SEQ ID NO. 18 or SEQ ID NO. 54; an LCDR2 comprising SEQ ID NO. 11, SEQ ID NO. 48, SEQ ID NO. 15, or SEQ ID NO. 52, SEQ ID NO. 19, or SEQ ID NO. 55; and/or an LCDR3 comprising SEQ ID NO. 12, SEQ ID NO. 49, SEQ ID NO. 16, SEQ ID NO. 53, SEQ ID NO. 20 or SEQ ID NO. 56.

In some embodiments, the VH of the Centrin-1 IgG1 antibody comprises any one or more of the HCDRs listed in Table 1b and the VL of the Centrin-1 IgG1 antibody comprises any one or more of the LCDRs listed in Table 1b.

In some embodiments, the VH of the Centrin-1 IgG1 antibody comprises a HCDR1 comprising SEQ ID NO. 2, SEQ ID NO. 40, SEQ ID NO. 6 or SEQ ID NO. 43; a HCDR2 comprising SEQ ID NO. 3, SEQ ID NO. 41, SEQ ID NO. 7, or SEQ ID NO. 44; and/or an HCDR3 comprising SEQ ID NO. 4, SEQ ID NO. 42, SEQ ID NO. 8 or SEQ ID NO. 45; and the VL of the Centrin-1 IgG1 antibody comprises an LCDR1 comprising SEQ ID NO. 10, SEQ ID NO. 46, SEQ ID NO. 47, SEQ ID NO. 14, SEQ ID NO. 50, SEQ ID NO. 51, SEQ ID NO. 18 or SEQ ID NO. 54; an LCDR2 comprising SEQ ID NO. 11, SEQ ID NO. 48, SEQ ID NO. 15, or SEQ ID NO. 52, SEQ ID NO. 19, or SEQ ID NO. 55; and/or an LCDR3 comprising SEQ ID NO. 12, SEQ ID NO. 49, SEQ ID NO. 16, SEQ ID NO. 53, SEQ ID NO. 20 or SEQ ID NO. 56.

In some embodiments, the Centrin-1 IgG1 antibody comprises HCDRs and LCDRs in any one of the combinations 1 through 6 listed in Table 1c. For example in some embodiments the Centrin-1 antibody comprises the HCDRs and the LCDRs of Combination 1 of Table 1c, the Centrin-1 antibody comprises the HCDRs and the LCDRs of Combination 2 of Table 1c, the Centrin-1 antibody comprises the HCDRs and the LCDRs of Combination 3 of Table 1c, the Centrin-1 antibody comprises the HCDRs and the LCDRs of Combination 4 of Table 1c, the Centrin-1 antibody comprises the HCDRs and the LCDRs of Combination 5 of Table 1c, or the Centrin-1 antibody comprises the HCDRs and the LCDRs of Combination 6 of Table 1c.

In some embodiments, the Centrin-1 antibody is an IgM antibody.

In some embodiments, the Centrin-1 IgM antibody comprises any one of the VHs and/or any of the VLs listed in Table 1a, or humanized versions thereof. In some embodiments, the Centrin-1 IgM antibody comprises a VH comprising the amino acid sequence of SEQ ID NO: 1, SEQ ID NO: 5; or humanized versions thereof. In some embodiments, the Centrin-1 IgM antibody comprises a VL comprising the amino acid sequence of SEQ ID NO: 9, SEQ ID NO: 13, SEQ ID NO: 17; or humanized versions thereof. In some embodiments, the Centrin-1 IgM antibody comprises a VH comprising the amino acid sequence of SEQ ID NO: 1, SEQ ID NO: 5, or humanized versions thereof; and comprises a VL comprising the amino acid sequence of SEQ ID NO: 9, SEQ ID NO: 13, SEQ ID NO: 17; or humanized versions thereof.

In some embodiments, the VH of the Centrin-1 IgM antibody comprises any one or more of the HCDRs listed in Table 1b. In exemplary embodiments, the VH of the Centrin-1 IgM antibody comprises a HCDR1 comprising SEQ ID NO. 2, SEQ ID NO. 40, SEQ ID NO. 6 or SEQ ID NO. 43; a HCDR2 comprising SEQ ID NO. 3, SEQ ID NO. 41, SEQ ID NO. 7, or SEQ ID NO. 44; and/or an HCDR3 comprising SEQ ID NO. 4, SEQ ID NO. 42, SEQ ID NO. 8 or SEQ ID NO. 45.

In some embodiments, the VL of the Centrin-1 IgM antibody comprises any one or more of the LCDRs listed in Table 1b. In exemplary embodiments, the VL of the Centrin-1 IgM antibody comprises an LCDR1 comprising SEQ ID NO. 10, SEQ ID NO. 46, SEQ ID NO. 47, SEQ ID NO. 14, SEQ ID NO. 50, SEQ ID NO. 51, SEQ ID NO. 18 or SEQ ID NO. 54; an LCDR2 comprising SEQ ID NO. 11, SEQ ID NO. 48, SEQ ID NO. 15, or SEQ ID NO. 52, SEQ ID NO. 19, or SEQ ID NO. 55; and/or an LCDR3 comprising SEQ ID NO. 12, SEQ ID NO. 49, SEQ ID NO. 16, SEQ ID NO. 53, SEQ ID NO. 20 or SEQ ID NO. 56.

In some embodiments, the VH of the Centrin-1 IgM antibody comprises any one or more of the HCDRs listed in Table 1b and the VL of the Centrin-1 IgM antibody comprises any one or more of the LCDRs listed in Table 1b.

In some embodiments, the VH of the Centrin-1 IgM antibody comprises a HCDR1 comprising SEQ ID NO. 2, SEQ ID NO. 40, SEQ ID NO. 6 or SEQ ID NO. 43; a HCDR2 comprising SEQ ID NO. 3, SEQ ID NO. 41, SEQ ID NO. 7, or SEQ ID NO. 44; and/or an HCDR3 comprising SEQ ID NO. 4, SEQ ID NO. 42, SEQ ID NO. 8 or SEQ ID NO. 45; and the VL of the Centrin-1 IgM antibody comprises an LCDR1 comprising SEQ ID NO. 10, SEQ ID NO. 46, SEQ ID NO. 47, SEQ ID NO. 14, SEQ ID NO. 50, SEQ ID NO. 51, SEQ ID NO. 18 or SEQ ID NO. 54; an LCDR2 comprising SEQ ID NO. 11, SEQ ID NO. 48, SEQ ID NO. 15, or SEQ ID NO. 52, SEQ ID NO. 19, or SEQ ID NO. 55; and/or an LCDR3 comprising SEQ ID NO. 12, SEQ ID NO. 49, SEQ ID NO. 16, SEQ ID NO. 53, SEQ ID NO. 20 or SEQ ID NO. 56.

In some embodiments, the Centrin-1 IgM antibody comprises HCDRs and LCDRs in any one of the combinations 1 through 6 listed in Table 1c. For example in some embodiments the Centrin-1 antibody comprises the HCDRs and the LCDRs of Combination 1 of Table 1c, the Centrin-1 antibody comprises the HCDRs and the LCDRs of Combination 2 of Table 1c, the Centrin-1 antibody comprises the HCDRs and the LCDRs of Combination 3 of Table 1c, the Centrin-1 antibody comprises the HCDRs and the LCDRs of Combination 4 of Table 1c, the Centrin-1 antibody comprises the HCDRs and the LCDRs of Combination 5 of Table 1c, or the Centrin-1 antibody comprises the HCDRs and the LCDRs of Combination 6 of Table 1c.

The antibodies provided herein are specific for Centrin-1 from any mammalian and non-mammalian species. In some embodiments, the Centrin-1 antibody is specific for human Centrin-1. In some embodiments, the Centrin-1 antibody is cross reactive with Centrin-1 from other species. In some embodiments, the Centrin-1 antibody is cross reactive with a human Centrin-1 and a non-human primate Centrin-1. In some embodiments, the Centrin-1 antibody is cross reactive with a human Centrin-1 and a cynomologous monkey Centrin-1.

The antibodies provided herein bind Centrin-1 with selectivity and specificity. The Centrin-1 antibodies provided herein exhibit reduced, little, or no binding to Centrin-2. The Centrin-1 antibodies provided herein bind Centrin-1 with a greater binding affinity than they bind Centrin-2. In some embodiments, the Centrin-1 antibody binds Centrin-1 with at least a 1.5-fold, 2-fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5 fold, 9-fold, 9.5-fold, 10-fold, 15-fold, 20-fold, 25-fold, 30-fold, 35-fold, 40-fold, 45-fold, 50-fold, 55-fold, 60-fold, 65-fold, 70-fold, 75-fold, 80-fold, 85 fold, 90-fold, 95-fold, or even 100-fold greater binding affinity than to Centrin-2. In some embodiments, a Centrin-1 antibody is affinity matured.

In certain embodiments, the Centrin-1 antibody provided herein has a dissociation constant (Kd) in the range of about 0.1 pM to about 1 µM, inclusive of all values and subranges therebetween. That is, in certain embodiments, the Centrin-1 antibody provided herein may have a dissociation constant (Kd) of about 0.1 pM, about 0.5 pM, about 1 pM, about 5 pM, about 10 pM, about 20 pM, about 30 pM, about 40 pM, about 50 pM, about 60 pM, about 70 pM, about 80 pM, about 90 pM, about 100 pM, about 200 pM, about 300 pM, about 400 pM, about 500 pM, about 600 pM, about 700 pM, about 800 pM, about 900 pM, about 1 nM, about 5 nM, about 10 nM, about 20 nM, about 30 nM, about 40 nM, about 50 nM, about 60 nM, about 70 nM, about 80 nM, about 90 nM, about 100 nM, about 200 nM, about 300 nM, about 400 nM, about 500 nM, about 1 µM, or any value therebetween.

In some embodiments, the antibodies selectively bind a Centrin-1 epitope, wherein the epitope comprises a peptide sequence represented by any one of the SEQ ID NOs provided in Table 2.

In some embodiments, the antibodies selectively bind a Centrin-1 epitope, wherein the epitope comprises any one of the epitopes presented in Table 2. In some embodiments, the antibodies selectively bind a Centrin-1 epitope, wherein the epitope comprises any one of the epitopes presented selected from the group consisting of SEQ ID NO: 21-39.

TABLE 2

Centrin-1 Epitopes

| SEQ ID NO: | Epitope Sequence |
|---|---|
| SEQ ID NO: 21 | KPSAASTGQKRKVAP |
| SEQ ID NO: 22 | KPSAASTGQKRKVA |
| SEQ ID NO: 23 | KPSAASTGQKRKV |

TABLE 2-continued

Centrin-1 Epitopes

| SEQ ID NO: | Epitope Sequence |
|---|---|
| SEQ ID NO: 24 | KPSAASTGQKRK |
| SEQ ID NO: 25 | KPSAASTGQKR |
| SEQ ID NO: 26 | KPSAASTGQK |
| SEQ ID NO: 27 | KPSAASTGQ |
| SEQ ID NO: 28 | KPSAASTG |
| SEQ ID NO: 29 | KPSAAST |
| SEQ ID NO: 30 | KPSAAS |
| SEQ ID NO: 31 | PSAASTGQKRKVAP |
| SEQ ID NO: 32 | SAASTGQKRKVAP |
| SEQ ID NO: 33 | AASTGQKRKVAP |
| SEQ ID NO: 34 | ASTGQKRKVAP |
| SEQ ID NO: 35 | STGQKRKVAP |
| SEQ ID NO: 36 | TGQKRKVAP |
| SEQ ID NO: 37 | GQKRKVAP |
| SEQ ID NO: 38 | QKRKVAP |
| SEQ ID NO: 39 | KRKVAP |

Conjugated Centrin-1 Antibodies

In some embodiments, any one of the Centrin-1 antibodies disclosed herein is conjugated for a variety of purposes including, but not limited to, for use in therapeutics, detection, diagnostics, visualization, quantification, cell sorting, and for use in biological assays. Any one of the antibodies described above can be conjugated.

In some embodiments, the Centrin-1 antibody that is conjugated comprises any one of the VHs and/or any of the VLs listed in Table 1a, or humanized versions thereof. In some embodiments, the Centrin-1 antibody that is conjugated comprises a VH comprising the amino acid sequence of SEQ ID NO: 1, SEQ ID NO: 5; or humanized versions thereof. In some embodiments, the Centrin-1 antibody that is conjugated comprises a VL comprising the amino acid sequence of SEQ ID NO: 9, SEQ ID NO: 13, SEQ ID NO: 17; or humanized versions thereof. In some embodiments, the Centrin-1 antibody that is conjugated comprises a VH comprising the amino acid sequence of SEQ ID NO: 1, SEQ ID NO: 5, or humanized versions thereof; and comprises a VL comprising the amino acid sequence of SEQ ID NO: 9, SEQ ID NO: 13, SEQ ID NO: 17; or humanized versions thereof.

In some embodiments, the VH of the conjugated Centrin-1 antibody comprises any one or more of the HCDRs listed in Table 1b. In exemplary embodiments, the VH of the conjugated Centrin-1 antibody comprises a HCDR1 comprising SEQ ID NO. 2, SEQ ID NO. 40, SEQ ID NO. 6 or SEQ ID NO. 43; a HCDR2 comprising SEQ ID NO. 3, SEQ ID NO. 41, SEQ ID NO. 7, or SEQ ID NO. 44; and/or an HCDR3 comprising SEQ ID NO. 4, SEQ ID NO. 42, SEQ ID NO. 8 or SEQ ID NO. 45.

In some embodiments, the VL of the conjugated Centrin-1 antibody comprises any one or more of the LCDRs listed in Table 1b. In exemplary embodiments, the VL of the conjugated Centrin-1 antibody comprises an LCDR1 comprising SEQ ID NO. 10, SEQ ID NO. 46, SEQ ID NO. 47, SEQ ID NO. 14, SEQ ID NO. 50, SEQ ID NO. 51, SEQ ID NO. 18 or SEQ ID NO. 54; an LCDR2 comprising SEQ ID NO. 11, SEQ ID NO. 48, SEQ ID NO. 15, or SEQ ID NO. 52, SEQ ID NO. 19, or SEQ ID NO. 55; and/or an LCDR3 comprising SEQ ID NO. 12, SEQ ID NO. 49, SEQ ID NO. 16, SEQ ID NO. 53, SEQ ID NO. 20 or SEQ ID NO. 56.

In some embodiments, the VH of the conjugated Centrin-1 antibody comprises any one or more of the HCDRs listed in Table 1b and the VL of the conjugated Centrin-1 antibody comprises any one or more of the LCDRs listed in Table 1b.

In some embodiments, the VH of the conjugated Centrin-1 antibody comprises a HCDR1 comprising SEQ ID NO. 2, SEQ ID NO. 40, SEQ ID NO. 6 or SEQ ID NO. 43; a HCDR2 comprising SEQ ID NO. 3, SEQ ID NO. 41, SEQ ID NO. 7, or SEQ ID NO. 44; and/or an HCDR3 comprising SEQ ID NO. 4, SEQ ID NO. 42, SEQ ID NO. 8 or SEQ ID NO. 45; and the VL of the conjugated Centrin-1 antibody comprises an LCDR1 comprising SEQ ID NO. 10, SEQ ID NO. 46, SEQ ID NO. 47, SEQ ID NO. 14, SEQ ID NO. 50, SEQ ID NO. 51, SEQ ID NO. 18 or SEQ ID NO. 54; an LCDR2 comprising SEQ ID NO. 11, SEQ ID NO. 48, SEQ ID NO. 15, or SEQ ID NO. 52, SEQ ID NO. 19, or SEQ ID NO. 55; and/or an LCDR3 comprising SEQ ID NO. 12, SEQ ID NO. 49, SEQ ID NO. 16, SEQ ID NO. 53, SEQ ID NO. 20 or SEQ ID NO. 56.

In some embodiments, the conjugated Centrin-1 antibody comprises HCDRs and LCDRs in any one of the combinations 1 through 6 listed in Table 1c. For example in some embodiments the Centrin-1 antibody comprises the HCDRs and the LCDRs of Combination 1 of Table 1c, the Centrin-1 antibody comprises the HCDRs and the LCDRs of Combination 2 of Table 1c, the Centrin-1 antibody comprises the HCDRs and the LCDRs of Combination 3 of Table 1c, the Centrin-1 antibody comprises the HCDRs and the LCDRs of Combination 4 of Table 1c, the Centrin-1 antibody comprises the HCDRs and the LCDRs of Combination 5 of Table 1c, or the Centrin-1 antibody comprises the HCDRs and the LCDRs of Combination 6 of Table 1c.

In some embodiments, the Centrin-1 antibody is conjugated to an agent including, but not limited to, a radionuclide (also referred to as a radioactive nuclide, radioisotope or radioactive isotope), a small molecule drug (e.g. a cytotoxic chemotherapeutic agent or a signaling pathway inhibitor)), an enzyme, a detectable agent, a cytokine, a hormonal agent, an immunotherapy agent, an oligonucleotide, a second antibody, or an antibody fragment. In some embodiments, the antibody is conjugated to one or more equivalents of the agent.

In some exemplary embodiments, the, the Centrin-1 antibody is conjugated to a radionuclide. The choice of the particular radionuclide with which the Centrin-1 antibody is conjugated may be determined by the size of the cancer tumor to be treated and its localization in the body, taking into consideration the emission range in the tissue and half-life. Radionuclides include alpha emitters, beta emitters, and positron emitters. In different embodiments, the dose of the radionuclide for therapeutic purposes is between 0.1-500 mCi. Exemplary radionuclides include but are not limited to alpha emitters, beta emitters, and positron emitters.

Examples of alpha emitters include: 213-Bismuth (half-life 46 minutes), 223-Radium (half-life 11.3 days), 224-Radium (half-life 3.7 days), 225-Radium (half-life 14.8 days), 225-Actinium (half life 10 days), 212-Lead (half-life 10.6 hours), 212-Bismuth (half-life 60 minutes), 211-Astatin (half-life 7.2 hours), 255-Fermium (half-life 20 hours) and 227-Thorium (half-life 18.7 days).

Examples of beta emitters include: 188-Rhenium (half-life 16.7 hours), 90-Yttrium (half-life 2.7 days), 32-Phosphorous (half-life 14.3 days), 47-Scandium (half-life 3.4 days), 67-Copper (half-life 62 hours), 64-Copper (half-life 13 hours), 77-Arsenic (half-life 38.8 hours), 89-Strontium (half-life 51 days), 105-Rhodium (half-life 35 hours), 109-Palladium (half-life 13 hours), 111-Silver (half-life 7.5 days), 131 Iodine (half-life 8 days), 177-Lutetium (half-life 6.7 days), 153-Samarium (half-life 46.7 hours), 159-Gadolinium (half-life 18.6 hours), 186-Rhenium (half-life 3.7 days), 166-Holmium (half-life 26.8 hours), 166-Dysprosium (half-life 81.6 hours), 140-Lantanum (half-life 40.3 hours), 194-Irridium (half-life 19 hours), 198-Gold (half-life 2.7 days), and 199 Gold (half-life 3.1 days).

Examples of positron emitters include (half-life in parenthesis): 52Mn (21.1 min); 62Cu (9.74 min); 68Ga (68.1 min); 11C (20 min); 82Rb (1.27 min); 1 10In (1.15 h); 118Sb (3.5 min); 122I (3.63 min); 18F (1.83 h); 34'" Cl (32.2 min); 38K (7.64 min); 51Mn (46.2 min); 52Mn (5.59 days); 52Fe (8.28 h); 55Co (17.5 h); 61Cu (3.41 h); 64Cu (12.7 h); 72As (1.08 days); 75Br (1.62 h); 76Br (16.2 h); 82'" Rb (6.47 h); 83Sr (1.35 days); 86Y (14.7 h); 89Zr (3.27 days); 94'" Tc (52.0 min); 120I (1.35 h); 124 I (4.18 days). 64-Copper is a mixed positron, electron and Auger electron emitter.

In some exemplary embodiments, the Centrin-1 antibody is conjugated to 213-Bismuth; in other exemplary embodiments, the Centrin-1 antibody is conjugated to 213-Bismuth and is used to treat pancreatic ductal adenocarcinoma; and in other exemplary embodiments, the Centrin-1 antibody is conjugated to 213-Bismuth and is used to treat prostate cancer.

In some embodiments, the Centrin-1 antibody that is conjugated to 213-Bismuth comprises any one of the VHs and/or any of the VLs listed in Table 1a, or humanized versions thereof. In some embodiments, the Centrin-1 antibody that is conjugated to 213-Bismuth comprises a VH comprising the amino acid sequence of SEQ ID NO: 1, SEQ ID NO: 5; or humanized versions thereof. In some embodiments, the Centrin-1 antibody that is conjugated to 213-Bismuth comprises a VL comprising the amino acid sequence of SEQ ID NO: 9, SEQ ID NO: 13, SEQ ID NO: 17; or humanized versions thereof. In some embodiments, the Centrin-1 antibody that is conjugated to 213-Bismuth comprises a VH comprising the amino acid sequence of SEQ ID NO: 1, SEQ ID NO: 5, or humanized versions thereof; and comprises a VL comprising the amino acid sequence of SEQ ID NO: 9, SEQ ID NO: 13, SEQ ID NO: 17; or humanized versions thereof.

In some embodiments, the VH of the Centrin-1 antibody that is conjugated to 213-Bismuth comprises any one or more of the HCDRs listed in Table 1b. In exemplary embodiments, the VH of the Centrin-1 antibody that is conjugated to 213-Bismuth comprises a HCDR1 comprising SEQ ID NO. 2, SEQ ID NO. 40, SEQ ID NO. 6 or SEQ ID NO. 43; a HCDR2 comprising SEQ ID NO. 3, SEQ ID NO. 41, SEQ ID NO. 7, or SEQ ID NO. 44; and/or an HCDR3 comprising SEQ ID NO. 4, SEQ ID NO. 42, SEQ ID NO. 8 or SEQ ID NO. 45.

In some embodiments, the VL of the Centrin-1 antibody that is conjugated to 213-Bismuth comprises any one or more of the LCDRs listed in Table 1b. In exemplary embodiments, the VL of the Centrin-1 antibody that is conjugated to 213-Bismuth comprises an LCDR1 comprising SEQ ID NO. 10, SEQ ID NO. 46, SEQ ID NO. 47, SEQ ID NO. 14, SEQ ID NO. 50, SEQ ID NO. 51, SEQ ID NO. 18 or SEQ ID NO. 54; an LCDR2 comprising SEQ ID NO. 11, SEQ ID NO. 48, SEQ ID NO. 15, or SEQ ID NO. 52, SEQ ID NO. 19, or SEQ ID NO. 55; and/or an LCDR3 comprising SEQ ID NO. 12, SEQ ID NO. 49, SEQ ID NO. 16, SEQ ID NO. 53, SEQ ID NO. 20 or SEQ ID NO. 56.

In some embodiments, the VH of the Centrin-1 antibody that is conjugated to 213-Bismuth comprises any one or more of the HCDRs listed in Table 1b and the VL of the Centrin-1 antibody that is conjugated to 213-Bismuth comprises any one or more of the LCDRs listed in Table 1b.

In some embodiments, the VH of the Centrin-1 antibody that is conjugated to 213-Bismuth comprises a HCDR1 comprising SEQ ID NO. 2, SEQ ID NO. 40, SEQ ID NO. 6 or SEQ ID NO. 43; a HCDR2 comprising SEQ ID NO. 3, SEQ ID NO. 41, SEQ ID NO. 7, or SEQ ID NO. 44; and/or an HCDR3 comprising SEQ ID NO. 4, SEQ ID NO. 42, SEQ ID NO. 8 or SEQ ID NO. 45; and the VL of the Centrin-1 antibody that is conjugated to 213-Bismuth comprises an LCDR1 comprising SEQ ID NO. 10, SEQ ID NO. 46, SEQ ID NO. 47, SEQ ID NO. 14, SEQ ID NO. 50, SEQ ID NO. 51, SEQ ID NO. 18 or SEQ ID NO. 54; an LCDR2 comprising SEQ ID NO. 11, SEQ ID NO. 48, SEQ ID NO. 15, or SEQ ID NO. 52, SEQ ID NO. 19, or SEQ ID NO. 55; and/or an LCDR3 comprising SEQ ID NO. 12, SEQ ID NO. 49, SEQ ID NO. 16, SEQ ID NO. 53, SEQ ID NO. 20 or SEQ ID NO. 56.

In some embodiments, the Centrin-1 antibody that is conjugated to 213-Bismuth comprises HCDRs and LCDRs in any one of the combinations 1 through 6 listed in Table 1c. For example in some embodiments the Centrin-1 antibody comprises the HCDRs and the LCDRs of Combination 1 of Table 1c, the Centrin-1 antibody comprises the HCDRs and the LCDRs of Combination 2 of Table 1c, the Centrin-1 antibody comprises the HCDRs and the LCDRs of Combination 3 of Table 1c, the Centrin-1 antibody comprises the HCDRs and the LCDRs of Combination 4 of Table 1c, the Centrin-1 antibody comprises the HCDRs and the LCDRs of Combination 5 of Table 1c, or the Centrin-1 antibody comprises the HCDRs and the LCDRs of Combination 6 of Table 1c.

In some exemplary embodiments, the Centrin-1 antibody is conjugated to 177-Lutetium (177Lu); in other exemplary embodiments, the Centrin-1 antibody is conjugated to 177Lu and is used to treat pancreatic ductal adenocarcinoma; and in other exemplary embodiments, the Centrin-1 antibody is conjugated to 177Lu and is used to treat prostate cancer.

In some embodiments, the Centrin-1 antibody that is conjugated to 177-Lutetium comprises any one of the VHs and/or any of the VLs listed in Table 1a, or humanized versions thereof. In some embodiments, the Centrin-1 antibody that is conjugated to 177-Lutetium comprises a VH comprising the amino acid sequence of SEQ ID NO: 1, SEQ ID NO: 5; or humanized versions thereof. In some embodiments, the Centrin-1 antibody that is conjugated to 177-Lutetium comprises a VL comprising the amino acid sequence of SEQ ID NO: 9, SEQ ID NO: 13, SEQ ID NO: 17; or humanized versions thereof. In some embodiments, the Centrin-1 antibody that is conjugated to 177-Lutetium comprises a VH comprising the amino acid sequence of SEQ ID NO: 1, SEQ ID NO: 5, or humanized versions thereof; and comprises a VL comprising the amino acid sequence of SEQ ID NO: 9, SEQ ID NO: 13, SEQ ID NO: 17; or humanized versions thereof.

In some embodiments, the VH of the Centrin-1 antibody that is conjugated to 177-Lutetium comprises any one or more of the HCDRs listed in Table 1b. In exemplary embodiments, the VH of the Centrin-1 antibody that is conjugated to 177-Lutetium comprises a HCDR1 comprising SEQ ID NO. 2, SEQ ID NO. 40, SEQ ID NO. 6 or SEQ ID NO. 43; a HCDR2 comprising SEQ ID NO. 3, SEQ ID NO. 41, SEQ ID NO. 7, or SEQ ID NO. 44; and/or an HCDR3 comprising SEQ ID NO. 4, SEQ ID NO. 42, SEQ ID NO. 8 or SEQ ID NO. 45.

In some embodiments, the VL of the Centrin-1 antibody that is conjugated to 177-Lutetium comprises any one or more of the LCDRs listed in Table 1b. In exemplary embodiments, the VL of the Centrin-1 antibody that is conjugated to 177-Lutetium comprises an LCDR1 comprising SEQ ID NO. 10, SEQ ID NO. 46, SEQ ID NO. 47, SEQ ID NO. 14, SEQ ID NO. 50, SEQ ID NO. 51, SEQ ID NO. 18 or SEQ ID NO. 54; an LCDR2 comprising SEQ ID NO. 11, SEQ ID NO. 48, SEQ ID NO. 15, or SEQ ID NO. 52, SEQ ID NO. 19, or SEQ ID NO. 55; and/or an LCDR3 comprising SEQ ID NO. 12, SEQ ID NO. 49, SEQ ID NO. 16, SEQ ID NO. 53, SEQ ID NO. 20 or SEQ ID NO. 56.

In some embodiments, the VH of the Centrin-1 antibody that is conjugated to 177-Lutetium comprises any one or more of the HCDRs listed in Table 1b and the VL of the Centrin-1 antibody that is conjugated to 177-Lutetium comprises any one or more of the LCDRs listed in Table 1b.

In some embodiments, the VH of the Centrin-1 antibody that is conjugated to 177-Lutetium comprises a HCDR1 comprising SEQ ID NO. 2, SEQ ID NO. 40, SEQ ID NO. 6 or SEQ ID NO. 43; a HCDR2 comprising SEQ ID NO. 3, SEQ ID NO. 41, SEQ ID NO. 7, or SEQ ID NO. 44; and/or an HCDR3 comprising SEQ ID NO. 4, SEQ ID NO. 42, SEQ ID NO. 8 or SEQ ID NO. 45; and the VL of the Centrin-1 antibody that is conjugated to 177-Lutetium comprises an LCDR1 comprising SEQ ID NO. 10, SEQ ID NO. 46, SEQ ID NO. 47, SEQ ID NO. 14, SEQ ID NO. 50, SEQ ID NO. 51, SEQ ID NO. 18 or SEQ ID NO. 54; an LCDR2 comprising SEQ ID NO. 11, SEQ ID NO. 48, SEQ ID NO. 15, or SEQ ID NO. 52, SEQ ID NO. 19, or SEQ ID NO. 55; and/or an LCDR3 comprising SEQ ID NO. 12, SEQ ID NO. 49, SEQ ID NO. 16, SEQ ID NO. 53, SEQ ID NO. 20 or SEQ ID NO. 56.

In some embodiments, the Centrin-1 antibody that is conjugated to 177-Lutetium comprises HCDRs and LCDRs in any one of the combinations 1 through 6 listed in Table 1c. For example in some embodiments the Centrin-1 antibody comprises the HCDRs and the LCDRs of Combination 1 of Table 1c, the Centrin-1 antibody comprises the HCDRs and the LCDRs of Combination 2 of Table 1c, the Centrin-1 antibody comprises the HCDRs and the LCDRs of Combination 3 of Table 1c, the Centrin-1 antibody comprises the HCDRs and the LCDRs of Combination 4 of Table 1c, the Centrin-1 antibody comprises the HCDRs and the LCDRs of Combination 5 of Table 1c, or the Centrin-1 antibody comprises the HCDRs and the LCDRs of Combination 6 of Table 1c.

In some exemplary embodiments, the Centrin-1 antibody is conjugated to 212-Lead (212Pb); in other exemplary embodiments, the Centrin-1 antibody is conjugated to 212Pb and is used to treat pancreatic ductal adenocarcinoma; and in other exemplary embodiments, the Centrin-1 antibody is conjugated to 212Pb and is used to treat prostate cancer.

In some embodiments, the Centrin-1 antibody that is conjugated to 212-Lead comprises any one of the VHs and/or any of the VLs listed in Table 1a, or humanized versions thereof. In some embodiments, the Centrin-1 antibody that is conjugated to 212-Lead comprises a VH comprising the amino acid sequence of SEQ ID NO: 1, SEQ ID NO: 5; or humanized versions thereof. In some embodiments, the Centrin-1 antibody that is conjugated to 212-Lead comprises a VL comprising the amino acid sequence of SEQ ID NO: 9, SEQ ID NO: 13, SEQ ID NO: 17; or humanized versions thereof. In some embodiments, the Centrin-1 antibody that is conjugated to 212-Lead comprises a VH comprising the amino acid sequence of SEQ ID NO: 1, SEQ ID NO: 5, or humanized versions thereof; and comprises a VL comprising the amino acid sequence of SEQ ID NO: 9, SEQ ID NO: 13, SEQ ID NO: 17; or humanized versions thereof.

In some embodiments, the VH of the Centrin-1 antibody that is conjugated to 212-Lead comprises any one or more of the HCDRs listed in Table 1b. In exemplary embodiments, the VH of the Centrin-1 antibody that is conjugated to 212-Lead comprises a HCDR1 comprising SEQ ID NO. 2, SEQ ID NO. 40, SEQ ID NO. 6 or SEQ ID NO. 43; a HCDR2 comprising SEQ ID NO. 3, SEQ ID NO. 41, SEQ ID NO. 7, or SEQ ID NO. 44; and/or an HCDR3 comprising SEQ ID NO. 4, SEQ ID NO. 42, SEQ ID NO. 8 or SEQ ID NO. 45.

In some embodiments, the VL of the Centrin-1 antibody that is conjugated to 212-Lead comprises any one or more of the LCDRs listed in Table 1b. In exemplary embodiments, the VL of the Centrin-1 antibody that is conjugated to 212-Lead comprises an LCDR1 comprising SEQ ID NO. 10, SEQ ID NO. 46, SEQ ID NO. 47, SEQ ID NO. 14, SEQ ID NO. 50, SEQ ID NO. 51, SEQ ID NO. 18 or SEQ ID NO. 54; an LCDR2 comprising SEQ ID NO. 11, SEQ ID NO. 48, SEQ ID NO. 15, or SEQ ID NO. 52, SEQ ID NO. 19, or SEQ ID NO. 55; and/or an LCDR3 comprising SEQ ID NO. 12, SEQ ID NO. 49, SEQ ID NO. 16, SEQ ID NO. 53, SEQ ID NO. 20 or SEQ ID NO. 56.

In some embodiments, the VH of the Centrin-1 antibody that is conjugated to 212-Lead comprises any one or more of the HCDRs listed in Table 1b and the VL of the Centrin-1 antibody that is conjugated to 212-Lead comprises any one or more of the LCDRs listed in Table 1b.

In some embodiments, the VH of the Centrin-1 antibody that is conjugated to 212-Lead comprises a HCDR1 comprising SEQ ID NO. 2, SEQ ID NO. 40, SEQ ID NO. 6 or SEQ ID NO. 43; a HCDR2 comprising SEQ ID NO. 3, SEQ ID NO. 41, SEQ ID NO. 7, or SEQ ID NO. 44; and/or an HCDR3 comprising SEQ ID NO. 4, SEQ ID NO. 42, SEQ ID NO. 8 or SEQ ID NO. 45; and the VL of the Centrin-1 antibody that is conjugated to 212-Lead comprises an LCDR1 comprising SEQ ID NO. 10, SEQ ID NO. 46, SEQ ID NO. 47, SEQ ID NO. 14, SEQ ID NO. 50, SEQ ID NO. 51, SEQ ID NO. 18 or SEQ ID NO. 54; an LCDR2 comprising SEQ ID NO. 11, SEQ ID NO. 48, SEQ ID NO. 15, or SEQ ID NO. 52, SEQ ID NO. 19, or SEQ ID NO. 55; and/or an LCDR3 comprising SEQ ID NO. 12, SEQ ID NO. 49, SEQ ID NO. 16, SEQ ID NO. 53, SEQ ID NO. 20 or SEQ ID NO. 56.

In some embodiments, the Centrin-1 antibody that is conjugated to 212-Lead comprises HCDRs and LCDRs in any one of the combinations 1 through 6 listed in Table 1c. For example in some embodiments the Centrin-1 antibody comprises the HCDRs and the LCDRs of Combination 1 of Table 1c, the Centrin-1 antibody comprises the HCDRs and the LCDRs of Combination 2 of Table 1c, the Centrin-1 antibody comprises the HCDRs and the LCDRs of Combination 3 of Table 1c, the Centrin-1 antibody comprises the HCDRs and the LCDRs of Combination 4 of Table 1c, the Centrin-1 antibody comprises the HCDRs and the LCDRs of Combination 5 of Table 1c, or the Centrin-1 antibody comprises the HCDRs and the LCDRs of Combination 6 of Table 1c.

In some exemplary embodiments, the Centrin-1 antibody is conjugated to 225 Actinium; in other exemplary embodiments, the Centrin-1 antibody is conjugated to 225 Actinium and is used to treat pancreatic ductal adenocarcinoma; and in other exemplary embodiments, the Centrin-1 antibody is conjugated to 225 Actinium and is used to treat prostate cancer.

In some embodiments, the Centrin-1 antibody that is conjugated to 225 Actinium comprises any one of the VHs and/or any of the VLs listed in Table 1a, or humanized versions thereof. In some embodiments, the Centrin-1 antibody that is conjugated to 225 Actinium comprises a VH comprising the amino acid sequence of SEQ ID NO: 1, SEQ ID NO: 5; or humanized versions thereof. In some embodiments, the Centrin-1 antibody that is conjugated to 225 Actinium comprises a VL comprising the amino acid sequence of SEQ ID NO: 9, SEQ ID NO: 13, SEQ ID NO: 17; or humanized versions thereof. In some embodiments, the Centrin-1 antibody that is conjugated to 225 Actinium comprises a VH comprising the amino acid sequence of SEQ ID NO: 1, SEQ ID NO: 5, or humanized versions thereof; and comprises a VL comprising the amino acid sequence of SEQ ID NO: 9, SEQ ID NO: 13, SEQ ID NO: 17; or humanized versions thereof.

In some embodiments, the VH of the Centrin-1 antibody that is conjugated to 225 Actinium comprises any one or more of the HCDRs listed in Table 1b. In exemplary embodiments, the VH of the Centrin-1 antibody that is conjugated to 225 Actinium comprises a HCDR1 comprising SEQ ID NO. 2, SEQ ID NO. 40, SEQ ID NO. 6 or SEQ ID NO. 43; a HCDR2 comprising SEQ ID NO. 3, SEQ ID NO. 41, SEQ ID NO. 7, or SEQ ID NO. 44; and/or an HCDR3 comprising SEQ ID NO. 4, SEQ ID NO. 42, SEQ ID NO. 8 or SEQ ID NO. 45.

In some embodiments, the VL of the Centrin-1 antibody that is conjugated to 225 Actinium comprises any one or more of the LCDRs listed in Table 1b. In exemplary embodiments, the VL of the Centrin-1 antibody that is conjugated to 225 Actinium comprises an LCDR1 comprising SEQ ID NO. 10, SEQ ID NO. 46, SEQ ID NO. 47, SEQ ID NO. 14, SEQ ID NO. 50, SEQ ID NO. 51, SEQ ID NO. 18 or SEQ ID NO. 54; an LCDR2 comprising SEQ ID NO. 11, SEQ ID NO. 48, SEQ ID NO. 15, or SEQ ID NO. 52, SEQ ID NO. 19, or SEQ ID NO. 55; and/or an LCDR3 comprising SEQ ID NO. 12, SEQ ID NO. 49, SEQ ID NO. 16, SEQ ID NO. 53, SEQ ID NO. 20 or SEQ ID NO. 56.

In some embodiments, the VH of the Centrin-1 antibody that is conjugated to 225 Actinium comprises any one or more of the HCDRs listed in Table 1b and the VL of the Centrin-1 antibody that is conjugated to 225 Actinium comprises any one or more of the LCDRs listed in Table 1b.

In some embodiments, the VH of the Centrin-1 antibody that is conjugated to 225 Actinium comprises a HCDR1 comprising SEQ ID NO. 2, SEQ ID NO. 40, SEQ ID NO. 6 or SEQ ID NO. 43; a HCDR2 comprising SEQ ID NO. 3, SEQ ID NO. 41, SEQ ID NO. 7, or SEQ ID NO. 44; and/or an HCDR3 comprising SEQ ID NO. 4, SEQ ID NO. 42, SEQ ID NO. 8 or SEQ ID NO. 45; and the VL of the Centrin-1 antibody that is conjugated to 225 Actinium comprises an LCDR1 comprising SEQ ID NO. 10, SEQ ID NO. 46, SEQ ID NO. 47, SEQ ID NO. 14, SEQ ID NO. 50, SEQ ID NO. 51, SEQ ID NO. 18 or SEQ ID NO. 54; an LCDR2 comprising SEQ ID NO. 11, SEQ ID NO. 48, SEQ ID NO. 15, or SEQ ID NO. 52, SEQ ID NO. 19, or SEQ ID NO. 55; and/or an LCDR3 comprising SEQ ID NO. 12, SEQ ID NO. 49, SEQ ID NO. 16, SEQ ID NO. 53, SEQ ID NO. 20 or SEQ ID NO. 56.

In some embodiments, the Centrin-1 antibody that is conjugated to 225 Actinium comprises HCDRs and LCDRs in any one of the combinations 1 through 6 listed in Table 1c. For example in some embodiments the Centrin-1 antibody comprises the HCDRs and the LCDRs of Combination 1 of Table 1c, the Centrin-1 antibody comprises the HCDRs and the LCDRs of Combination 2 of Table 1c, the Centrin-1 antibody comprises the HCDRs and the LCDRs of Combination 3 of Table 1c, the Centrin-1 antibody comprises the HCDRs and the LCDRs of Combination 4 of Table 1c, the Centrin-1 antibody comprises the HCDRs and the LCDRs of Combination 5 of Table 1c, or the Centrin-1 antibody comprises the HCDRs and the LCDRs of Combination 6 of Table 1c.

In some exemplary embodiments, the Centrin-1 antibody is conjugated to 227-Thorium; in other exemplary embodiments, the Centrin-1 antibody is conjugated to 227-Thorium and is used to treat pancreatic ductal adenocarcinoma; and in other exemplary embodiments, the Centrin-1 antibody is conjugated to 227-Thorium and is used to treat prostate cancer.

In some embodiments, the Centrin-1 antibody that is conjugated to 227-Thorium comprises any one of the VHs and/or any of the VLs listed in Table 1a, or humanized versions thereof. In some embodiments, the Centrin-1 antibody that is conjugated to 227-Thorium comprises a VH comprising the amino acid sequence of SEQ ID NO: 1, SEQ ID NO: 5; or humanized versions thereof. In some embodiments, the Centrin-1 antibody that is conjugated to 227-Thorium comprises a VL comprising the amino acid sequence of SEQ ID NO: 9, SEQ ID NO: 13, SEQ ID NO: 17; or humanized versions thereof. In some embodiments, the Centrin-1 antibody that is conjugated to 227-Thorium comprises a VH comprising the amino acid sequence of SEQ ID NO: 1, SEQ ID NO: 5, or humanized versions thereof; and comprises a VL comprising the amino acid sequence of SEQ ID NO: 9, SEQ ID NO: 13, SEQ ID NO: 17; or humanized versions thereof.

In some embodiments, the VH of the Centrin-1 antibody that is conjugated to 227-Thorium comprises any one or more of the HCDRs listed in Table 1b. In exemplary embodiments, the VH of the Centrin-1 antibody that is conjugated to 227-Thorium comprises a HCDR1 comprising SEQ ID NO. 2, SEQ ID NO. 40, SEQ ID NO. 6 or SEQ ID NO. 43; a HCDR2 comprising SEQ ID NO. 3, SEQ ID NO. 41, SEQ ID NO. 7, or SEQ ID NO. 44; and/or an HCDR3 comprising SEQ ID NO. 4, SEQ ID NO. 42, SEQ ID NO. 8 or SEQ ID NO. 45.

In some embodiments, the VL of the Centrin-1 antibody that is conjugated to 227-Thorium comprises any one or more of the LCDRs listed in Table 1b. In exemplary embodiments, the VL of the Centrin-1 antibody that is conjugated to 227-Thorium comprises an LCDR1 comprising SEQ ID NO. 10, SEQ ID NO. 46, SEQ ID NO. 47, SEQ ID NO. 14, SEQ ID NO. 50, SEQ ID NO. 51, SEQ ID NO. 18 or SEQ ID NO. 54; an LCDR2 comprising SEQ ID NO. 11, SEQ ID NO. 48, SEQ ID NO. 15, or SEQ ID NO. 52, SEQ ID NO. 19, or SEQ ID NO. 55; and/or an LCDR3 comprising SEQ ID NO. 12, SEQ ID NO. 49, SEQ ID NO. 16, SEQ ID NO. 53, SEQ ID NO. 20 or SEQ ID NO. 56.

In some embodiments, the VH of the Centrin-1 antibody that is conjugated to 227-Thorium comprises any one or more of the HCDRs listed in Table 1b and the VL of the Centrin-1 antibody that is conjugated to 227-Thorium comprises any one or more of the LCDRs listed in Table 1b.

In some embodiments, the VH of the Centrin-1 antibody that is conjugated to 227-Thorium comprises a HCDR1 comprising SEQ ID NO. 2, SEQ ID NO. 40, SEQ ID NO. 6 or SEQ ID NO. 43; a HCDR2 comprising SEQ ID NO. 3, SEQ ID NO. 41, SEQ ID NO. 7, or SEQ ID NO. 44; and/or an HCDR3 comprising SEQ ID NO. 4, SEQ ID NO. 42, SEQ ID NO. 8 or SEQ ID NO. 45; and the VL of the Centrin-1 antibody that is conjugated to 227-Thorium comprises an LCDR1 comprising SEQ ID NO. 10, SEQ ID NO. 46, SEQ ID NO. 47, SEQ ID NO. 14, SEQ ID NO. 50, SEQ ID NO. 51, SEQ ID NO. 18 or SEQ ID NO. 54; an LCDR2 comprising SEQ ID NO. 11, SEQ ID NO. 48, SEQ ID NO. 15, or SEQ ID NO. 52, SEQ ID NO. 19, or SEQ ID NO. 55; and/or an LCDR3 comprising SEQ ID NO. 12, SEQ ID NO. 49, SEQ ID NO. 16, SEQ ID NO. 53, SEQ ID NO. 20 or SEQ ID NO. 56.

In some embodiments, the Centrin-1 antibody that is conjugated to 227-Thorium comprises HCDRs and LCDRs in any one of the combinations 1 through 6 listed in Table 1c. For example in some embodiments the Centrin-1 antibody comprises the HCDRs and the LCDRs of Combination 1 of Table 1c, the Centrin-1 antibody comprises the HCDRs and the LCDRs of Combination 2 of Table 1c, the Centrin-1 antibody comprises the HCDRs and the LCDRs of Combination 3 of Table 1c, the Centrin-1 antibody comprises the HCDRs and the LCDRs of Combination 4 of Table 1c, the Centrin-1 antibody comprises the HCDRs and the LCDRs of Combination 5 of Table 1c, or the Centrin-1 antibody comprises the HCDRs and the LCDRs of Combination 6 of Table 1c.

In some exemplary embodiments, the Centrin-1 antibody is conjugated to 186-Rhenium; in other exemplary embodiments, the Centrin-1 antibody is conjugated to 186-Rhenium and is used to treat pancreatic ductal adenocarcinoma; and in other exemplary embodiments, the Centrin-1 antibody is conjugated to 186-Rhenium and is used to treat prostate cancer.

In some embodiments, the Centrin-1 antibody that is conjugated to 186-Rhenium comprises any one of the VHs and/or any of the VLs listed in Table 1a, or humanized versions thereof. In some embodiments, the Centrin-1 antibody that is conjugated to 186-Rhenium comprises a VH comprising the amino acid sequence of SEQ ID NO: 1, SEQ ID NO: 5; or humanized versions thereof. In some embodiments, the Centrin-1 antibody that is conjugated to 186-Rhenium comprises a VL comprising the amino acid sequence of SEQ ID NO: 9, SEQ ID NO: 13, SEQ ID NO: 17; or humanized versions thereof. In some embodiments, the Centrin-1 antibody that is conjugated to 186-Rhenium comprises a VH comprising the amino acid sequence of SEQ ID NO: 1, SEQ ID NO: 5, or humanized versions thereof; and comprises a VL comprising the amino acid sequence of SEQ ID NO: 9, SEQ ID NO: 13, SEQ ID NO: 17; or humanized versions thereof.

In some embodiments, the VH of the Centrin-1 antibody that is conjugated to 186-Rhenium comprises any one or more of the HCDRs listed in Table 1b. In exemplary embodiments, the VH of the Centrin-1 antibody that is conjugated to 186-Rhenium comprises a HCDR1 comprising SEQ ID NO. 2, SEQ ID NO. 40, SEQ ID NO. 6 or SEQ ID NO. 43; a HCDR2 comprising SEQ ID NO. 3, SEQ ID NO. 41, SEQ ID NO. 7, or SEQ ID NO. 44; and/or an HCDR3 comprising SEQ ID NO. 4, SEQ ID NO. 42, SEQ ID NO. 8 or SEQ ID NO. 45.

In some embodiments, the VL of the Centrin-1 antibody that is conjugated to 186-Rhenium comprises any one or more of the LCDRs listed in Table 1b. In exemplary embodiments, the VL of the Centrin-1 antibody that is conjugated to 186-Rhenium comprises an LCDR1 comprising SEQ ID NO. 10, SEQ ID NO. 46, SEQ ID NO. 47, SEQ ID NO. 14, SEQ ID NO. 50, SEQ ID NO. 51, SEQ ID NO. 18 or SEQ ID NO. 54; an LCDR2 comprising SEQ ID NO. 11, SEQ ID NO. 48, SEQ ID NO. 15, or SEQ ID NO. 52, SEQ ID NO. 19, or SEQ ID NO. 55; and/or an LCDR3 comprising SEQ ID NO. 12, SEQ ID NO. 49, SEQ ID NO. 16, SEQ ID NO. 53, SEQ ID NO. 20 or SEQ ID NO. 56.

In some embodiments, the VH of the Centrin-1 antibody that is conjugated to 186-Rhenium comprises any one or more of the HCDRs listed in Table 1b and the VL of the Centrin-1 antibody that is conjugated to 186-Rhenium comprises any one or more of the LCDRs listed in Table 1b.

In some embodiments, the VH of the Centrin-1 antibody that is conjugated to 186-Rhenium comprises a HCDR1 comprising SEQ ID NO. 2, SEQ ID NO. 40, SEQ ID NO. 6 or SEQ ID NO. 43; a HCDR2 comprising SEQ ID NO. 3, SEQ ID NO. 41, SEQ ID NO. 7, or SEQ ID NO. 44; and/or an HCDR3 comprising SEQ ID NO. 4, SEQ ID NO. 42, SEQ ID NO. 8 or SEQ ID NO. 45; and the VL of the Centrin-1 antibody that is conjugated to 186-Rhenium comprises an LCDR1 comprising SEQ ID NO. 10, SEQ ID NO. 46, SEQ ID NO. 47, SEQ ID NO. 14, SEQ ID NO. 50, SEQ ID NO. 51, SEQ ID NO. 18 or SEQ ID NO. 54; an LCDR2 comprising SEQ ID NO. 11, SEQ ID NO. 48, SEQ ID NO. 15, or SEQ ID NO. 52, SEQ ID NO. 19, or SEQ ID NO. 55; and/or an LCDR3 comprising SEQ ID NO. 12, SEQ ID NO. 49, SEQ ID NO. 16, SEQ ID NO. 53, SEQ ID NO. 20 or SEQ ID NO. 56.

In some embodiments, the Centrin-1 antibody that is conjugated to 186-Rhenium comprises HCDRs and LCDRs in any one of the combinations 1 through 6 listed in Table 1c. For example in some embodiments the Centrin-1 antibody comprises the HCDRs and the LCDRs of Combination 1 of Table 1c, the Centrin-1 antibody comprises the HCDRs and the LCDRs of Combination 2 of Table 1c, the Centrin-1 antibody comprises the HCDRs and the LCDRs of Combination 3 of Table 1c, the Centrin-1 antibody comprises the HCDRs and the LCDRs of Combination 4 of Table 1c, the Centrin-1 antibody comprises the HCDRs and the LCDRs of Combination 5 of Table 1c, or the Centrin-1 antibody comprises the HCDRs and the LCDRs of Combination 6 of Table 1c.

In some exemplary embodiments, the Centrin-1 antibody is conjugated to 188-Rhenium; in other exemplary embodiments, the Centrin-1 antibody is conjugated to 188-Rhenium and is used to treat pancreatic ductal adenocarcinoma; and in other exemplary embodiments, the Centrin-1 antibody is conjugated to 188-Rhenium and is used to treat prostate cancer.

In some embodiments, the Centrin-1 antibody that is conjugated to 188-Rhenium comprises any one of the VHs and/or any of the VLs listed in Table 1a, or humanized versions thereof. In some embodiments, the Centrin-1 antibody that is conjugated to 188-Rhenium comprises a VH comprising the amino acid sequence of SEQ ID NO: 1, SEQ ID NO: 5; or humanized versions thereof. In some embodiments, the Centrin-1 antibody that is conjugated to 188-Rhenium comprises a VL comprising the amino acid sequence of SEQ ID NO: 9, SEQ ID NO: 13, SEQ ID NO: 17; or humanized versions thereof. In some embodiments, the Centrin-1 antibody that is conjugated to 188-Rhenium comprises a VH comprising the amino acid sequence of SEQ ID NO: 1, SEQ ID NO: 5, or humanized versions thereof; and comprises a VL comprising the amino acid sequence of SEQ ID NO: 9, SEQ ID NO: 13, SEQ ID NO: 17; or humanized versions thereof.

In some embodiments, the VH of the Centrin-1 antibody that is conjugated to 188-Rhenium comprises any one or more of the HCDRs listed in Table 1b. In exemplary embodiments, the VH of the Centrin-1 antibody that is conjugated to 188-Rhenium comprises a HCDR1 comprising SEQ ID NO. 2, SEQ ID NO. 40, SEQ ID NO. 6 or SEQ ID NO. 43; a HCDR2 comprising SEQ ID NO. 3, SEQ ID NO. 41, SEQ ID NO. 7, or SEQ ID NO. 44; and/or an HCDR3 comprising SEQ ID NO. 4, SEQ ID NO. 42, SEQ ID NO. 8 or SEQ ID NO. 45.

In some embodiments, the VL of the Centrin-1 antibody that is conjugated to 188-Rhenium comprises any one or more of the LCDRs listed in Table 1b. In exemplary embodiments, the VL of the Centrin-1 antibody that is conjugated to 188-Rhenium comprises an LCDR1 comprising SEQ ID NO. 10, SEQ ID NO. 46, SEQ ID NO. 47, SEQ ID NO. 14, SEQ ID NO. 50, SEQ ID NO. 51, SEQ ID NO. 18 or SEQ ID NO. 54; an LCDR2 comprising SEQ ID NO. 11, SEQ ID NO. 48, SEQ ID NO. 15, or SEQ ID NO. 52, SEQ ID NO. 19, or SEQ ID NO. 55; and/or an LCDR3 comprising SEQ ID NO. 12, SEQ ID NO. 49, SEQ ID NO. 16, SEQ ID NO. 53, SEQ ID NO. 20 or SEQ ID NO. 56.

In some embodiments, the VH of the Centrin-1 antibody that is conjugated to 188-Rhenium comprises any one or more of the HCDRs listed in Table 1b and the VL of the Centrin-1 antibody that is conjugated to 188-Rhenium comprises any one or more of the LCDRs listed in Table 1b.

In some embodiments, the VH of the Centrin-1 antibody that is conjugated to 188-Rhenium comprises a HCDR1 comprising SEQ ID NO. 2, SEQ ID NO. 40, SEQ ID NO. 6 or SEQ ID NO. 43; a HCDR2 comprising SEQ ID NO. 3, SEQ ID NO. 41, SEQ ID NO. 7, or SEQ ID NO. 44; and/or an HCDR3 comprising SEQ ID NO. 4, SEQ ID NO. 42, SEQ ID NO. 8 or SEQ ID NO. 45; and the VL of the Centrin-1 antibody that is conjugated to 188-Rhenium comprises an LCDR1 comprising SEQ ID NO. 10, SEQ ID NO. 46, SEQ ID NO. 47, SEQ ID NO. 14, SEQ ID NO. 50, SEQ ID NO. 51, SEQ ID NO. 18 or SEQ ID NO. 54; an LCDR2 comprising SEQ ID NO. 11, SEQ ID NO. 48, SEQ ID NO. 15, or SEQ ID NO. 52, SEQ ID NO. 19, or SEQ ID NO. 55; and/or an LCDR3 comprising SEQ ID NO. 12, SEQ ID NO. 49, SEQ ID NO. 16, SEQ ID NO. 53, SEQ ID NO. 20 or SEQ ID NO. 56.

In some embodiments, the Centrin-1 antibody that is conjugated to 188-Rhenium comprises HCDRs and LCDRs in any one of the combinations 1 through 6 listed in Table 1c. For example in some embodiments the Centrin-1 antibody comprises the HCDRs and the LCDRs of Combination 1 of Table 1c, the Centrin-1 antibody comprises the HCDRs and the LCDRs of Combination 2 of Table 1c, the Centrin-1 antibody comprises the HCDRs and the LCDRs of Combination 3 of Table 1c, the Centrin-1 antibody comprises the HCDRs and the LCDRs of Combination 4 of Table 1c, the Centrin-1 antibody comprises the HCDRs and the LCDRs of Combination 5 of Table 1c, or the Centrin-1 antibody comprises the HCDRs and the LCDRs of Combination 6 of Table 1c.

In other exemplary embodiments, the Centrin-1 antibody is conjugated to a detectable agent (i.e. detectable label). In some embodiments, the detectable agent is a diagnostic agent. In some embodiments, the Centrin-1 antibody is conjugated to a detectable label, a spin label, a colorimetric label, a radioactive label, an enzymatic label, a fluorescent label, or a magnetic label. Such detectable labels may be useful for imaging and diagnostics of cancer, e.g. pancreatic or prostate cancer. In some embodiments, the detection of the labels may involve qualitative evaluation, while in other embodiments, it may involve quantitative evaluation of the amount of signal present. In some embodiments, quantitative evaluation of labeled Centrin-1 antibodies in vivo may be used for detection of cancer; follow progression of cancer before, during and/or after therapy; examine the efficacy of a cancer therapy; or a combination thereof.

In some embodiments, the agent is conjugated to the Centrin-1 antibody via a linker.

In other embodiments one or more CDRs of any of the Centrin-1 antibodies described herein are conjugated to a radioisotope or detectable agent.

Production of Centrin-1 Antibodies

A variety of immunoassay formats may be used to select antibodies specifically immunoreactive with Centrin-1. For example, solid-phase immunoassays such as ELISA immunoassays may be used to select antibodies specific to Centrin-1.

Production of the antibodies provided herein may be by any method known to those with skill in the art. For example, in some embodiments, the Centrin-1 antibodies are produced by recombinant cells engineered to express the desired light chains and heavy chains of the desired antibody. In some embodiments the antibodies are produced by hybridomas. In some embodiments, any one of the Centrin-1 antibodies disclosed herein may be humanized using methods that are within the skill of the art. In some embodiments, any one of the Centrin-1 antibodies disclosed herein are chimeric antibodies, made to be chimeric using methods that are within the skill of the art.

In some embodiments, any peptide comprising the Centrin-1 antigen, optionally linked to the immunogenic carrier, is used for immunization using standard protocols. In some embodiments, a peptide comprising a portion of the Centrin-1 protein that has diverged from Centrin-2 is used for immunization. In some embodiments, a peptide comprising amino acids from the N-terminus of Centrin-1 is used for immunization. In some embodiments, a 15-amino acid residue peptide derived from the N-terminus of the Centrin 1 protein beginning at the seventh amino acid residue and comprising the sequence, KPSAASTGQKRKVAP (SEQ ID NO: 21), is used for immunization.

The quality and titer of generated antibodies may be assessed using techniques known to those in the art.

Provided herein are nucleic acid molecules encoding any one of Centrin-1 antibodies provided herein, recombinant expression vectors comprising such nucleic acids, host cells comprising such expression vectors, and methods of producing the Centrin-1 antibodies comprising growing the host cells under conditions permitting production of the antibodies, and recovering the produced antibodies.

Centrin-1 Antibodies for Therapeutic Use

Provided herein are Centrin-1 antibodies for therapeutic use, for the treatment of cancer. Generally, the therapeutic method comprising administering to a subject in need thereof a therapeutically effective amount of any one of the Centrin-1 antibodies provided herein.

In some aspects, administration of a therapeutically effective amount of any one of the Centrin-1 antibodies provided herein for a therapeutically effective time slows the growth of the tumor in the subject. In certain aspects, the methods disclosed herein result in a reduction of tumor volume associated with cancer in the subject. In some aspects, the methods disclosed herein induce elimination of cancer in the subject. In some aspects, the methods disclosed herein inhibit recurrence of cancer or regrowth of tumor in the subject. In some aspects, the methods disclosed herein inhibit recurrence of cancer or regrowth of tumor for at least 3 months, at least 6 months, at least 12 months, or at least 36 months.

In some aspects, administration of a therapeutically effective amount of any one of the Centrin-1 antibodies provided herein for a therapeutically effective time results in little, or no measurable, adverse effects on hematological parameters in the subject. Hemotological parameters include, but are not limited to, white blood cell count (cell number/mL); red blood cell count (cell number/mL); hemoglobin (Gram/DL); haematocrit (%); mean corpuscular volume (CU Microns); mean corpuscular hemoglobin (PICO Grams); mean corpuscular hemoglobin concentration (%); platelet count (cell number/mL). In some aspects, the methods disclosed herein cause no measurable hemotologic toxicity. In some aspects, the methods disclosed herein cause little or no measurable adverse effects on hematological parameters in the subject after about 1 week, about 2 weeks, about 3 weeks, about 4 weeks, about 5 weeks, about 6 weeks, about 7 weeks, about 8 weeks, about 9 weeks, about 10 weeks, about 11 weeks or about 12 weeks.

In some aspects, administration of a therapeutically effective amount of any one of the Centrin-1 antibodies provided herein for a therapeutically effective time results in little, or no measurable adverse effects on hepatic function parameters in the subject. Hepatic function parameters include, but are not limited to, concentration of aspartate transaminase (AST), alanine transaminase (ALT), alkaline phosphatase (ALP), gamma glutamyl transpeptidase (GGT) and albumin. In some aspects, the methods disclosed herein cause no measurable hepatic toxicity. In some aspects, the methods disclosed herein cause little or no measurable adverse effects on hepatic function parameters in the subject after about 1 week, about 2 weeks, about 3 weeks, about 4 weeks, about 5 weeks, about 6 weeks, about 7 weeks, about 8 weeks, about 9 weeks, about 10 weeks, about 11 weeks or about 12 weeks.

In some aspects, administration of a therapeutically effective amount of any one of the Centrin-1 antibodies provided herein for a therapeutically effective time results in little, or no measurable adverse effects on renal function parameters in the subject. Renal function parameters include, but are not limited to, concentration of urea, creatinine and urine protein. In some aspects, the methods disclosed herein cause no measurable renal toxicity. In some aspects, the methods disclosed herein cause little or no measurable adverse effects on renal function parameters in the subject after about 1 week, about 2 weeks, about 3 weeks, about 4 weeks, about 5 weeks, about 6 weeks, about 7 weeks, about 8 weeks, about 9 weeks, about 10 weeks, about 11 weeks or about 12 weeks.

As used herein, a subject refers to any animal classified as a mammal, including humans, domestic and farm animals, and zoo, sport, or pet animals, such as dogs, horses, rabbits, cattle, pigs, hamsters, gerbils, mice, ferrets, rats, cats, and the like. Subjects may be of any age, and may be male or female.

In some embodiments, the cancer is a primary cancer. In some embodiments, the cancer is a metastatic cancer.

In some embodiments, the cancer is pancreatic cancer. In some aspects, the pancreatic cancer is a pancreatic exocrine cancer. In some embodiments, the pancreatic exocrine cancer is pancreatic ductal adenocarcinoma (PDAC). In some embodiments, the pancreatic exocrine cancer is acinar cell carcinoma. In yet other aspects, the pancreatic cancer is adenosquamous carcinoma, squamous cell carcinoma, signet ring cell carcinoma, undifferentiated carcinoma or undifferentiated carcinoma with giant cells. In some embodiments, the pancreatic cancer is Grade 0, Grade 1, Grade 2, Grade 3 or Grade 4 pancreatic cancer. The grades of pancreatic cancer are further described at www.cancer.org/cancer/pancreatic-cancer/detection-diagnosis-staging/staging.html. In some embodiments, the cancer is metastasized in a subject.

In some embodiments, the cancer is prostate cancer. In some embodiments, the prostate cancer is adenocarcinoma of the prostate. In some embodiments, the prostate cancer is acinar adenocarcinoma, ductal adenocarcinoma, transitional cell or urothelial cancer, squamous cell cancer or small cell prostate cancer. In some embodiments the prostate cancer is Gleason Score 2, 3, 4, 5, 6, 7, 8, 9, or 10 adenocarcinoma of the prostate. The grades of prostate cancer are further described at www.cancerresearchuk.org/about-cancer/prostate-cancer/types-grades. In some embodiments, the cancer is metastasized in a subject.

The administration of any of the therapeutic Centrin-1 antibodies provided herein may be administered in combination with other known drugs/treatments (e.g. surgery, radiation, cytotoxic chemotherapy, molecular targeted therapy directed at growth and cell signaling pathways, hormonal therapy, immunotherapy agents, or other biologics). The administration may be sequential or concurrent.

In some embodiments, the Centrin-1 antibodies may be administered in combination with an immunotherapy (e.g. immune checkpoint inhibitors such as CTLA4, PD1, PDL-1 inhibitors; e.g. antibody-based immune checkpoint inhibitors; cell-based therapies, including using tumor infiltrating lymphocytes, dendritic cell therapies and the like).

In some embodiments, as described above, the therapeutic Centrin-1 antibody is conjugated to an agent, e.g. a small molecule drug, or a radionuclide.

In vivo administration of the therapeutic Centrin-1 antibodies described herein may be carried out intravenously, intratumorally, intracranially, intralesionally (e.g. intralesional injection, direct contact diffusion), intracavitary (intraperitoneal, intrapleural, intrauterine, intrarectal), intramuscularly, subcutaneously, topically, orally, transdermally, by implantation, by inhalation, intrathecally, intraventricularly, or intranasally. In some exemplary embodiments, the route of administration is by intravenous injection.

A therapeutically effective amount of the therapeutic antibody will be administered. The appropriate dosage of the therapeutic antibody may be determined based on the severity of the cancer, the clinical condition of the subject, the subject's clinical history and response to the treatment, and the discretion of the attending physician. In some embodiments, the therapeutically effective amount of the therapeutic antibody does not have adverse effects on off-target tissues. In some embodiments, off-target tissues are normal, non-cancerous tissues. In some embodiments, off-target tissues include, but are not limited to, non-pancreatic tissues, such as, for example, tissues of the testes.

The dosage amounts of the Centrin-1 antibodies provided herein may vary from about 1 ng/kg up to about 1000 mg/kg of a subject's body weight or more per day, depending upon the route of administration. For repeated administrations over several days or longer, depending on the severity cancer, the treatment may be sustained until a desired suppression of symptoms is achieved. Dosage regimens may be useful, depending on the pattern of pharmacokinetic decay that the physician wishes to achieve. For example, dosing an individual from one to twenty-one times a week is provided herein. In certain embodiments, dosing frequency is three times per day, twice per day, once per day, once every other day, once weekly, once every two weeks, once every four weeks, once every five weeks, once every six weeks, once every seven weeks, once every eight weeks, once every nine weeks, once every ten weeks, or once monthly, once every two months, once every three months, or longer. Progress of the therapy may be monitored by conventional techniques and assays. The dosing regimen may vary over time independently of the dose used.

Pharmaceutical Compositions

The present disclosure provides compositions comprising therapeutic Centrin-1 antibodies. The pharmaceutical compositions generally comprise an effective amount of any one of the Centrin-1 antibodies provided herein, and a pharmaceutically acceptable excipient (e.g. an excipient that can administered to a subject without causing any undesirable biological effect; has met the required standards of toxicological and manufacturing testing; is included on the Inactive Ingredient Database prepared by the U.S. Food and Drug administration).

The compositions according to the invention may comprise any additional active agent, which may be administered simultaneously, or separately, at the same time, or as different compositions (including in separate compositions that vary in dosage form, release profiles, and the like).

Centrin-1 Antibodies for Diagnostic Use

The Centrin-1 antibodies provided herein may be used for diagnostic and imaging purposes. Depending on the application, the Centrin-1 antibody may be detected and quantified in vivo or in vitro.

The Centrin-1 antibodies may be used for diagnostic purposes, either by detecting, localizing, or quantitating cancer tumor cells in suspected tissue.

The Centrin-1 antibodies provided herein are amendable for use in a variety of immunoassays, including but not limited to a western blot, immunohistochemistry, an enzyme-linked immunosorbent assay (ELISA), a radioimmunoassay (MA), flow cytometry, a radioimmunoassay, an immunofluorescence assay, spectrophotometry, radiography, high performance liquid chromatography (HPLC), or thin layer chromatography (TLC).

The Centrin-1 antibodies provided herein may be comprise a detectable label, for example detectable by spectroscopic, photochemical, biochemical, immunochemical, fluorescent, electrical, optical or chemical methods. Useful labels in the present invention include, but are not limited to fluorescent dyes, radiolabels, enzymes, colorimetric labels, avidin or biotin.

In some embodiments, the Centrin-1 antibody is attached to a solid surface, for example a bead, resin or a microplate.

In some embodiments, the Centrin-1 antibody is radiolabeled with an isotope, useful for imaging by nuclear medicine equipment (SPECT, PET, or scintigraphy).

The diagnostic Centrin-1 antibodies may be used for the diagnosis of the primary cancer, to monitor metastases, or to determine response to a treatment.

Accordingly, these anti-Centrin-1 antibodies may be used for detecting abnormal levels of Centrin-1 in tissues before the symptoms of the disease are felt by a subject, in particular in subjects who are at risk of developing pancreatic cancer or prostate cancer, are suspected of having developed pancreatic or prostate cancer, are affected by prostate or pancreatic cancer, have unknown primary cancer, or present evidence of metastatic cancer.

Generally, in one approach, diagnostic use of the Centrin-1 antibodies provided herein comprises determining that a subject has, or is at risk for developing, cancer comprising contacting a biological sample from the subject with any one of the Centrin-1 antibodies provided herein, and determining that the subject has, or is at risk for developing, cancer if the relative level of Centrin-1 is higher than a control value. Such diagnostic methods generally involve quantifying the amount of Centrin-1 in the biological samples, e.g. using an immunoassay. The control values refer to the Centrin-1 levels in reference biological samples (e.g. levels in normal subjects, baseline levels from the same individual, and the like).

In another approach, a diagnostic use of the Centrin-1 antibodies provided herein comprises determining that a subject has, or is at risk for developing, cancer comprising method of detecting a cancer in a subject comprising administering to the subject any one of the Centrin-1 antibodies provided herein, and determining that the subject has, or is at risk for developing, cancer if: the relative level of Centrin-1 is higher than a control value, e.g. by isolating and procuring a biological sample from the subject for immunological testing, or by imaging the subject following administration and noting an altered pattern of expression of Centrin-1 in the subject and/or visualizing an increase or change in Centrin-1 signal.

In other embodiments, a use of the Centrin-1 antibodies provided herein comprises monitoring a subject's response to a treatment paradigm, for prostate or pancreatic cancer; for monitoring the progression of the prostate or pancreatic cancer in a subject; for selecting subjects for treatment for prostate or pancreatic cancer; or for determining subjects who would be amenable to Centrin-1 antibody-based treatment.

In some embodiments, the subject is suspected of having prostate cancer. In some subjects the subject has tested for a high PSA value. In some subjects the subject has tested for a low PSA value.

In some embodiments, the subject is suspected of having pancreatic cancer or a pancreatic ductal adenocarcinoma.

In some embodiments, the subject has a suspected cancer of unknown primary site.

Detection and diagnostics can be carried out in any biological sample. In one aspect of the invention, the diagnosis or detection are performed in a liquid biopsy procedure. In a different aspect of the invention, the diagnosis or detection are performed on a standard tissue biopsy material. In some embodiments, a positive histochemical staining indicates the presence of pancreatic ductal adenocarcinoma (PDAC). In some embodiments, a positive histochemical staining indicates the presence of prostatic adenocarcinoma.

In some embodiments, the subject is at risk of developing, is suspected to have developed, or has developed pancreatic cancer or prostate cancer. The pancreatic cancer can be pancreatic ductal adenocarcinoma (PDAC). The prostate cancer can be adenocarcinoma of the prostate.

In some embodiments, the subject has a family history of pancreatic cancer or PDAC. In some embodiments, the subject has no family history of pancreatic cancer or PDAC. In some embodiments, the subject has a family history of prostate cancer or prostatic adenocarcinoma. In some embodiments, the subject has no family history of prostate cancer or prostatic adenocarcinoma.

In other embodiments, the method of diagnosing or detecting comprises administering a cancer treatment. Cancer treatment may include, but it is not limited to, chemotherapy, radiation, immunotherapy, surgical intervention or any combination thereof.

Centrin-1 Peptides for Diagnostic Use

Provided herein are Centrin-1 peptides capable of binding with Centrin-1 circulating autoantibodies, useful for diagnostic and imaging purposes. Such detection may be useful for the diagnostics, treatment monitoring, and assessment of a Centrin-1-related disease state, for example the pancreatic and/or prostate cancers discussed herein. Depending on the application, binding of the Centrin-1 peptide may be detected and quantified in vivo or in vitro. Table 3 provides exemplary Centrin-1 peptides.

The Centrin-1 peptides provided herein are amendable for use in a variety of immunoassays, including but not limited to a western blot, immunohistochemistry, an enzyme-linked immunosorbent assay (ELISA), a radioimmunoassay (MA), flow cytometry, a radioimmunoassay, an immunofluorescence assay, spectrophotometry, radiography, high performance liquid chromatography (HPLC), or thin layer chromatography (TLC).

The Centrin-1 peptides provided herein may be comprise a detectable label, for example detectable by spectroscopic, photochemical, biochemical, immunochemical, fluorescent, electrical, optical or chemical methods. Useful labels in the present invention include, but are not limited to fluorescent dyes, radiolabels, enzymes, colorimetric labels, avidin or biotin.

In some embodiments, the Centrin-1 peptides is attached to a solid surface, for example a bead, resin or a microplate.

In some embodiments, the Centrin-1 peptides is radiolabeled with an isotope, useful for imaging by nuclear medicine equipment (SPECT, PET, or scintigraphy).

The diagnostic Centrin-1 peptides may be used for the diagnosis of the primary cancer, to monitor metastases, or to determine response to a treatment.

Accordingly, the Centrin-1 peptides may be used for detecting abnormal levels of Centrin-1 autoantibodies in tissues before the symptoms of the disease are felt by a subject, in particular in subjects who are at risk of developing pancreatic cancer or prostate cancer, are suspected of having developed pancreatic or prostate cancer, are affected by prostate or pancreatic cancer, have unknown primary cancer, or present evidence of metastatic cancer.

Generally, in one approach, diagnostic use of the Centrin-1 peptides provided herein comprises determining that a subject has, or is at risk for developing, cancer comprising contacting a biological sample from the subject with any one of the Centrin-1 peptides provided herein, and determining that the subject has, or is at risk for developing, cancer if the relative level of Centrin-1 autoantibodies is higher than a control value. Such diagnostic methods generally involve quantifying the amount of Centrin-1 autoantibodies in the biological samples, e.g. using an immunoassay. The control values refer to the Centrin-1 autoantibody levels in reference biological samples (e.g. levels in normal subjects, baseline levels from the same individual, and the like).

In another approach, a diagnostic use of the Centrin-1 peptides provided herein comprises determining that a subject has, or is at risk for developing, cancer comprising method of detecting a cancer in a subject comprising administering to the subject any one of the Centrin-1 peptides provided herein, and determining that the subject has, or is at risk for developing, cancer if: the relative level of Centrin-1 autoantibodies is higher than a control value, e.g. by isolating and procuring a biological sample from the subject for immunological testing, or by imaging the subject following administration and noting an altered pattern of expression of Centrin-1 autoantibodies in the subject and/or visualizing an increase or change in Centrin-1 autoantibody signal.

In other embodiments, use of the Centrin-1 peptides provided herein comprises monitoring a subject's response to a treatment paradigm, for prostate or pancreatic cancer; for monitoring the progression of the prostate or pancreatic cancer in a subject; for selecting subjects for treatment for prostate or pancreatic cancer; or for determining subjects who would be amenable to treatment.

In some embodiments, the subject is suspected of having prostate cancer. In some subjects the subject has tested for a high PSA value. In some subjects the subject has tested for a low PSA value.

In some embodiments, the subject is suspected of having pancreatic cancer or a pancreatic ductal adenocarcinoma.

In some embodiments, the subject has a suspected cancer of unknown primary site.

Detection and diagnostics can be carried out in any biological sample. In one aspect of the invention, the diagnosis or detection are performed in a liquid biopsy procedure. In a different aspect of the invention, the diagnosis or detection are performed on a standard tissue biopsy material. In some embodiments, a positive histochemical staining indicates the presence of pancreatic ductal adenocarcinoma (PDAC). In some embodiments, a positive histochemical staining indicates the presence of prostatic adenocarcinoma.

In some embodiments, the subject is at risk of developing, is suspected to have developed, or has developed pancreatic cancer or prostate cancer. The pancreatic cancer can be pancreatic ductal adenocarcinoma (PDAC). The prostate cancer can be adenocarcinoma of the prostate.

In some embodiments, the subject has a family history of pancreatic cancer or PDAC. In some embodiments, the subject has no family history of pancreatic cancer or PDAC. In some embodiments, the subject has a family history of prostate cancer or prostatic adenocarcinoma. In some embodiments, the subject has no family history of prostate cancer or prostatic adenocarcinoma.

In other embodiments, the method of diagnosing or detecting comprises administering a cancer treatment. Cancer treatment may include, but it is not limited to, chemotherapy, radiation, immunotherapy, surgical intervention or any combination thereof.

TABLE 3

| Centrin-1 Peptides | |
|---|---|
| SEQ ID NO: | Epitope Sequence |
| SEQ ID NO: 21 | KPSAASTGQKRKVAP |
| SEQ ID NO: 22 | KPSAASTGQKRKVA |
| SEQ ID NO: 23 | KPSAASTGQKRKV |
| SEQ ID NO: 24 | KPSAASTGQKRK |
| SEQ ID NO: 25 | KPSAASTGQKR |
| SEQ ID NO: 26 | KPSAASTGQK |
| SEQ ID NO: 27 | KPSAASTGQ |
| SEQ ID NO: 28 | KPSAASTG |
| SEQ ID NO: 29 | KPSAAST |
| SEQ ID NO: 30 | KPSAAS |
| SEQ ID NO: 31 | PSAASTGQKRKVAP |
| SEQ ID NO: 32 | SAASTGQKRKVAP |
| SEQ ID NO: 33 | AASTGQKRKVAP |

TABLE 3-continued

| Centrin-1 Peptides | |
|---|---|
| SEQ ID NO: | Epitope Sequence |
| SEQ ID NO: 34 | ASTGQKRKVAP |
| SEQ ID NO: 35 | STGQKRKVAP |
| SEQ ID NO: 36 | TGQKRKVAP |
| SEQ ID NO: 37 | GQKRKVAP |
| SEQ ID NO: 38 | QKRKVAP |
| SEQ ID NO: 39 | KRKVAP |

Kits and Articles of Manufacture

The present application provides kits comprising a Centrin-1 antibody, e.g. for either therapeutic or diagnostic use. In some embodiments, the kits further contain a component selected from any of secondary antibodies, reagents for immunohistochemistry analysis, a pharmaceutically acceptable excipient and instruction manual and any combination thereof.

In some embodiments, the kit comprises any one or more of the therapeutic compositions described herein, with one or more pharmaceutically acceptable excipient.

The present application also provides articles of manufacture comprising any one of the therapeutic or diagnostic compositions or kits described herein. Examples of an article of manufacture include vials (e.g. sealed sterile vials).

It is to be understood that the description above as well as the examples that follow are intended to illustrate and not limit the scope of the invention. Other aspects, advantages and modifications within the scope of the invention will be apparent to those skilled in the art to which the invention pertains.

ENUMERATED EMBODIMENTS

Embodiment 1. An antibody that specifically binds Centrin-1; a monoclonal antibody that specifically binds Centrin-1; a polyclonal antibody that specifically binds Centrin-1; or an antibody that is a heterogeneous mixture of individual antibodies that bind Centrin-1. A composition comprising a homogenous mixture of Centrin-1 antibodies, wherein the mixture comprises the antibody of any one embodiments 1 to 42. A composition comprising a heterogeneous mixture of Centrin-1 antibodies, wherein the heterogeneous mixture comprises two or more antibodies of embodiments 1 to 42.

Embodiment 2. The antibody of embodiment 1, wherein the antibody binds Centrin-1 with at least a 2-fold higher binding affinity relative to its binding to Centrin-2.

Embodiment 3. The antibody of embodiment 2, wherein the antibody binds Centrin-1 with at least a 5-fold higher binding affinity relative to its binding to Centrin-2.

Embodiment 4. The antibody of embodiment 2, wherein the antibody binds Centrin-1 with at least a 7-fold higher binding affinity relative to its binding to Centrin-2.

Embodiment 5. The antibody of embodiment 1, wherein the antibody binds exhibits little or no binding to Centrin-2.

Embodiment 6. The antibody of any one of embodiments 1 to 5, wherein the antibody is an IgG isotype.

Embodiment 7. The antibody of embodiment 6, wherein the antibody is an IgG1 isotype.

Embodiment 8. The antibody of any one of embodiments 1 to 5, wherein the antibody is an IgM isotype.

Embodiment 9. The antibody of any one of embodiments 1 to 8, wherein the antibody comprises a VH and a VL, wherein the VH comprises a CDR1 comprising the amino acid sequence set forth in SEQ ID NO. 2 or SEQ ID NO: 40, a CDR2 comprising the amino acid sequence set forth in SEQ ID NO. 3 or SEQ ID NO: 41, and a CDR3 comprising the amino acid sequence set forth in SEQ ID NO. 4 or SEQ ID NO: 42; wherein the VL comprises a CDR1 comprising the amino acid sequence set forth in SEQ ID NO. 10, or SEQ ID NO: 46 or SEQ ID NO: 47, a CDR2 comprising the amino acid sequence set forth in SEQ ID NO. 11 or SEQ ID NO: 48, and a CDR3 comprising the amino acid sequence set forth in SEQ ID NO. 12 or SEQ ID NO: 49.

Embodiment 10. The antibody of any one of embodiments 1 to 8, wherein the antibody comprises a VH and a VL, wherein the VH comprises a CDR1 comprising the amino acid sequence set forth in SEQ ID NO. 2 or SEQ ID NO: 40, a CDR2 comprising the amino acid sequence set forth in SEQ ID NO. 3 or SEQ ID NO: 41, and a CDR3 comprising the amino acid sequence set forth in SEQ ID NO. 4 or SEQ ID NO: 42; and wherein the VL comprises a CDR1 comprising the amino acid sequence set forth in SEQ ID NO. 14, SEQ ID NO. 50 or SEQ ID NO. 51; a CDR2 comprising the amino acid sequence set forth in SEQ ID NO. 15 or SEQ ID NO. 52; and a CDR3 comprising the amino acid sequence set forth in SEQ ID NO. 16 or SEQ ID NO. 53.

Embodiment 11. The antibody of any one of embodiments 1 to 8, wherein the antibody comprises a VH and a VL, wherein the VH comprises a CDR1 comprising the amino acid sequence set forth in SEQ ID NO. 2 or SEQ ID NO: 40, a CDR2 comprising the amino acid sequence set forth in SEQ ID NO. 3 or SEQ ID NO: 41, and a CDR3 comprising the amino acid sequence set forth in SEQ ID NO. 4 or SEQ ID NO: 42; and wherein the VL comprises a CDR1 comprising the amino acid sequence set forth in SEQ ID NO. 18 or SEQ ID NO. 54, a CDR2 comprising the amino acid sequence set forth in SEQ ID NO. 19 or SEQ ID NO. 55, and a CDR3 comprising the amino acid sequence set forth in SEQ ID NO. 20 or SEQ ID NO. 56.

Embodiment 12. The antibody of any one of embodiments 1 to 8, wherein the antibody comprises a VH and a VL, wherein the VH comprises a CDR1 comprising the amino acid sequence set forth in SEQ ID NO. 6 or SEQ ID NO: 43, a CDR2 comprising the amino acid sequence set forth in SEQ ID NO. 7 or SEQ ID NO: 44, and a CDR3 comprising the amino acid sequence set forth in SEQ ID NO. 8 or SEQ ID NO: 45; and wherein the VL comprises a CDR1 comprising the amino acid sequence set forth in SEQ ID NO. 10, or SEQ ID NO: 46 or SEQ ID NO: 47, a CDR2 comprising the amino acid sequence set forth in SEQ ID NO. 11 or SEQ ID NO: 48, and a CDR3 comprising the amino acid sequence set forth in SEQ ID NO. 12 or SEQ ID NO: 49.

Embodiment 13. The antibody of any one of embodiments 1 to 8, wherein the antibody comprises a VH and a VL, wherein the VH comprises a CDR1 comprising the amino acid sequence set forth in SEQ ID NO. 6 or SEQ ID NO: 43, a CDR2 comprising the amino acid sequence set forth in SEQ ID NO. 7 or SEQ ID NO: 44, and a CDR3 comprising the amino acid sequence set forth in SEQ ID NO. 8 or SEQ ID NO: 45; and wherein the VL comprises a CDR1 comprising the amino acid sequence set forth in SEQ ID NO. 14, SEQ ID NO. 50 or SEQ ID NO. 51; a CDR2 comprising the amino acid sequence set forth in SEQ ID NO. 15 or SEQ ID NO. 52; and a CDR3 comprising the amino acid sequence set forth in SEQ ID NO. 16 or SEQ ID NO. 53.

Embodiment 14. The antibody of any one of embodiments 1 to 8, wherein the antibody comprises a VH and a VL, wherein the VH comprises a CDR1 comprising the amino acid sequence set forth in SEQ ID NO. 6 or SEQ ID NO: 43, a CDR2 comprising the amino acid sequence set forth in SEQ ID NO. 7 or SEQ ID NO: 44, and a CDR3 comprising the amino acid sequence set forth in SEQ ID NO. 8 or SEQ ID NO: 45; and wherein the VL comprises a CDR1 comprising the amino acid sequence set forth in SEQ ID NO. 18 or SEQ ID NO. 54, a CDR2 comprising the amino acid sequence set forth in SEQ ID NO. 19 or SEQ ID NO. 55, and a CDR3 comprising the amino acid sequence set forth in SEQ ID NO. 20 or SEQ ID NO. 56.

Embodiment 15. The antibody of any one of embodiments 1 to 8, wherein the antibody comprises a heavy chain variable region (VH) comprising the amino acid sequence of SEQ ID NO: 1, SEQ ID NO: 5, or humanized versions thereof.

Embodiment 16. The antibody of any one of embodiments 1 to 8 and 15, wherein the antibody comprises a light chain variable region (VL) comprising the amino acid sequence of SEQ ID NO: 9, SEQ ID NO: 13, SEQ ID NO: 17, or humanized versions thereof.

Embodiment 17. The antibody of any one of embodiments 1 to 8, wherein the antibody comprises a VH comprising the amino acid sequence of SEQ ID NO. 1 or a humanized version thereof; and a VL comprising the amino acid sequence of SEQ ID NO. 9 or a humanized version thereof.

Embodiment 18. The antibody of any one of embodiments 1 to 8, wherein the antibody comprises a VH comprising the amino acid sequence of SEQ ID NO. 5 or a humanized version thereof; and a VL comprising the amino acid sequence of SEQ ID NO. 9 or a humanized version thereof.

Embodiment 19. The antibody of any one of embodiments 1 to 8, wherein the antibody comprises a VH comprising the amino acid sequence of SEQ ID NO. 1 or a humanized version thereof; and a VL comprising the amino acid sequence of SEQ ID NO. 13 or a humanized version thereof.

Embodiment 20. The antibody of any one of embodiments 1 to 8, wherein the antibody comprises a VH comprising the amino acid sequence of SEQ ID NO. 5 or a humanized version thereof; and a VL comprising the amino acid sequence of SEQ ID NO. 13 or a humanized version thereof.

Embodiment 21. The antibody of any one of embodiments 1 to 8, wherein the antibody comprises a VH comprising the amino acid sequence of SEQ ID NO. 1 or a humanized version thereof; and a VL comprising the amino acid sequence of SEQ ID NO. 17 or a humanized version thereof.

Embodiment 22. The antibody of any one of embodiments 1 to 8, wherein the antibody comprises a VH comprising the amino acid sequence of SEQ ID NO. 5 or a humanized version thereof; and a VL comprising the amino acid sequence of SEQ ID NO.17 or a humanized version thereof.

Embodiment The antibody of any of embodiments 1-8, wherein the antibody comprises a VH, said VH comprising at least one, and up to three, of the CDR sequences of SEQ ID NO: 2, SEQ ID NO: 40, SEQ ID NO: 6, SEQ ID NO: 43, SEQ ID NO: 3, SEQ ID NO: 41, SEQ ID NO: 7, SEQ ID NO: 44, SEQ ID NO: 4, SEQ ID NO: 42, SEQ ID NO: 8 or SEQ ID NO: 45.

Embodiment 24. The antibody of any of embodiments 1-8 and 23, wherein the antibody comprises a VL, said VL comprising at least one, and up to three, of the CDR sequences of SEQ ID NO: 10, SEQ ID NO: 46, SEQ ID NO: 47, SEQ ID NO: 14, SEQ ID NO: 50, SEQ ID NO: 51, SEQ ID NO: 18, SEQ ID NO: 54, SEQ ID NO: 11, SEQ ID NO: 48, SEQ ID NO: 15, SEQ ID NO: 52, SEQ ID NO: 19, SEQ ID NO: 55, SEQ ID NO: 12, SEQ ID NO: 49, SEQ ID NO: 16, SEQ ID NO: 53, SEQ ID NO: 20 or SEQ ID NO: 56.

Embodiment 25. An antibody comprising the HCDRs and LCDRs of Combination 1 of Table 1c.

Embodiment 26. An antibody comprising the HCDRs and LCDRs of Combination 2 of Table 1c.

Embodiment 27. An antibody comprising the HCDRs and LCDRs of Combination 3 of Table 1c.

Embodiment 28. An antibody comprising the HCDRs and LCDRs of Combination 4 of Table 1c.

Embodiment 29. An antibody comprising the HCDRs and LCDRs of Combination 5 of Table 1c.

Embodiment 30. An antibody comprising the HCDRs and LCDRs of Combination 6 of Table 1c.

Embodiment 31. The antibody of any one of embodiments 1 to 30, wherein the antibody is an antigen-binding fragment thereof.

Embodiment 32. The antibody of any one of embodiments 1 to 30, wherein the antibody is a full length antibody.

Embodiment 33. The antibody of any one of embodiments 1 to 32, wherein the antibody selectively binds a Centrin-1 epitope, wherein the epitope comprises any one of the epitopes selected from the group consisting of SEQ ID NO: 21-39.

Embodiment 34. The antibody of any one of embodiments 1 to 33, wherein the antibody is conjugated to a radionuclide.

Embodiment 35. The antibody of embodiment 34, wherein the radionuclide is an α-emitting or a β-emitting radioisotope.

Embodiment 36. The antibody of embodiment 34, wherein the radionuclide comprises 213-Bismuth, 177-Lutetium, 212-Lead, 225 Actinium, 227-Thorium, 186-Rhenium, or 188-Rhenium.

Embodiment 37. The antibody of any one of embodiments 1 to 36, wherein the antibody is conjugated to a cytotoxin.

Embodiment 38. The antibody of any one of embodiments 1 to 36, wherein the antibody is bispecific.

Embodiment 39. The antibody of embodiment 38, wherein the antibody comprises a first specificity to Centrin-1 and a second specificity to an immune checkpoint inhibitor.

Embodiment 40. The antibody of any one of embodiments 1 to 39, wherein the antibody is humanized.

Embodiment 41. A pharmaceutical composition comprising any one of the antibody of embodiments 1 to 40 and a pharmaceutically acceptable excipient.

Embodiment 42. A method of treating a cancer in a subject in need thereof comprising administering to the subject in need thereof a therapeutically effective amount of the antibody or composition of any one of embodiments 1 to 41.

Embodiment 43. The method of embodiment 42, wherein the cancer is pancreatic cancer or prostate cancer.

Embodiment 44. The method of embodiment 43, wherein the cancer is pancreatic cancer.

Embodiment 45. The method of embodiment 44, wherein the pancreatic cancer is pancreatic ductal adenocarcinoma (PDAC).

Embodiment 46. The method of embodiment 43, wherein the cancer is prostate cancer.

Embodiment 47. The method of embodiment 46, wherein the prostate cancer is adenocarcinoma of the prostate.

Embodiment 48. The method of any one of embodiments 42-47, wherein the administration is systemic, regional, local, or intracavity administration.

Embodiment 49. A method of determining that a subject has, or is at risk for developing cancer comprising contacting a biological sample from the subject with any one of the antibodies of embodiments 1 to 40, and determining that the subject has, or is at risk for developing, cancer if the relative level of Centrin-1 is higher than a control value.

Embodiment 50. A method of detecting a cancer in a subject comprising administering to the subject any one of the antibodies or compositions of embodiments 1 to 41.

Embodiment 51. The method of embodiment 49 or 50, wherein the cancer is pancreatic cancer or prostate cancer.

Embodiment 52. The method of embodiment 51, wherein the cancer is pancreatic cancer.

Embodiment 53. The method of embodiment 52, wherein the pancreatic cancer is pancreatic ductal adenocarcinoma (PDAC).

Embodiment 54. The method of embodiment 53, wherein the subject has a family history of pancreatic ductal adenocarcinoma (PDAC).

Embodiment 55. The method of embodiment 51, wherein the cancer is prostate cancer.

Embodiment 56. The method of embodiment 55, wherein the prostate cancer is adenocarcinoma of the prostate.

Embodiment 57. The method of embodiment 55, wherein the subject is at risk of developing, is suspected to have developed or has developed pancreatic cancer or prostate cancer.

Embodiment 58. The method of embodiment 57, wherein the cancer is metastasized.

Embodiment 59. The method of embodiment 49, wherein the sample is a liquid biopsy, tissue biopsy, or blood sample.

Embodiment 60. The method of any one of embodiments 49 to 59, comprising administering a treatment to the subject.

Embodiment 61. A nucleic acid molecule encoding any one of the antibodies of embodiments 1 to 40.

Embodiment 62. A recombinant expression vector comprising the nucleic acid molecule of embodiment 61.

Embodiment 63. A host cell comprising the expression vector of embodiment 62.

Embodiment 64. A method of producing the antibodies of any one of embodiments 1 to 40, comprising growing the host cell of embodiment 67 under conditions permitting production of the antibody, and recovering the produced antibody.

EXAMPLES

Example 1

Immunization

Peptides were synthesized by Genemed Synthesis Inc. (San Antonio, Tex.). Peptide sequences were selected based on a comparison of the amino acid sequences of Centrin-1 and Centrin-2 (FIG. 1). A 15-amino acid residue peptide comprising the sequence [KPSAASTGQKRKVAP] was chosen as the most likely to be immunogenic. This peptide was derived from the amino terminus of the Centrin-1 protein beginning at the seventh amino acid residue. Peptide antigen was prepared as an unmodified peptide. Peptide antigen was additionally prepared as a conjugate with poly-L-lysine. Several antigenic peptides can be linked to a single poly-L-lysine backbone, thus rendering this antigen more likely to stimulate antibody production. A cDNA clone of the human Centrin-1 HIS tagged protein was purchased from GeneCopoeia.

Five BALB/c mice were immunized by injection with an emulsion of the poly-L-lysine peptide antigen and complete Freund's adjuvant. The mice were boosted after two weeks and six weeks with the poly-L-lysine conjugated peptide antigen and incomplete Freund's adjuvant. At 4 months and 6 months following the initial injection, the mice were re-boosted with the modified peptide antigen. The mice were rested for 10 months and most promising mouse was boosted with purified Centrin-1-HIS tagged protein, and sacrificed 3 days following the final boost. Sera samples were collected two weeks after each boost to test for binding to Centrin-1 by ELISA (Enzyme-linked immunosorbent assay). Pre-immune sera were used for negative controls.

Example 2

Production and Screening of Hybridomas

Murine B cell-myeloma hybridomas were produced by fusing myeloma cells, Ag8.653 or NSObcl2 with murine B cells. The spleen was removed from the immunized mouse, cells isolated by balloon method and the RBC lysed. Spleen cells were then washed and mixed with myeloma cells (3:1 spleen to myeloma ratio). The mixture was spun down, the rinse removed, and the pellet gently resuspended. Polyethylene glycol (PEG 4000) was slowly added and swirled to mix. Saline with glucose was slowly added to the cell suspension. Finally, the cells were spun down and resuspended in hypoxanthine-aminopterin-thymidine (HAT) selection medium. The cells were plated in 96-well plates at 3×10⁵ cells/ml.

After about 2 weeks, supernatant from each well was screened by ELISA for binding to Centrin-1. Cells from positive wells were then transferred to 24-well plates, and also plated in soft agar. After 1 week, individual clones were picked from the soft agar and transferred to 96-well plates. Clones were grown for about 3 days until they were visible by eye then tested by ELISA for binding to Centrin-1. Positive clones were also tested for binding to Centrin-2 (Sino Biologicals). Clones which met the criteria of being positive for Centrin-1 binding and negative for Centrin-2 binding were expanded and frozen. Three hundred sixty eight hybridoma cultures were screened by ELISA for the presence of Centrin-1-reactive antibodies. The capture ELISA was conducted as follows: Costar Corning high binding polystyrene plates (catalogue #9018) were coated overnight with Centrin-1 antigen, blocked, and probed with supernatant from the hybridomas (the analyte). Finally, binding was detected using mixture of goat/anti-mouse IgG antibodies (Southern Biotechnology) conjugated to alkaline phosphatase (AP). The antibodies that were used included IgG1, IgG2a, IgG2b, and IgG3. AP labeled goat anti mouse IgM was also used as for detection. The plates were washed between every addition to remove non-specific binding. Para-Nitrophenylphosphate (pNPP) was used to indicate the presence of the Centrin-1-reactive antibodies.

Ten of the 368 hybridomas screened were found to be positive for the presence of Centrin-1 antibodies, with some producing IgG, some IgM, and some both. Fifty subclones were then tested for Centrin-1 and Centrin-2 binding. 18 of the 50 subclones that produced only IgG were positive for Centrin-1-reactive antibodies. These subclones were grown and then frozen at −80° C. A titration was performed with commercial antibodies to Centrin-1 M01 (Catalogue #H00001068-M01, Novus Biologicals, Littleton, Colo., USA) and M05 (Catalogue #H00001068-M05, Abnova, Taipei, Taiwan) to determine an optimal concentration of antigen for coating wells in ELISA assays. A concentration of 1.25 µg/mL of Centrin-1 or Centrin-2 was determined to be an optimal concentration for the assay. Using these conditions, the binding of the IgMs and IgGs to Centrin-1 and Centrin-2 was investigated.

Table 4 and Table 5 show that of 18 antibody producing clones, which include 4 IgM antibodies and 14 IgG antibodies, at least one IgM antibody, at least 2 IgG1 antibodies and at least 2 IgG2b antibodies bind preferentially to Centrin-1 relative to Centrin-2. While the Centrin-1/Centrin-2 binding ratio for the commercially available IgG M01 was about 1.25 (Table 5), the Centrin-1/Centrin-2 binding ratio of several of the newly generated IgMs and IgGs was >2. For instance, the Centrin-1/Centrin-2 binding ratio for IgGs produced by the 69-11, 76-6 and 76-14 clones were about 7.74, 5.73 and 8.85, respectively.

TABLE 4

Binding of IgM antibodies to Centrin-1 and Centrin-2

| Clones | Centrin-1/Centrin-2 Binding Ratio |
|---|---|
| 117-32 | 2.45 |
| 117-33 | 2.14 |
| 117-34 | 2.47 |
| 117-35 | 2.27 |
| Mouse 67 | 0.92 |
| HAT | 1.18 |

TABLE 5

Binding of IgG antibodies to Centrin-1 and Centrin-2

| Clones | Centrin-1/Centrin-2 Binding Ratio |
|---|---|
| 69-11 | 7.741176471 |
| 69-13 | −2 |
| 69-18 | 2.826666667 |
| 69-25 | 1.403669725 |
| 76-1 | 3.72 |
| 76-6 | 5.727272727 |
| 76-13 | 2.487179487 |
| 76-14 | 8.846153846 |
| 76-15 | 3.913043478 |
| 76-16 | −1.022222222 |
| 123-1 | 1.772727273 |
| 123-13 | 1.302521008 |
| 117-8 | 1.038461538 |
| 117-20 | 1.78125 |
| M01 | 1.249240122 |
| HAT | 0.130885122 |

Example 3

Comparison to the Commercial Antibodies to Centrin-1

Figure 3B:
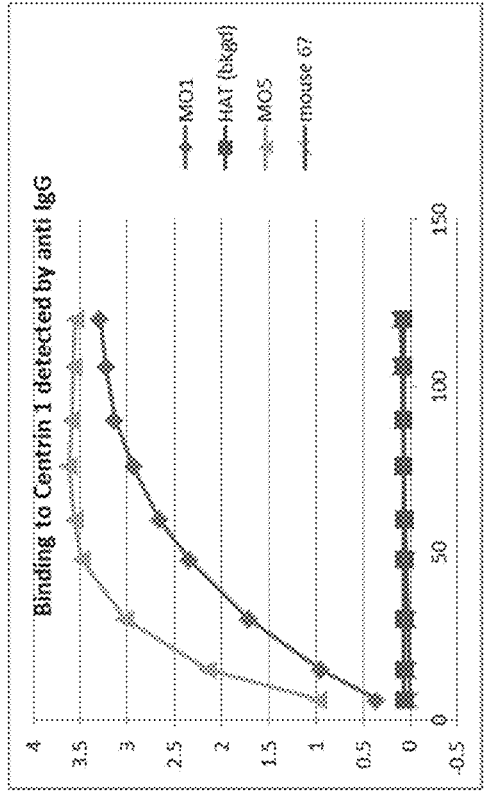
Figures 4A, 4B:
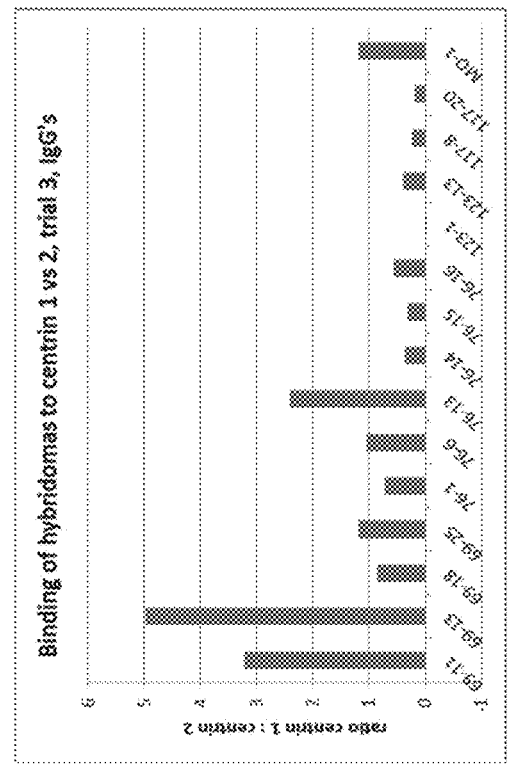
FIG. 4A (left panel) and 4B (right panel) are graphs comparing the binding of the antibodies of the present disclosure to Centrin-1 and Centrin-2.
Figure 5A:
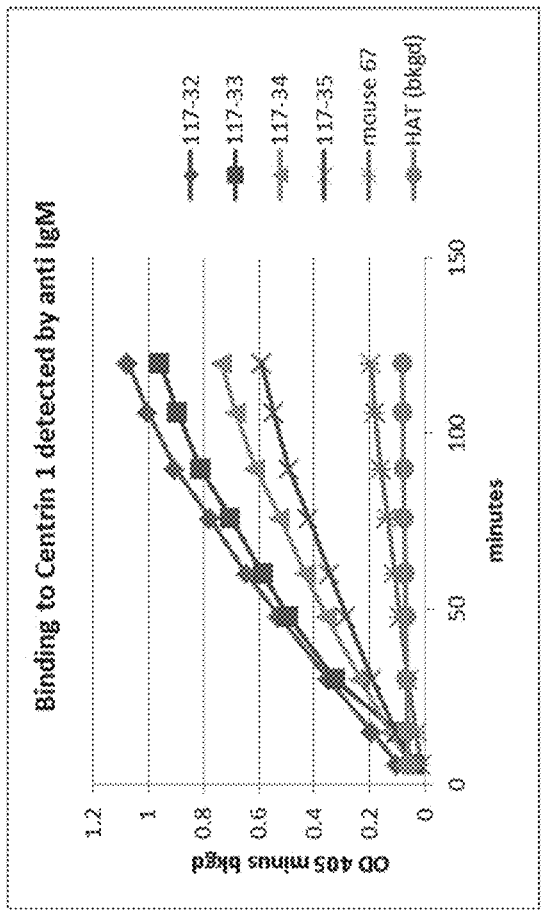
FIG. 5A (upper panel) and 5B (lower panel) are graphs showing the relative binding to Centrin-1 (upper panel) versus Centrin-2 (lower panel) of the IgM class antibodies according to the present disclosure.
Figure 5B:
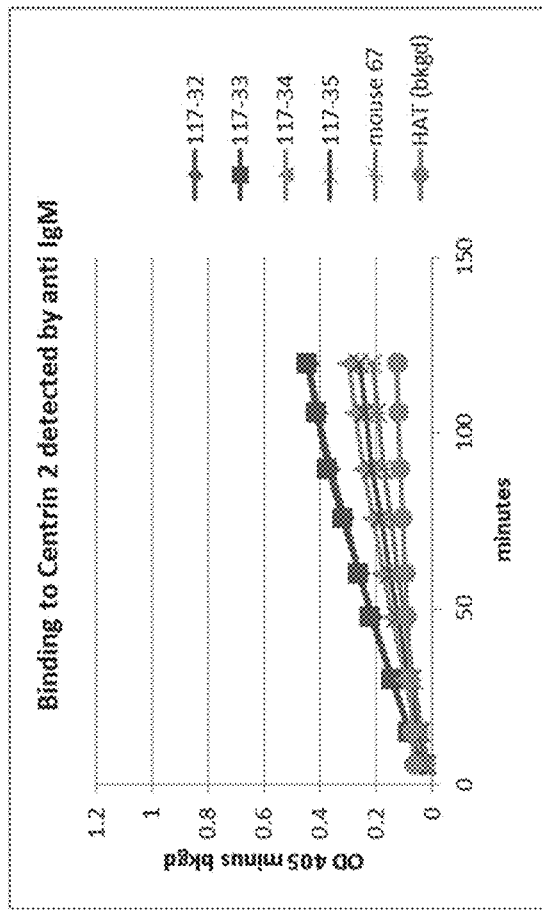
Figure 6A:
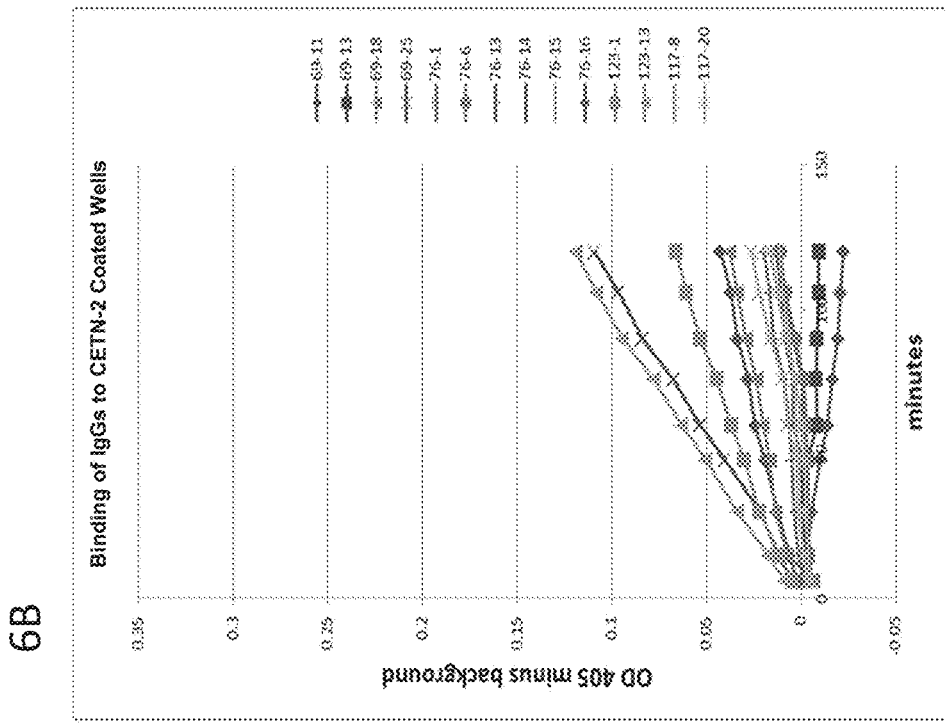
FIG. 6A (left panel) and 6B (right panel) are graphs showing the relative binding to Centrin-1 (left panel) versus Centrin-2 (right panel) of the IgG class Centrin-1 antibodies according to the present disclosure.
Figure 6B:
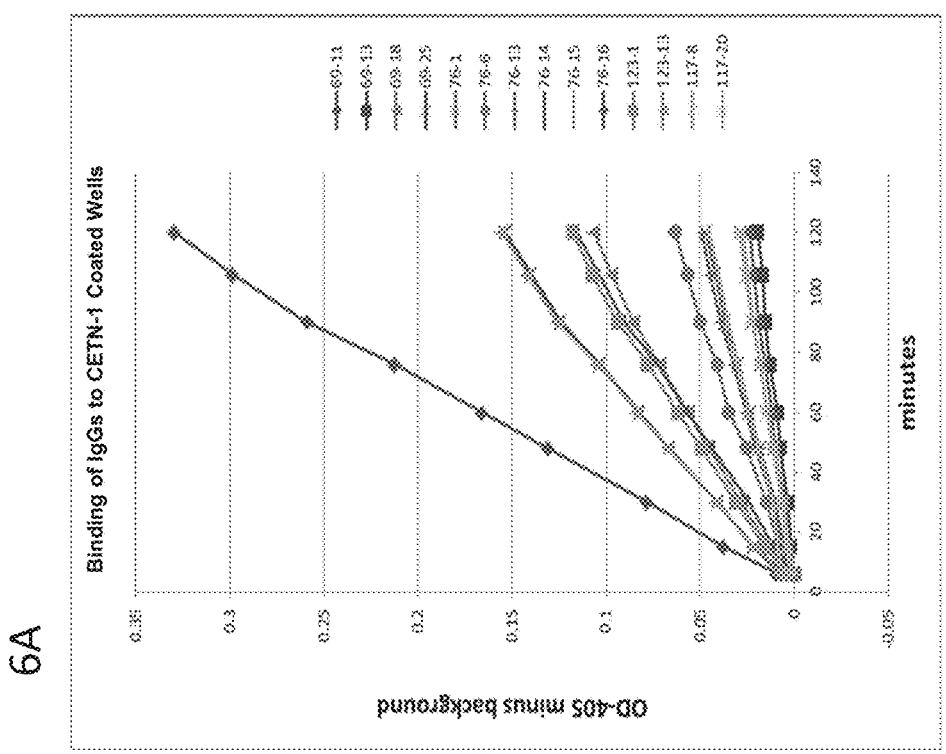
Figure 7:
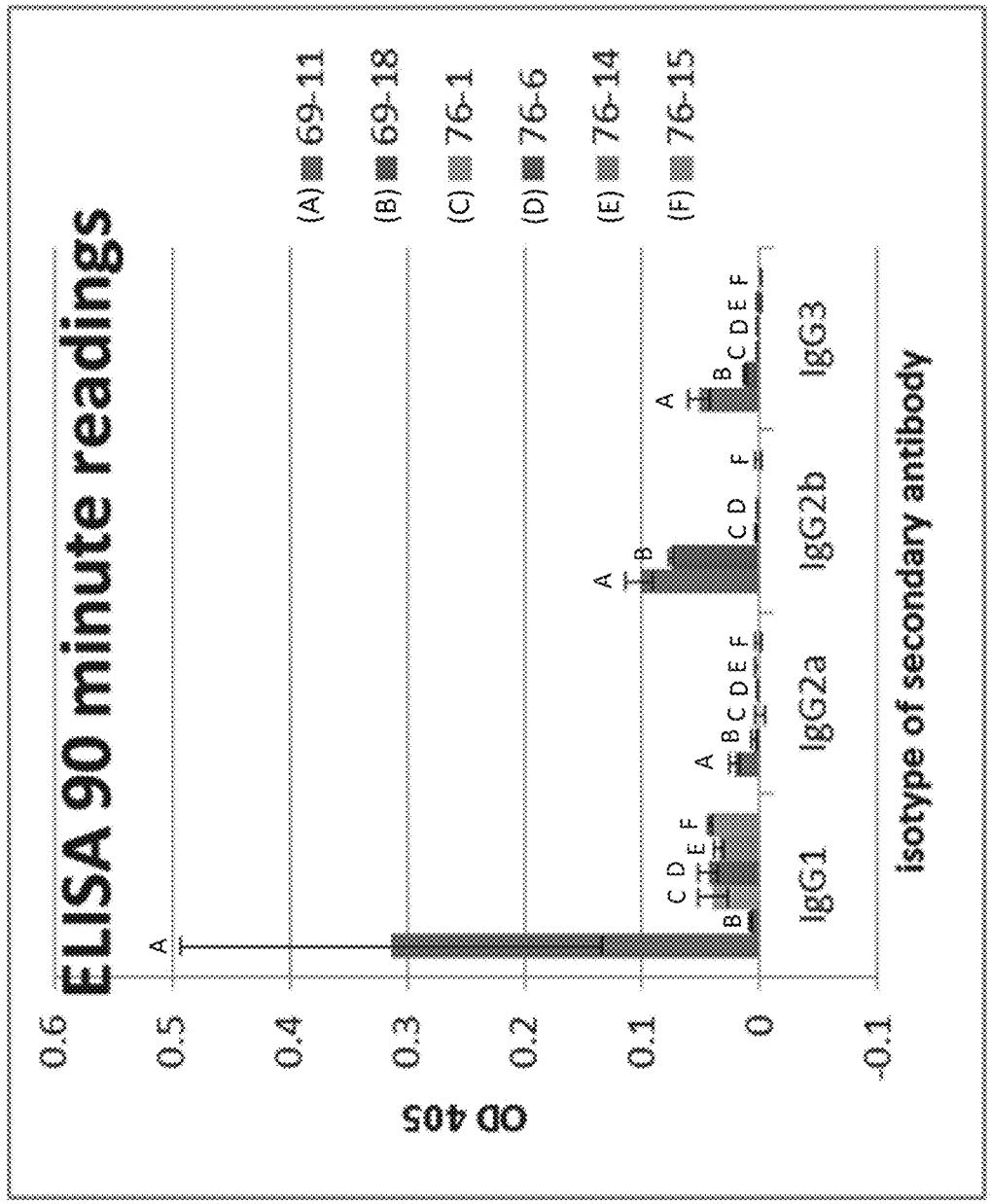
FIG. 7 is a graph showing the subtypes of IgG antibodies to Centrin-1 determined by ELISA for subsequent biomarker and radiolabeling use.

A comparison was made of the binding of commercial antibodies M01 and M05 to Centrin-1 and Centrin-2 using capture ELISA. FIG. 3A (left panel) and 3B (right panel) are graphs comparing the binding of commercial antibodies M01 and M05 to Centrin-1 and Centrin-2 using capture ELISA. Commercial antibodies bind Centrin-2 about 75% as strongly as they bind Centrin-1 (FIGS. 3A-3B). In contrast, both IgG and IgM anti-Centrin-1 antibodies of the present invention bind to Centrin-1 several fold better than Centrin-2 (FIGS. 4-6). FIG. 4A (left panel, IgG antibodies) and 4B (right panel, IgM antibodies) are graphs comparing the ratio of the binding of the antibodies produced herein to Centrin-1 and Centrin-2. FIG. 5A (left panel) and 5B (right panel) provide the raw data for IgM antibodies binding to Centrin-1 compared to Centrin-2. FIGS. 6A and 6B provide the raw data for IgG antibodies binding to Centrin-1 compared to Centrin-2. The results of this study show that the antibodies bind Centrin-1 several fold better than Centrin-2. In particular, FIG. 7 shows that antibodies having the IgG1 isotype bind Centrin-1 with a higher affinity.

Example 4

Tissue Microarray Analysis

GeneTex tissue microarray analysis was used to evaluate the binding of the immune serum from Centrin-1-immunized mouse to pancreatic adenocarcinoma (PDAC) versus normal pancreas. Microwave pre-treatment (heat-induced epitope retrieval) was performed for 30 min at 90° C. on all samples. The serum was diluted 1:1,000 and incubated with the microarrays overnight at 4° C. Standard indirect immunoperoxidase procedures were used for immunohistochemistry (ABC-Elite, Vector Laboratories). Diaminobenzidine was used as a chromogen.

Figures 8A, 8B, 8C, 8D, 8E, 8F:
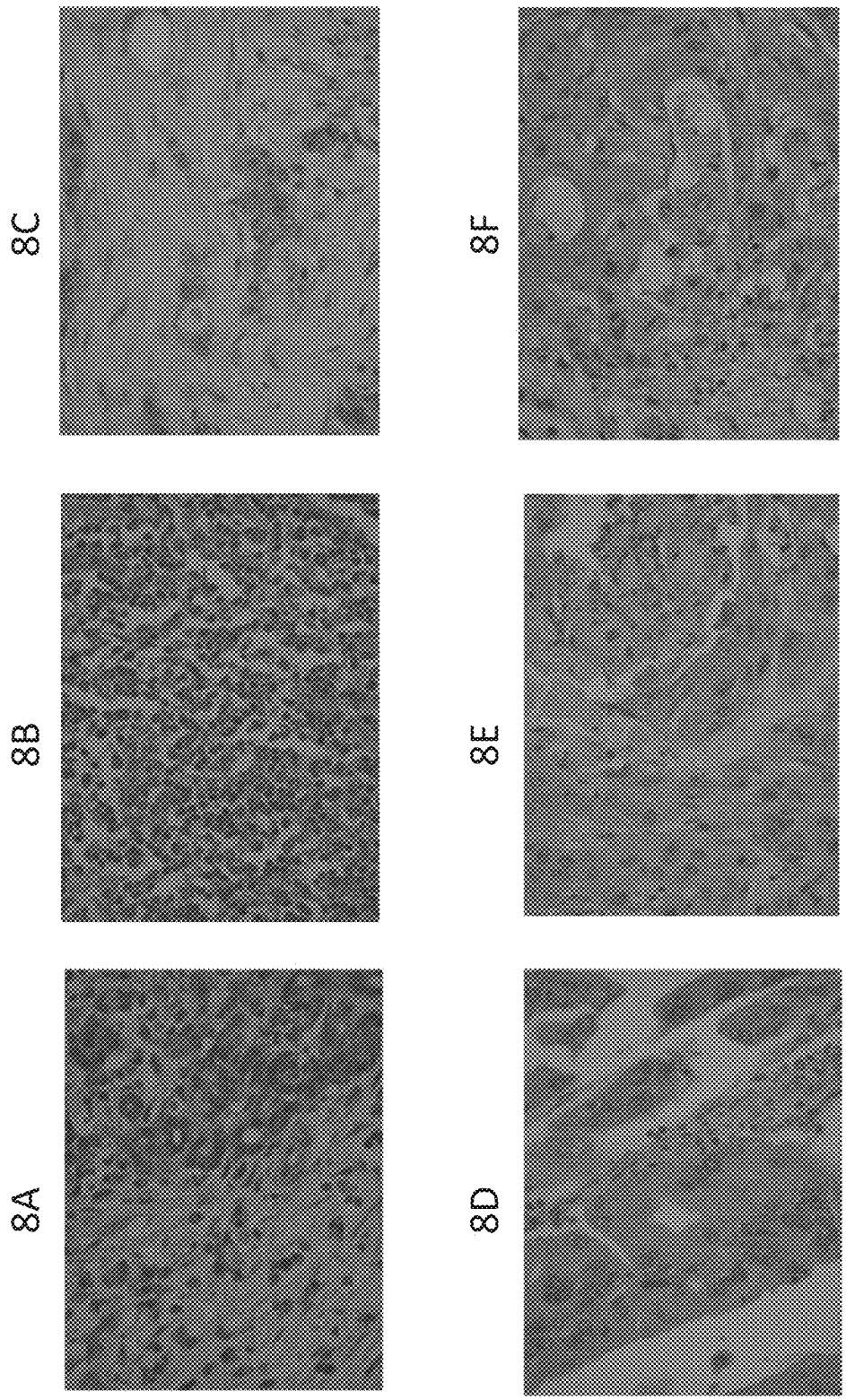
FIGS. 8A-8F show the results of a tissue microarray analysis determining the binding of immune serum from Centrin-1-immunized mouse to pancreatic adenocarcinoma tissue (FIGS. 8A-8D) and normal pancreatic tissue (FIGS. 8E-8F).

The tissue microarray included a total 24 cases (in duplicate), including 20 cases of PDAC and 4 cases of normal pancreas. FIGS. 8A and 8B show examples of tumor samples with pronounced binding of immune serum, while FIGS. 8C and 8D show examples of tumor samples with no appreciable binding of the serum. Overall, 10 PDAC cases (50%) demonstrated pronounced binding of immune serum. Importantly, there was no specific binding of immune serum to any of the 4 cases of normal pancreas (FIGS. 8E-8F).

Example 5

Conjugation of Radionuclide to Centrin-1 Aantibodies

Antibody produced by the clones 69-11 and 76-6 (Table 5) were conjugated with the bifunctional chelating agent N-[2-amino-3-(p-isothiocyanatophenyl)propyl]-trans-cyclohexane-1,2-diamine-N,N',N'',N''',N''''-pentaacetic acid (CHXA") (Macrocyclics, Dallas, Tex.) for subsequent radiolabeling with $^{213}$Bi. $^{225}$Ac for construction of the $^{213}$Bi/$^{225}$Ac radionuclide generator was purchased from Oak Ridge National Laboratory, Tenn., USA. $^{213}$Bi was eluted from a $^{213}$Bi/$^{225}$Ac radionuclide generator with a 0.1 M HI solution. The pH of the solution was adjusted to 6.5 with ammonium acetate buffer and used for radiolabeling the antibodies produced by 69-11 and 76-6 clones conjugated with CHXA. 177Lu in form of 177Lu chloride was acquired from Radiomedix (TX, USA) and incubated for 60 min at 37° C. with CHXA"-conjugated antibodies to achieve quantitative radiolabeling.

Example 6

In Vivo Localization Data

Nude mice bearing MiaPaCa2 (a human pancreatic carcinoma cell line purchased from the ATCC) xenografts were injected intraperitoneally with 300 uCi $^{177}$Lu-labelled antibodies produced by the 69-11 clone and microSPECT/CT imaging was performed at 1, 24, 48, 72 and 168 hours with the mice in the prone position. microSPECT/CT (micro single photon emission computer tomography/computer tomography) images were collected on a MILabs VECTor (Netherlands) microSPECT/CT scanner and processed using the comprehensive image analysis software package PMOD (version 3.9, PMOD Technologies, Inc, Switzerland). SPECT data was collected for 20 min using an Extra Ultra High Sensitivity Mouse (XUHS-M) collimator for 20-350 keV range using spiral trajectories. All SPECT images were reconstructed using 210 keV (11%) $^{177}$Lu gamma emissions on a 0.4 mm voxel grid with MILabs reconstruction software.

Figures 9A, 9B, 9C:
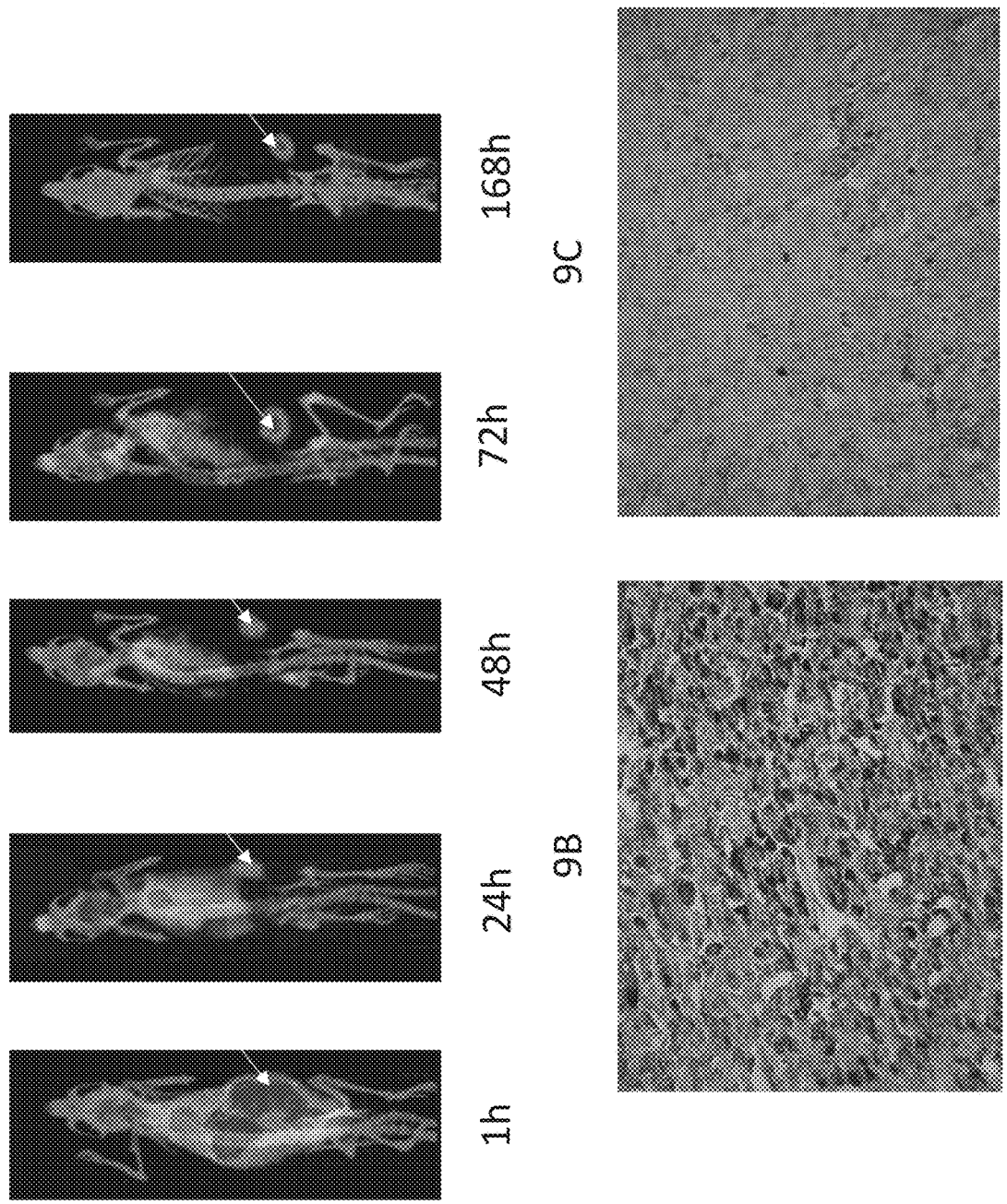
FIGS. 9A-9C visualize Centrin-1 expression in MiaPaCa2 tumors in vivo and ex vivo.

Results of the imaging are shown in FIG. 9A. About 24 hours after administration, 177Lu-labeled antibody from the 69-11 clone was seen localized to the tumors in the right flank of the mice, with the tumor uptake progressively increasing with time. Pronounced tumor uptake was still detectable at 168 hours (7 days) post injection of the antibody. These results showed that the antibody from the 69-11 clone localizes to PDAC xenografts in vivo. Furthermore, immunohistochemistry of ex vivo tumors from the mice imaged with microSPECT/CT shows that there is exuberant binding of the Centrin-1 antibody produced by the 69-11 (FIG. 9B), as compared to no binding observed with the isotype matching control MOPC21 antibody (FIG. 9C).

Example 7

In Vivo Efficacy Data

MiaPaCa-2, a human pancreatic carcinoma cell line, was purchased from American Type Culture Collection (ATCC, Manassas, Va.) and maintained as directed by ATCC. For the animal therapy experiments, MiaPaCa-2 cells were thawed and grown for two weeks in T150 flasks until 80-90% confluent at 2×10' cells/flask. Cells were removed by trypsinization, pelleted by centrifugation at 1,100 RPM for 5 min at 4° C., and resuspended in BD matrigel (BD Franklin Lakes, N.J.) using chilled pipettes and tubes, to a concentration of 5×10$^7$ cells/mL.

Six-eight week old nu/nu female mice on the BALB/c background (Charles River, Willmington, Mass.) were anesthetized with isoflurane and injected with 3×10$^6$ cells subcutaneously into the right flank. 90% of the mice injected with MiaPaCa-2 cells developed tumors by day 10 postinoculation. Mice with tumors averaging 50-60 mm$^3$ were randomized into treatment groups of five animals each and treated with: 50 µCi $^{213}$Bi-CHXA41-antibody produced by the 69-11 clone; 50 µCi $^{213}$Bi-CHXA"-antibody produced by the 76-6 clone; 30 µg unlabeled CHXA"-antibody produced by the 69-11 clone; 30 µg unlabeled CHXA"-antibody produced by the 76-6 clone; 50 µCi free $^{213}$Bi; or PBS. The tumors were measured in 3 dimensions with electronic calipers every 2 days.

Figures 10A, 10B, 10C, 10D:
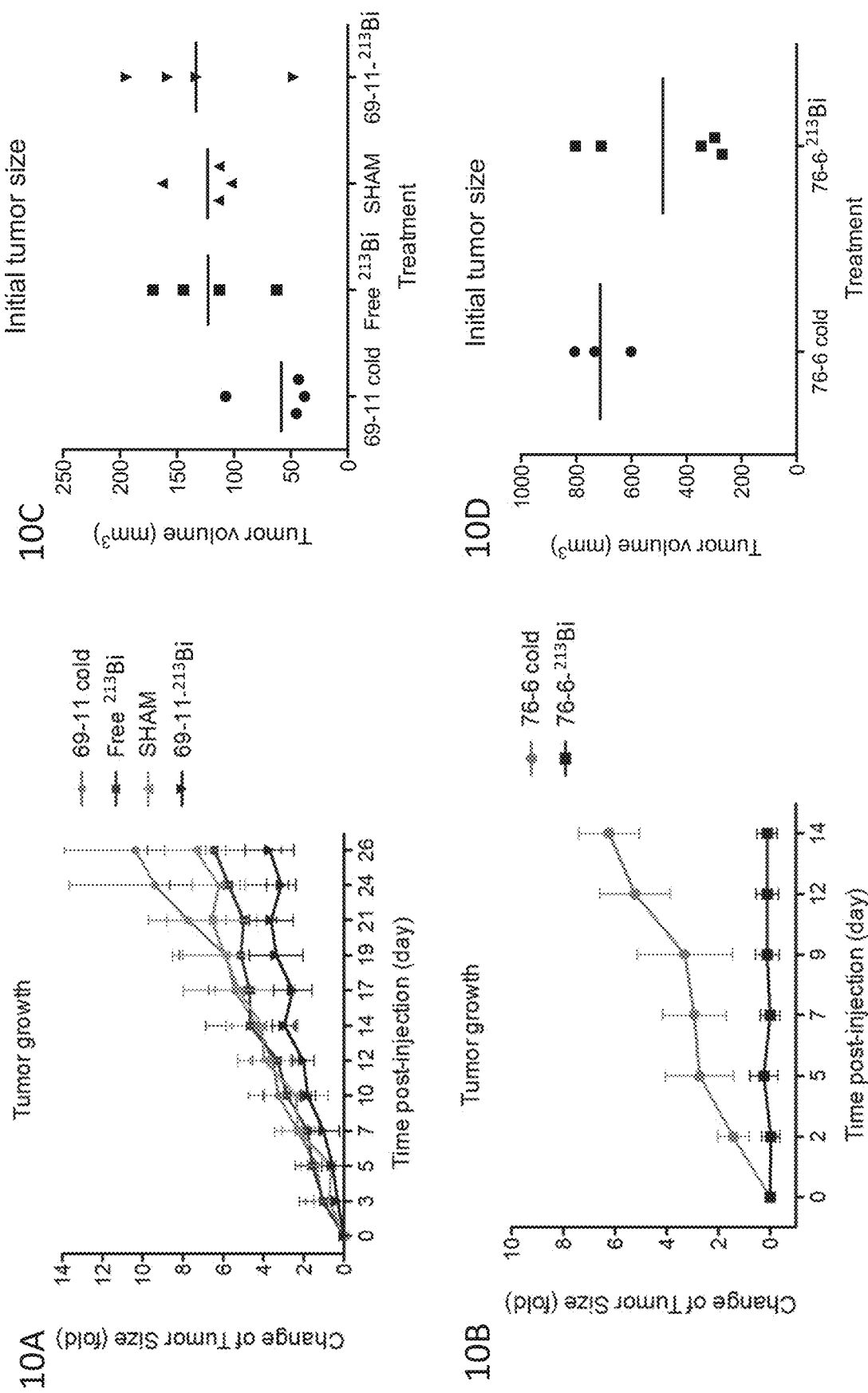
FIGS. 10A and 10B are graphs showing tumor size over time when treated with 213Bi-labeled antibodies produced by 69-11 (FIG. 10A) or 76-6 clones (FIG. 10B).
FIGS. 10C and 10D are graphs showing the initial tumor size for each mouse in each treatment group.

FIGS. 10A-10B show the changes in the tumor sizes of the radiolabeled-antibody treated mice and in the control group mice over time. While tumors in the PBS treated mice and in the control groups grew aggressively during the observation period, the treatment with 50 µCi $^{213}$Bi-labeled antibodies to Centrin-1 significantly slowed tumor growth. FIGS. 10C and 10D plot the initial tumor size of each mouse in each treatment group.

Example 8

In Vivo Effects of Conjugating Centrin-1-Specific Antibody to Two Different Radionuclides The MiaPaCa2 tumor-bearing mice were randomized into groups of 5 animals and treated with: 100 µCi (equivalent to 24 mCi in a 60 kg human) 213Bi-antibody produced by the 69-11 clone, or 200 µCi (equivalent to 48 mCi in a 60 kg human) 213Bi-antibody produced by the 69-11 clone, or 200 µCi 213Bi-IgG control, or unlabeled antibody produced by the 69-11 clone, or 100 µCi 177Lu-antibody produced by the 69-11 clone, or 200 µCi 177Lu-antibody produced by the 69-11 clone, or 200 µCi 177Lu-IgG control, or left untreated. A 5:1 µCi/µg specific activity was used and radiochemical purity was >90% via iTLC. The tumor size was measured every 3 days.

Figures 11A, 11B:
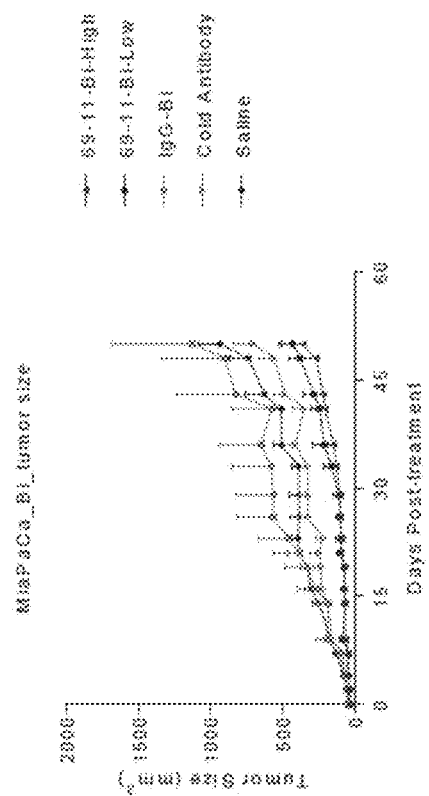
FIG. 11A (left panel) and 11B (right panel) are graphs showing tumor size over time (left panel) and fold change in tumor size over time (right panel) when tumor-bearing mice were treated with 213Bi-labeled antibodies produced by the 69-11 clone.
Figure 12A:
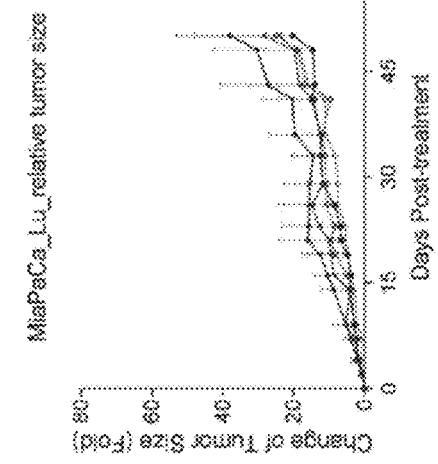
FIG. 12A (left panel) and 12B (right panel) are graphs showing tumor size over time (left panel) and fold change in tumor size over time (right panel) when tumor-bearing mice were treated with 177Lu-labeled antibodies produced by the 69-11 clone.
Figure 12B:
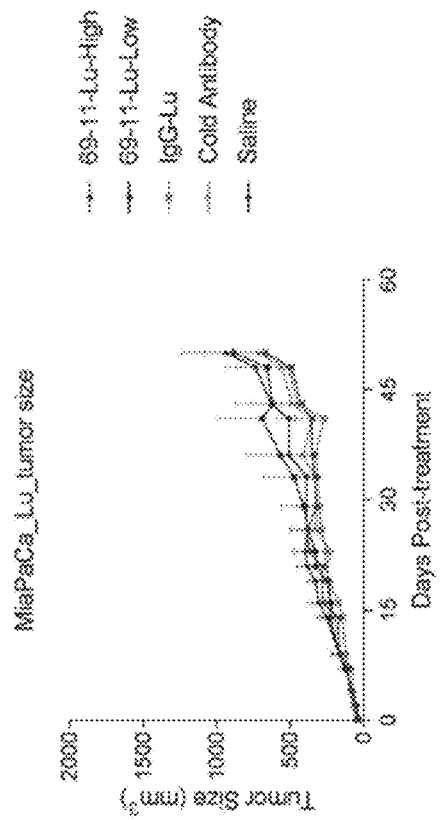
Figure 13A:
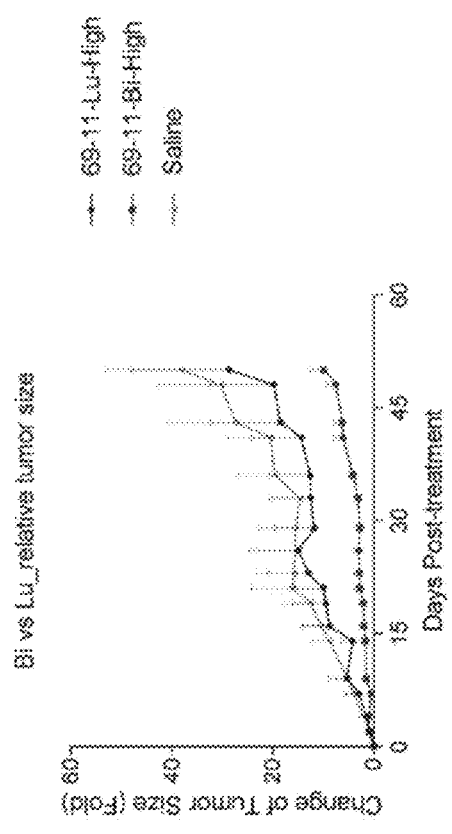
FIG. 13A (left panel) and 13B (right panel) shows a comparison between tumor size over time (left panel) and fold change in tumor size over time (right panel) upon treatment with either 213Bi-labeled antibodies produced by the 69-11 clone or 177Lu-labeled antibodies produced by the 69-11 clone.
Figure 13B:
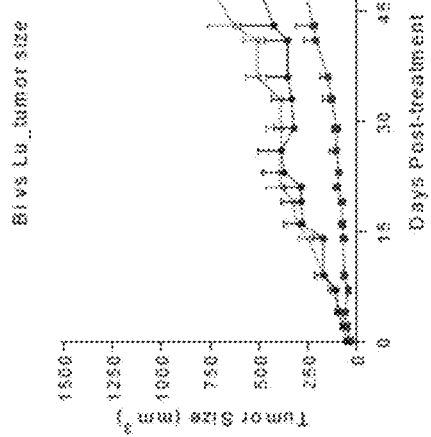

The results showed that treatment with either 100 or 200 µCi 213Bi labeled Centrin-1 antibody reduced the tumor growth rate significantly (FIGS. 11A-B), while 200 µCi of the control IgG antibody had no effect on the tumor growth. Treatment with $^{177}$Lu-labeled Centrin-1 antibody produced by the 69-11 clone was less effective in slowing down tumor growth when compared with the 177Lu-IgG control (FIGS. 12A-B). FIGS. 13A-B further illustrate the effectiveness of the 213Bi labeled Centrin-1 antibody in reducing tumor growth in comparison with $^{177}$Lu-labeled Centrin-1 antibody produced by the 69-11 clone.

Without being bound by theory, it is thought that the difference in efficacy between the 213Bi labeled Centrin-1 antibody and $^{177}$Lu-labeled Centrin-1 antibody produced by the 69-11 clone could due be the ability of the short lived 213Bi nuclide to deliver its radiation dose in a short period of time; thereby allowing its intense, high radiobiological effectiveness (RBE) to counteract the aggressive growth of PDAC, as opposed to the lower RBE beta radiation potentially delivered in a relatively protracted mode by $^{177}$Lu. Moreover, when the Centrin-1 antibodies disclosed herein are used, several fold less 213Bi activity was required to achieve a tumor response effect comparable to what was achieved with a 213Bi-labelled single strand DNA antibody described in Bryan et al. *Expert Rev Anticancer Ther.* 2014; 14:1243-9. Without being bound by theory, it is thought that this effect might be due to the high specificity of the antibodies disclosed herein, and the accessibility of the Centrin-1 antigen within the PDAC microenvironment.

Figure 14A:
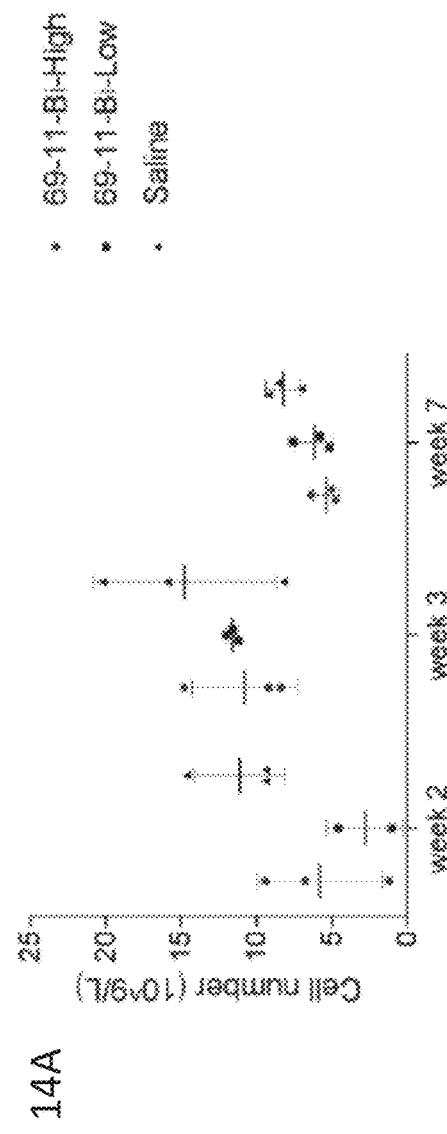
FIG. 14A (top) and 14B (down) are graphs showing the white blood cells (WBCs) count (cell number/L) over time in mice which were injected with 213Bi-labeled antibodies produced by the 69-11 clone (top) or 177Lu-labeled antibodies produced by the 69-11 clone (bottom).
Figure 14B:
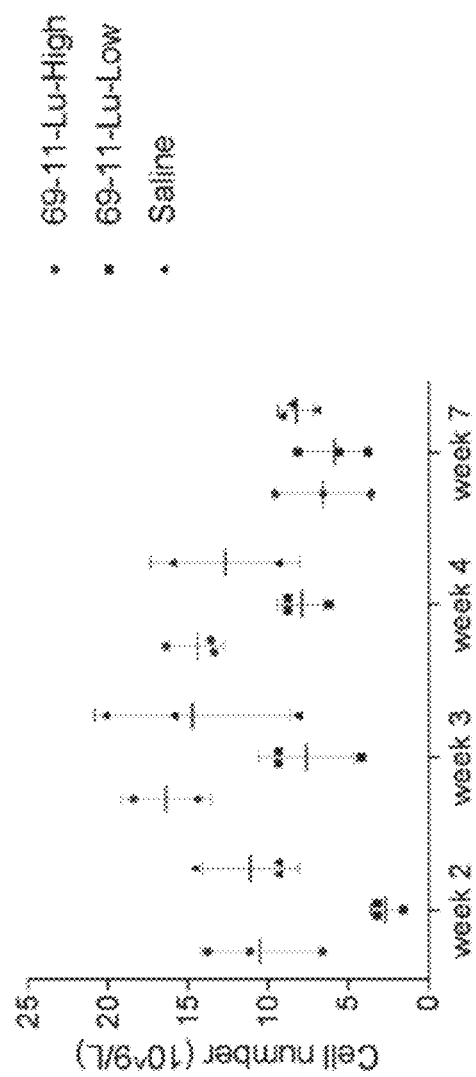
Figure 15A:
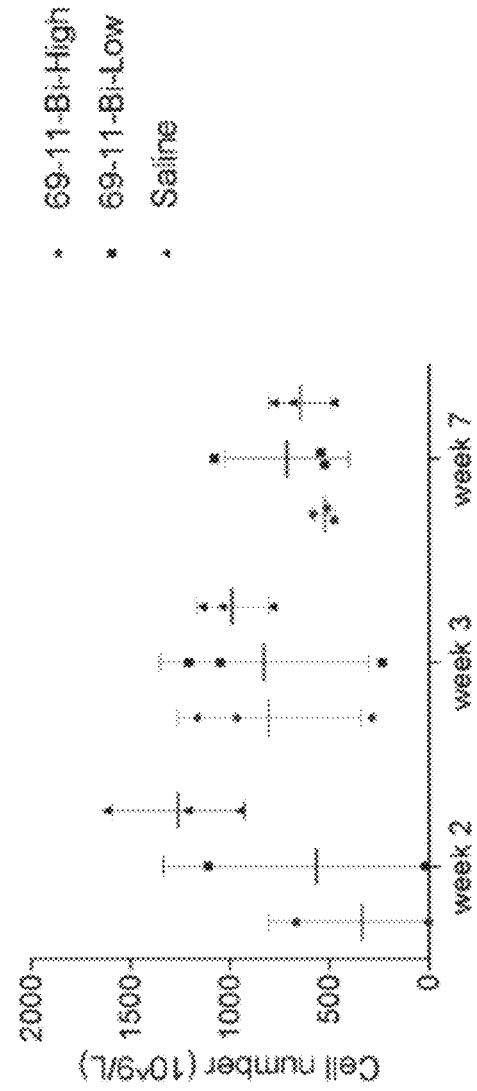
FIG. 15A (top) and 15B (down) are graphs showing the platelet count (cell number/L) over time in mice which were injected with 213Bi-labeled antibodies produced by the 69-11 clone (top) or 177Lu-labeled antibodies produced by the 69-11 clone (bottom).
Figure 15B:
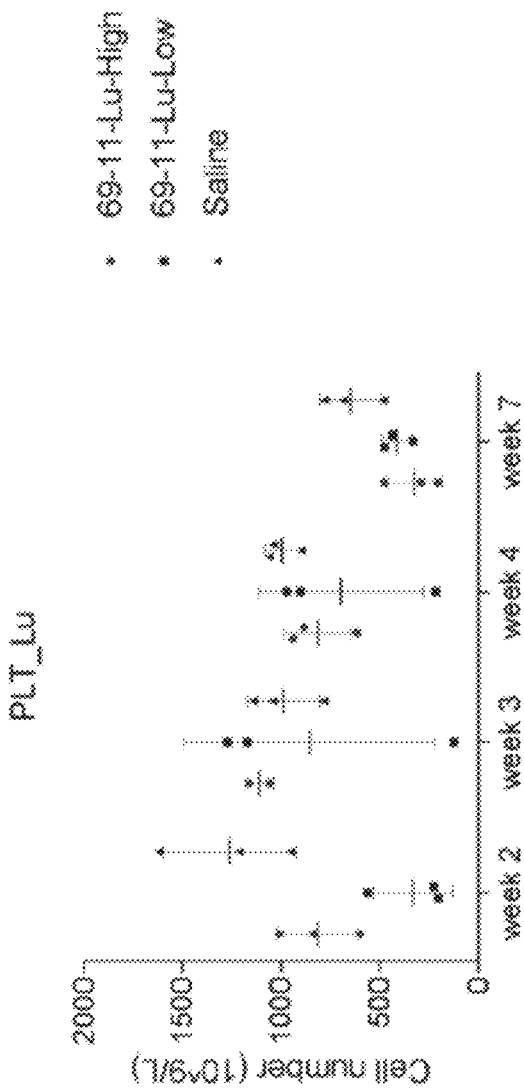
Figures 16A, 16B:
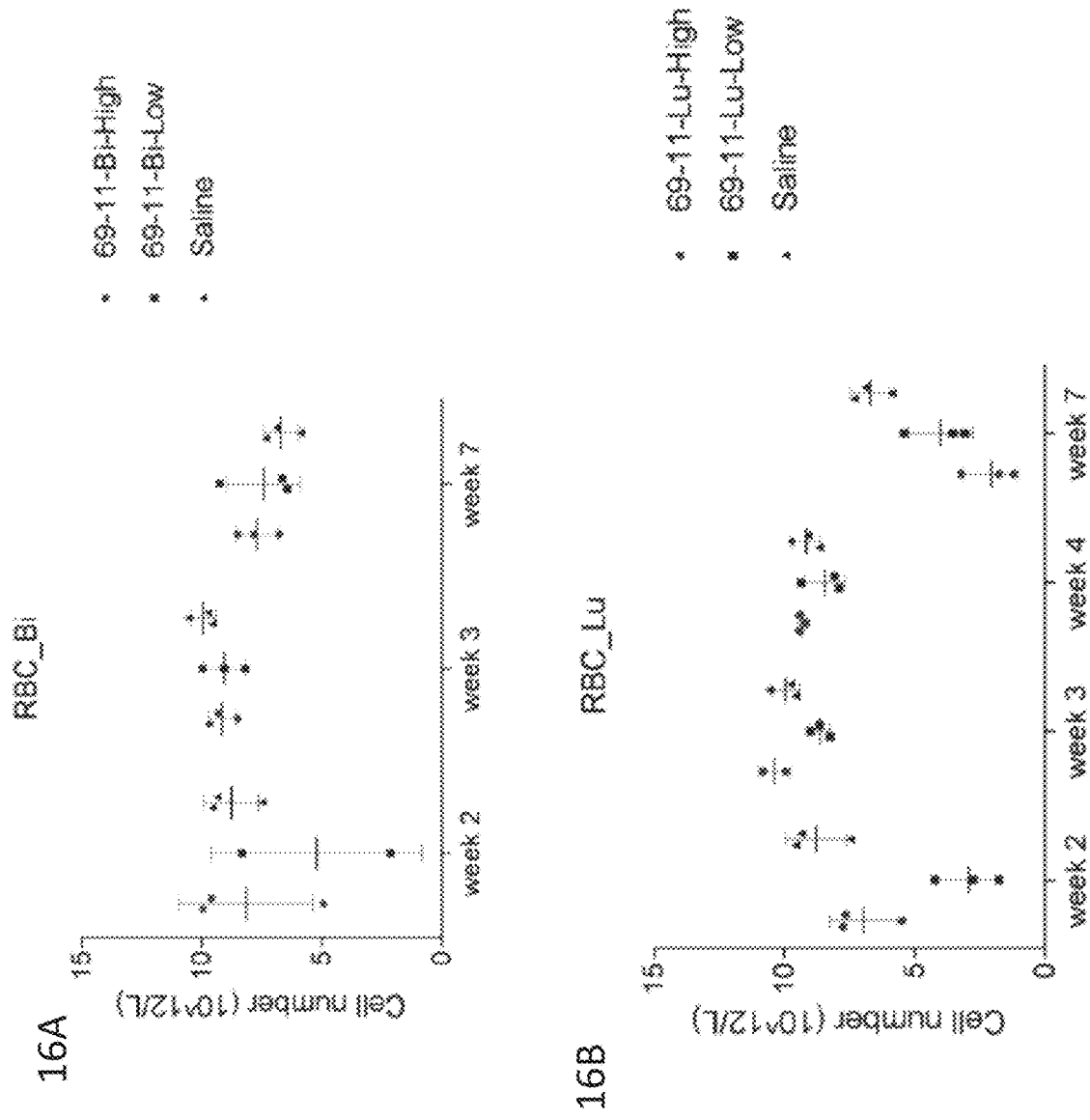
FIG. 16A (top) and 16B (down) are graphs showing the red blood cells (RBCs) count (cell number/L) over time in mice which were injected with 213Bi-labeled antibodies produced by the 69-11 clone (top) or 177Lu-labeled antibodies produced by the 69-11 clone (bottom).
Figures 17A, 17B, 17C, 17D:
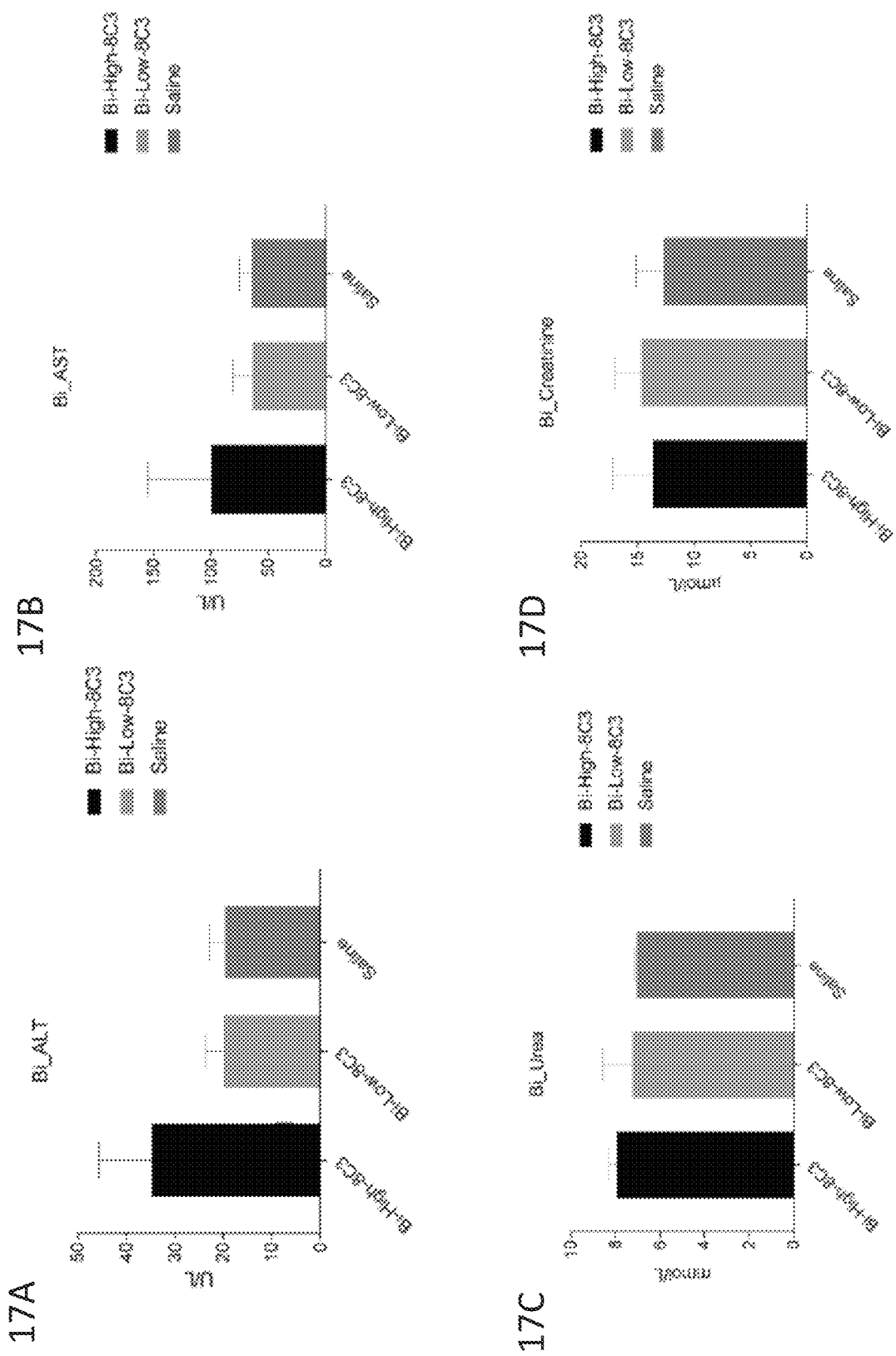
FIG. 17A (top left), 17B (top right), 17C (bottom left) and 17D (bottom right) are graphs showing the concentration (U/L) of alanine aminotransferase (ALT, top left), concentration (U/L) of aspartate amino transferase (AST, top right), concentration (mmol/L) of urea (bottom left) and concentration (μmol/L) of creatinine (bottom right) in mice which were injected with 213Bi-labeled antibodies produced by the 69-11 clone.
Figures 18A, 18B, 18C, 18D:
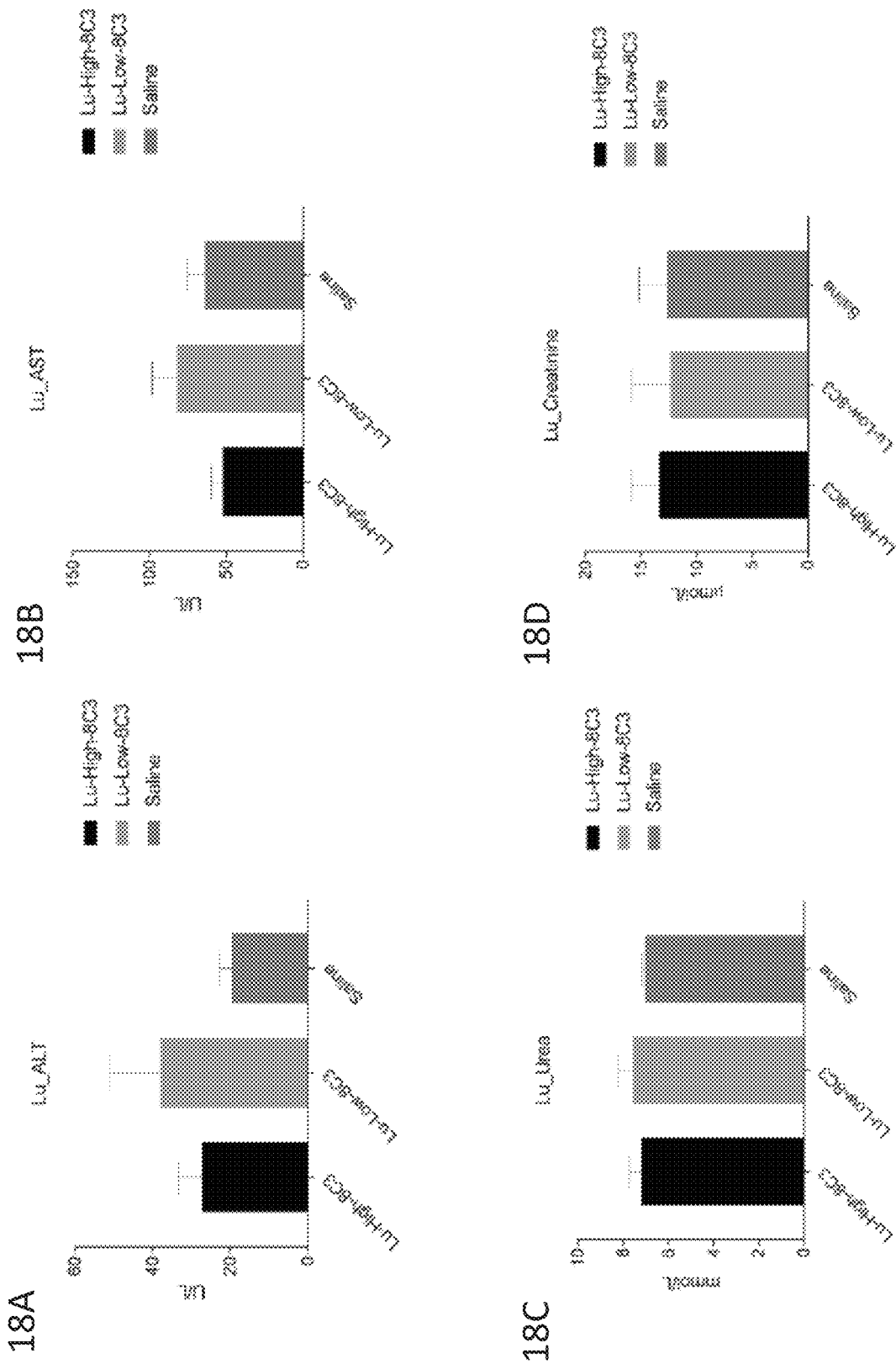
FIG. 18A (top left), 18B (top right), 18C (bottom left) and 18D (bottom right) are graphs showing the concentration (U/L) of alanine aminotransferase (ALT, top left), concentration (U/L) of aspartate amino transferase (AST, top right), concentration (mmol/L) of urea (bottom left) and concentration (μmol/L) of creatinine (bottom right) in mice which were injected with 177Lu-labeled antibodies produced by the 69-11 clone.

Hematologic toxicity was assessed on a weekly basis by measuring the counts of white blood cells (FIG. 14A-B), platelets (FIG. 15A-B) and red blood cells (FIG. 16A-B). The numbers of white blood cells, platelets and red blood cells in mice treated with either 213Bi-labeled or 177Lu-labeled Centrin-1 antibodies were similar to those of the control mice treated with saline, suggesting that the mice treated with either 213Bi-labeled or 177Lu-labeled Centrin-1 antibodies showed only transient, if any, hematologic toxicity (FIGS. 14-16).

At the completion of the observation period the mice were sacrificed and their blood was analyzed for signs of possible hepatic toxicity by measuring the concentration of aspartate transaminase (AST) and alanine transaminase (ALT). Further, the blood was also analyzed for signs of potential renal toxicity by measuring the concentration of urea and creatinine. The concentration of AST, ALT, urea and creatinine in mice treated with either 213Bi-labeled or 177Lu-labeled Centrin-1 antibodies was very similar to those of the control mice (FIGS. 17A-D and 18A-D), showing that there is no measurable liver or kidney toxicity in the mice treated with either 213Bi-labeled or 177Lu-labeled Centrin-1 antibodies.

Example 9

Identification of Centrin-1 Antibody Sequences

In order to identify the amino acid sequences of the heavy chain variable regions (VH) and light chain variable region (VL) of the Centrin-1 antibodies produced by the clones 69-11, 76-6 and 123-13, cDNAs was generated from each of the clones and amplified using RT-PCR. Sequencing was performed using a standard dye-terminator capillary sequencing method. The results of the sequencing experiments are described below.

Clone 69-11 expressed two heavy chain variable regions (VH); and one light chain variable region (VL). The first VH expressed by clone 69-11 comprised the amino acid sequence of SEQ ID NO. 1; the second VH comprised the amino acid sequence of SEQ ID NO. 5; and the VL comprised the amino acid sequence of SEQ ID NO: 9, as listed in Table 1.

Clone 76-6 expressed one VH; and 2 VLs. The VH expressed by clone 76-6 comprised the amino acid sequence of SEQ ID NO: 1; the first VL comprised the amino acid sequence of SEQ ID NO: 9; and a second VL comprised the amino acid sequence of SEQ ID NO: 13, as listed in Table 1.

Clone 123-13 expressed one VH; and 3 VLs. The VH expressed by clone 123-3 comprised the amino acid sequence of SEQ ID NO: 1; the first VL comprised the amino acid sequence of SEQ ID NO: 9; the second VL comprised the amino acid sequence of SEQ ID NO: 13 and the third VL comprised the amino acid sequence of SEQ ID NO: 17, as listed in Table 1.

The amino acid sequences of the complementarity determining regions (CDRs) of each of the VH and VL sequences described above were identified using Kabat delineation; and Paratome analysis tool, available at the World Wide Web at ofranlab.org/paratome/. Determination of CDR regions using these and other tools is well within the skill of the art. The identified CDRs are listed in Table 1.

Example 10

Characterization of Centrin-1 Binding Antibodies

Further characterization of the binding between antibodies produced by the clones listed in Tables 4 and 5 and Centrin-1, and peptides thereof, will be performed using methods known in the art, such as, for example, enzyme-linked immunosorbent assay (ELISA), Octet and Biacore methods. ELISA is described in Weis-Garcia, F. and Carnahan, R. H., 2017, Cold Spring Harb Protoc; doi:10.1101/pdb.top093823, which is incorporated herein as a reference in its entirety. The Octet method is described in detail in Abdiche, Y., et al., 2008, *Anal Biochem,* 377, 209-17; Abdiche, Y. N., et al., 2008, *Protein Sci,* 17, 1326-35; and Concepcion, J., et al., 2009, *Comb Chem High Throughput Screen,* 12, 791-800, each of which is incorporated herein as a reference in its entirety. The Biacore method is described in detail in Drake, A. W., et al., 2004, *Anal Biochem,* 328, 35-43; Katsamba, P. S., et al., 2006, *Anal Biochem,* 352, 208-21 and Li, B., et al., 2008 *Anal Biochem,* 377, 195-201, each of which is incorporated herein as a reference in its entirety. In particular, characterization of the binding between antibodies produced by the clones 69-11, 76-6 and 123-13 and Centrin-1, and peptides thereof, will be performed to determine binding affinity, on/off rates and epitope mapping. Exemplary Centrin-1 peptides which may be used for the binding studies are listed in Table 3.

What is claimed is:

1. An antibody comprising a heavy chain variable region (VH) and a light chain variable region (VL), wherein:
   (a) the VH comprises a CDR1 comprising the amino acid sequence set forth in SEQ ID NO: 2 or SEQ ID NO: 40, a CDR2 comprising the amino acid sequence set forth in SEQ ID NO: 3 or SEQ ID NO: 41, and a CDR3 comprising the amino acid sequence set forth in SEQ ID NO: 4 or SEQ ID NO: 42; and the VL comprises a CDR1 comprising the amino acid sequence set forth in SEQ ID NO: 10, or SEQ ID NO: 46 or SEQ ID NO: 47, a CDR2 comprising the amino acid sequence set forth in SEQ ID NO: 11 or SEQ ID NO: 48, and a CDR3 comprising the amino acid sequence set forth in SEQ ID NO: 12 or SEQ ID NO: 49;
   (b) the VH comprises a CDR1 comprising the amino acid sequence set forth in SEQ ID NO: 2 or SEQ ID NO: 40, a CDR2 comprising the amino acid sequence set forth in SEQ ID NO: 3 or SEQ ID NO: 41, and a CDR3 comprising the amino acid sequence set forth in SEQ ID NO: 4 or SEQ ID NO: 42; and the VL comprises a CDR1 comprising the amino acid sequence set forth in SEQ ID NO: 14, SEQ ID NO: 50 or SEQ ID NO: 51; a CDR2 comprising the amino acid sequence set forth in SEQ ID NO: 15 or SEQ ID NO: 52; and a CDR3 comprising the amino acid sequence set forth in SEQ ID NO: 16 or SEQ ID NO: 53;
   (c) the VH comprises a CDR1 comprising the amino acid sequence set forth in SEQ ID NO: 2 or SEQ ID NO: 40, a CDR2 comprising the amino acid sequence set forth in SEQ ID NO: 3 or SEQ ID NO: 41, and a CDR3 comprising the amino acid sequence set forth in SEQ ID NO: 4 or SEQ ID NO: 42; and the VL comprises a CDR1 comprising the amino acid sequence set forth in SEQ ID NO: 18 or SEQ ID NO: 54, a CDR2 comprising the amino acid sequence set forth in SEQ ID NO: 19 or SEQ ID NO: 55, and a CDR3 comprising the amino acid sequence set forth in SEQ ID NO: 20 or SEQ ID NO: 56;
   (d) the VH comprises a CDR1 comprising the amino acid sequence set forth in SEQ ID NO: 6 or SEQ ID NO: 43, a CDR2 comprising the amino acid sequence set forth in SEQ ID NO: 7 or SEQ ID NO: 44, and a CDR3 comprising the amino acid sequence set forth in SEQ ID NO: 8 or SEQ ID NO: 45; and the VL comprises a CDR1 comprising the amino acid sequence set forth in SEQ ID NO: 10, or SEQ ID NO: 46 or SEQ ID NO: 47, a CDR2 comprising the amino acid sequence set forth in SEQ ID NO: 11 or SEQ ID NO: 48, and a CDR3 comprising the amino acid sequence set forth in SEQ ID NO: 12 or SEQ ID NO: 49;
(e) the VH comprises a CDR1 comprising the amino acid sequence set forth in SEQ ID NO: 6 or SEQ ID NO: 43, a CDR2 comprising the amino acid sequence set forth in SEQ ID NO: 7 or SEQ ID NO: 44, and a CDR3 comprising the amino acid sequence set forth in SEQ ID NO: 8 or SEQ ID NO: 45; and the VL comprises a CDR1 comprising the amino acid sequence set forth in SEQ ID NO: 14, SEQ ID NO: 50 or SEQ ID NO: 51; a CDR2 comprising the amino acid sequence set forth in SEQ ID NO: 15 or SEQ ID NO: 52; and a CDR3 comprising the amino acid sequence set forth in SEQ ID NO: 16 or SEQ ID NO: 53; or
(f) the VH comprises a CDR1 comprising the amino acid sequence set forth in SEQ ID NO: 6 or SEQ ID NO: 43, a CDR2 comprising the amino acid sequence set forth in SEQ ID NO: 7 or SEQ ID NO: 44, and a CDR3 comprising the amino acid sequence set forth in SEQ ID NO: 8 or SEQ ID NO: 45; and the VL comprises a CDR1 comprising the amino acid sequence set forth in SEQ ID NO: 18 or SEQ ID NO: 54, a CDR2 comprising the amino acid sequence set forth in SEQ ID NO: 19 or SEQ ID NO: 55, and a CDR3 comprising the amino acid sequence set forth in SEQ ID NO: 20 or SEQ ID NO: 56.

2. The antibody of claim 1, wherein the antibody comprises:
(a) a VH comprising the amino acid sequence of SEQ ID NO: 1; and a VL comprising the amino acid sequence of SEQ ID NO: 9;
(b) a VH comprising the amino acid sequence of SEQ ID NO: 5; and a VL comprising the amino acid sequence of SEQ ID NO: 9;
(c) a VH comprising the amino acid sequence of SEQ ID NO: 1; and a VL comprising the amino acid sequence of SEQ ID NO: 13;
(d) a VH comprising the amino acid sequence of SEQ ID NO: 5; and a VL comprising the amino acid sequence of SEQ ID NO: 13;
(e) a VH comprising the amino acid sequence of SEQ ID NO: 1; and a VL comprising the amino acid sequence of SEQ ID NO: 17; or
(f) a VH comprising the amino acid sequence of SEQ ID NO: 5; and a VL comprising the amino acid sequence of SEQ ID NO:17.

3. The antibody of claim 1, wherein the antibody is an antigen-binding fragment thereof.

4. The antibody of claim 1, wherein the antibody is a full-length antibody.

5. The antibody of claim 1, wherein the antibody is conjugated to a radionuclide.

6. The antibody of claim 5, wherein the radionuclide is an α-emitting or a β-emitting radioisotope.

7. The antibody of claim 5, wherein the radionuclide comprises 213-Bismuth, 177-Lutetium, 212-Lead, 225 Actinium, 227-Thorium, 186-Rhenium, or 188-Rhenium.

8. The antibody of claim 1, wherein the antibody is conjugated to a cytotoxin.

9. The antibody of claim 1, wherein the antibody is bispecific, wherein the antibody comprises a first specificity to Centrin-1 and a second specificity to an immune checkpoint inhibitor.

10. The antibody of claim 1, wherein the antibody is humanized.

11. A pharmaceutical composition comprising the antibody of claim 1 and a pharmaceutically acceptable excipient.

12. A method of treating pancreatic cancer or prostate cancer in a subject in need thereof, comprising administering to the subject in need thereof a therapeutically effective amount of the antibody of claim 1.

13. The method of claim 12, wherein the cancer is pancreatic cancer.

14. The method of claim 13, wherein the pancreatic cancer is pancreatic ductal adenocarcinoma (PDAC).

15. The method of claim 12, wherein the cancer is prostate cancer.

16. The method of claim 15, wherein the prostate cancer is adenocarcinoma of the prostate.

17. The method of claim 12, wherein the administration is systemic, regional, local, or intracavity administration.

18. A method of determining that a subject has, or is at risk for developing pancreatic cancer or prostate cancer comprising contacting a biological sample from the subject with the antibody of claim 1, and determining that the subject has, or is at risk for developing, pancreatic cancer or prostate cancer if the relative level of Centrin-1 is higher than a control value.

19. The method of claim 18, comprising administering a treatment to the subject.

20. A nucleic acid molecule encoding the antibody of claim 1.

* * * * *

SEQUENCE LISTING

<160> NUMBER OF SEQ ID NOS: 59

<210> SEQ ID NO 1
<211> LENGTH: 113
<212> TYPE: PRT
<213> ORGANISM: Mus musculus

<400> SEQUENCE: 1

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Val Phe Ser Arg Tyr
            20                  25                  30

Trp Met Asn Trp Val Lys Gln Arg Pro Gly Gln Gly Leu Glu Trp Ile
        35                  40                  45

Gly Gln Ile Tyr Pro Gly Asp Gly Asp Thr Asp Tyr Asn Gly Glu Phe
    50                  55                  60

Lys Gly Lys Ala Thr Leu Thr Ala Asp Arg Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Glu Phe Ala Tyr Trp Gly Gln Gly Thr Leu Val Thr Val Ser
            100                 105                 110

Ala

<210> SEQ ID NO 2
<211> LENGTH: 9
<212> TYPE: PRT
<213> ORGANISM: Mus musculus

<400> SEQUENCE: 2

Tyr Val Phe Ser Arg Tyr Trp Met Asn
1               5

<210> SEQ ID NO 3
<211> LENGTH: 14
<212> TYPE: PRT
<213> ORGANISM: Mus musculus

<400> SEQUENCE: 3

Trp Ile Gly Gln Ile Tyr Pro Gly Asp Gly Asp Thr Asp Tyr
1               5                   10

<210> SEQ ID NO 4
<211> LENGTH: 5
<212> TYPE: PRT
<213> ORGANISM: Mus musculus

<400> SEQUENCE: 4

Arg Glu Phe Ala Tyr
1               5

<210> SEQ ID NO 5
<211> LENGTH: 120
<212> TYPE: PRT
<213> ORGANISM: Mus musculus

<400> SEQUENCE: 5

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

```
Tyr Met Ser Trp Val Arg Gln Pro Pro Gly Lys Ala Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Ala Glu Asp Ser Ala Thr Tyr
                85                  90                  95

Tyr Cys Ala Arg Ala Gly Asn Tyr Gly Gly Phe Asp Val Trp Gly Ala
            100                 105                 110

Gly Thr Thr Val Thr Val Ser Ser
            115                 120

<210> SEQ ID NO 6
<211> LENGTH: 9
<212> TYPE: PRT
<213> ORGANISM: Mus musculus

<400> SEQUENCE: 6

Phe Thr Phe Thr Asp Tyr Tyr Met Ser
1               5

<210> SEQ ID NO 7
<211> LENGTH: 18
<212> TYPE: PRT
<213> ORGANISM: Mus musculus

<400> SEQUENCE: 7

Trp Leu Gly Phe Ile Arg Asn Lys Ala Asn Gly Tyr Thr Thr Glu Tyr
1               5                   10                  15

Ser Ala

<210> SEQ ID NO 8
<211> LENGTH: 11
<212> TYPE: PRT
<213> ORGANISM: Mus musculus

<400> SEQUENCE: 8

Ala Arg Ala Gly Asn Tyr Gly Gly Phe Asp Val
1               5                   10

<210> SEQ ID NO 9
<211> LENGTH: 107
<212> TYPE: PRT
<213> ORGANISM: Mus musculus

<400> SEQUENCE: 9

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Tyr
                85                  90                  95
```

```
Thr Phe Gly Gly Gly Thr Lys Leu Glu Ile Lys
            100                 105
```

```
<210> SEQ ID NO 10
<211> LENGTH: 9
<212> TYPE: PRT
<213> ORGANISM: Mus musculus

<400> SEQUENCE: 10

Ser Gln Asp Val Gly Thr Ala Val Ala
1               5
```

```
<210> SEQ ID NO 11
<211> LENGTH: 11
<212> TYPE: PRT
<213> ORGANISM: Mus musculus

<400> SEQUENCE: 11

Leu Leu Ile Tyr Trp Ala Ser Thr Arg His Thr
1               5                   10
```

```
<210> SEQ ID NO 12
<211> LENGTH: 8
<212> TYPE: PRT
<213> ORGANISM: Mus musculus

<400> SEQUENCE: 12

Gln Gln Tyr Ser Ser Tyr Pro Tyr
1               5
```

```
<210> SEQ ID NO 13
<211> LENGTH: 107
<212> TYPE: PRT
<213> ORGANISM: Mus musculus

<400> SEQUENCE: 13

Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Asn Ser Pro Phe
                85                  90                  95

Thr Phe Gly Gly Gly Thr Lys Leu Glu Ile Lys
            100                 105
```

```
<210> SEQ ID NO 14
<211> LENGTH: 9
<212> TYPE: PRT
<213> ORGANISM: Mus musculus

<400> SEQUENCE: 14

Ser Gln Ser Val Ser Asn Asp Val Ala
1               5
```

```
<210> SEQ ID NO 15
```

<210> SEQ ID NO 16
<211> LENGTH: 11
<212> TYPE: PRT
<213> ORGANISM: Mus musculus

<400> SEQUENCE: 15

Leu Leu Ile Tyr Tyr Ala Ser Asn Arg Tyr Thr
1               5                   10

<210> SEQ ID NO 16
<211> LENGTH: 8
<212> TYPE: PRT
<213> ORGANISM: Mus musculus

<400> SEQUENCE: 16

Gln Gln Asp Tyr Asn Ser Pro Phe
1               5

<210> SEQ ID NO 17
<211> LENGTH: 106
<212> TYPE: PRT
<213> ORGANISM: Mus musculus

<400> SEQUENCE: 17

Asp Ile Gln Met Thr Gln Ser Pro Ser Ser Leu Ser Ile Phe Leu Gly
1               5                   10                  15

Gly Lys Val Thr Ile Thr Cys Lys Ala Ser Gln Asp Ile Asn Lys His
            20                  25                  30

Ile Ala Trp Tyr Gln His Arg Pro Gly Lys Ser Pro Trp Leu Leu Ile
        35                  40                  45

His Tyr Thr Ser Thr Leu Gln Pro Gly Ile Pro Ser Arg Phe Ser Gly
    50                  55                  60

Ser Gly Ser Gly Arg Asp Tyr Ser Leu Ser Ile Ile Asn Leu Glu Pro
65                  70                  75                  80

Glu Asp Phe Ala Thr Tyr Tyr Cys Leu Gln Tyr Asp Asn Leu Trp Thr
                85                  90                  95

Phe Gly Gly Gly Thr Lys Leu Glu Ile Lys
            100                 105

<210> SEQ ID NO 18
<211> LENGTH: 8
<212> TYPE: PRT
<213> ORGANISM: Mus musculus

<400> SEQUENCE: 18

Gln Asp Ile Asn Lys His Ile Ala
1               5

<210> SEQ ID NO 19
<211> LENGTH: 12
<212> TYPE: PRT
<213> ORGANISM: Mus musculus

<400> SEQUENCE: 19

Trp Leu Leu Ile His Tyr Thr Ser Thr Leu Gln Pro
1               5                   10

<210> SEQ ID NO 20
<211> LENGTH: 7
<212> TYPE: PRT
<213> ORGANISM: Mus musculus

<400> SEQUENCE: 20

Leu Gln Tyr Asp Asn Leu Trp
1               5

<210> SEQ ID NO 21
<211> LENGTH: 15
<212> TYPE: PRT
<213> ORGANISM: Homo sapiens

<400> SEQUENCE: 21

Lys Pro Ser Ala Ala Ser Thr Gly Gln Lys Arg Lys Val Ala Pro
1               5                   10                  15

<210> SEQ ID NO 22
<211> LENGTH: 14
<212> TYPE: PRT
<213> ORGANISM: Homo sapiens

<400> SEQUENCE: 22

Lys Pro Ser Ala Ala Ser Thr Gly Gln Lys Arg Lys Val Ala
1               5                   10

<210> SEQ ID NO 23
<211> LENGTH: 13
<212> TYPE: PRT
<213> ORGANISM: Homo sapiens

<400> SEQUENCE: 23

Lys Pro Ser Ala Ala Ser Thr Gly Gln Lys Arg Lys Val
1               5                   10

<210> SEQ ID NO 24
<211> LENGTH: 12
<212> TYPE: PRT
<213> ORGANISM: Homo sapiens

<400> SEQUENCE: 24

Lys Pro Ser Ala Ala Ser Thr Gly Gln Lys Arg Lys
1               5                   10

<210> SEQ ID NO 25
<211> LENGTH: 11
<212> TYPE: PRT
<213> ORGANISM: Homo sapiens

<400> SEQUENCE: 25

Lys Pro Ser Ala Ala Ser Thr Gly Gln Lys Arg
1               5                   10

<210> SEQ ID NO 26
<211> LENGTH: 10
<212> TYPE: PRT
<213> ORGANISM: Homo sapiens

<400> SEQUENCE: 26

Lys Pro Ser Ala Ala Ser Thr Gly Gln Lys
1               5                   10

<210> SEQ ID NO 27
<211> LENGTH: 9
<212> TYPE: PRT
<213> ORGANISM: Homo sapiens

<400> SEQUENCE: 27

Lys Pro Ser Ala Ala Ser Thr Gly Gln
1               5

<210> SEQ ID NO 28
<211> LENGTH: 8
<212> TYPE: PRT
<213> ORGANISM: Homo sapiens

<400> SEQUENCE: 28

Lys Pro Ser Ala Ala Ser Thr Gly
1               5

<210> SEQ ID NO 29
<211> LENGTH: 7
<212> TYPE: PRT
<213> ORGANISM: Homo sapiens

<400> SEQUENCE: 29

Lys Pro Ser Ala Ala Ser Thr
1               5

<210> SEQ ID NO 30
<211> LENGTH: 6
<212> TYPE: PRT
<213> ORGANISM: Homo sapiens

<400> SEQUENCE: 30

Lys Pro Ser Ala Ala Ser
1               5

<210> SEQ ID NO 31
<211> LENGTH: 14
<212> TYPE: PRT
<213> ORGANISM: Homo sapiens

<400> SEQUENCE: 31

Pro Ser Ala Ala Ser Thr Gly Gln Lys Arg Lys Val Ala Pro
1               5                   10

<210> SEQ ID NO 32
<211> LENGTH: 13
<212> TYPE: PRT
<213> ORGANISM: Homo sapiens

<400> SEQUENCE: 32

Ser Ala Ala Ser Thr Gly Gln Lys Arg Lys Val Ala Pro
1               5                   10

<210> SEQ ID NO 33
<211> LENGTH: 12
<212> TYPE: PRT
<213> ORGANISM: Homo sapiens

<400> SEQUENCE: 33

Ala Ala Ser Thr Gly Gln Lys Arg Lys Val Ala Pro
1               5                   10

<210> SEQ ID NO 34
<211> LENGTH: 11
<212> TYPE: PRT
<213> ORGANISM: Homo sapiens

<400> SEQUENCE: 34

Ala Ser Thr Gly Gln Lys Arg Lys Val Ala Pro
1               5                   10

```
<210> SEQ ID NO 35
<211> LENGTH: 10
<212> TYPE: PRT
<213> ORGANISM: Homo sapiens

<400> SEQUENCE: 35

Ser Thr Gly Gln Lys Arg Lys Val Ala Pro
1               5                   10

<210> SEQ ID NO 36
<211> LENGTH: 9
<212> TYPE: PRT
<213> ORGANISM: Homo sapiens

<400> SEQUENCE: 36

Thr Gly Gln Lys Arg Lys Val Ala Pro
1               5

<210> SEQ ID NO 37
<211> LENGTH: 8
<212> TYPE: PRT
<213> ORGANISM: Homo sapiens

<400> SEQUENCE: 37

Gly Gln Lys Arg Lys Val Ala Pro
1               5

<210> SEQ ID NO 38
<211> LENGTH: 7
<212> TYPE: PRT
<213> ORGANISM: Homo sapiens

<400> SEQUENCE: 38

Gln Lys Arg Lys Val Ala Pro
1               5

<210> SEQ ID NO 39
<211> LENGTH: 6
<212> TYPE: PRT
<213> ORGANISM: Homo sapiens

<400> SEQUENCE: 39

Lys Arg Lys Val Ala Pro
1               5

<210> SEQ ID NO 40
<211> LENGTH: 5
<212> TYPE: PRT
<213> ORGANISM: Mus musculus

<400> SEQUENCE: 40

Arg Tyr Trp Met Asn
1               5

<210> SEQ ID NO 41
<211> LENGTH: 16
<212> TYPE: PRT
<213> ORGANISM: Mus musculus

<400> SEQUENCE: 41

Ile Tyr Pro Gly Asp Gly Asp Thr Asp Tyr Asn Gly Glu Phe Lys Gly
1               5                   10                  15

<210> SEQ ID NO 42
<211> LENGTH: 4
```

```
<212> TYPE: PRT
<213> ORGANISM: Mus musculus

<400> SEQUENCE: 42

Glu Phe Ala Tyr
1

<210> SEQ ID NO 43
<211> LENGTH: 5
<212> TYPE: PRT
<213> ORGANISM: Mus musculus

<400> SEQUENCE: 43

Asp Tyr Tyr Met Ser
1               5

<210> SEQ ID NO 44
<211> LENGTH: 19
<212> TYPE: PRT
<213> ORGANISM: Mus musculus

<400> SEQUENCE: 44

Phe Ile Arg Asn Lys Ala Asn Gly Tyr Thr Thr Glu Tyr Ser Ala Ser
1               5                   10                  15

Val Lys Gly

<210> SEQ ID NO 45
<211> LENGTH: 9
<212> TYPE: PRT
<213> ORGANISM: Mus musculus

<400> SEQUENCE: 45

Ala Gly Asn Tyr Gly Gly Phe Asp Val
1               5

<210> SEQ ID NO 46
<211> LENGTH: 8
<212> TYPE: PRT
<213> ORGANISM: Mus musculus

<400> SEQUENCE: 46

Gln Asp Val Gly Thr Ala Val Ala
1               5

<210> SEQ ID NO 47
<211> LENGTH: 11
<212> TYPE: PRT
<213> ORGANISM: Mus musculus

<400> SEQUENCE: 47

Lys Ala Ser Gln Asp Val Gly Thr Ala Val Ala
1               5                   10

<210> SEQ ID NO 48
<211> LENGTH: 7
<212> TYPE: PRT
<213> ORGANISM: Mus musculus

<400> SEQUENCE: 48

Trp Ala Ser Thr Arg His Thr
1               5

<210> SEQ ID NO 49
<211> LENGTH: 9
```

-continued

```
<212> TYPE: PRT
<213> ORGANISM: Mus musculus

<400> SEQUENCE: 49

Gln Gln Tyr Ser Ser Tyr Pro Tyr Thr
1               5

<210> SEQ ID NO 50
<211> LENGTH: 8
<212> TYPE: PRT
<213> ORGANISM: Mus musculus

<400> SEQUENCE: 50

Gln Ser Val Ser Asn Asp Val Ala
1               5

<210> SEQ ID NO 51
<211> LENGTH: 11
<212> TYPE: PRT
<213> ORGANISM: Mus musculus

<400> SEQUENCE: 51

Lys Ala Ser Gln Ser Val Ser Asn Asp Val Ala
1               5                   10

<210> SEQ ID NO 52
<211> LENGTH: 7
<212> TYPE: PRT
<213> ORGANISM: Mus musculus

<400> SEQUENCE: 52

Tyr Ala Ser Asn Arg Tyr Thr
1               5

<210> SEQ ID NO 53
<211> LENGTH: 9
<212> TYPE: PRT
<213> ORGANISM: Mus musculus

<400> SEQUENCE: 53

Gln Gln Asp Tyr Asn Ser Pro Phe Thr
1               5

<210> SEQ ID NO 54
<211> LENGTH: 11
<212> TYPE: PRT
<213> ORGANISM: Mus musculus

<400> SEQUENCE: 54

Lys Ala Ser Gln Asp Ile Asn Lys His Ile Ala
1               5                   10

<210> SEQ ID NO 55
<211> LENGTH: 6
<212> TYPE: PRT
<213> ORGANISM: Mus musculus

<400> SEQUENCE: 55

Thr Ser Thr Leu Gln Pro
1               5

<210> SEQ ID NO 56
<211> LENGTH: 8
<212> TYPE: PRT
<213> ORGANISM: Mus musculus
```

<400> SEQUENCE: 56

Leu Gln Tyr Asp Asn Leu Trp Thr
1               5

<210> SEQ ID NO 57
<211> LENGTH: 172
<212> TYPE: PRT
<213> ORGANISM: Homo sapiens

<400> SEQUENCE: 57

Met Ala Ser Gly Phe Lys Lys Pro Ser Ala Ser Thr Gly Gln Lys
1               5                   10                  15

Arg Lys Val Ala Pro Lys Pro Glu Leu Thr Glu Asp Gln Lys Gln Glu
                20                  25                  30

Val Arg Glu Ala Phe Asp Leu Phe Asp Val Asp Gly Ser Gly Thr Ile
            35                  40                  45

Asp Ala Lys Glu Leu Lys Val Ala Met Arg Ala Leu Gly Phe Glu Pro
        50                  55                  60

Arg Lys Glu Glu Met Lys Lys Met Ile Ser Glu Val Asp Arg Glu Gly
65                  70                  75                  80

Thr Gly Lys Ile Ser Phe Asn Asp Phe Leu Ala Val Met Thr Gln Lys
                85                  90                  95

Met Ser Glu Lys Asp Thr Lys Glu Glu Ile Leu Lys Ala Phe Arg Leu
            100                 105                 110

Phe Asp Asp Asp Glu Thr Gly Lys Ile Ser Phe Lys Asn Leu Lys Arg
        115                 120                 125

Val Ala Asn Glu Leu Gly Glu Asn Leu Thr Asp Glu Glu Leu Gln Glu
    130                 135                 140

Met Ile Asp Glu Ala Asp Arg Asp Gly Asp Gly Glu Val Asn Glu Glu
145                 150                 155                 160

Glu Phe Leu Arg Ile Met Lys Lys Thr Ser Leu Tyr
                165                 170

<210> SEQ ID NO 58
<211> LENGTH: 172
<212> TYPE: PRT
<213> ORGANISM: Mus musculus

<400> SEQUENCE: 58

Met Ala Ser Thr Phe Arg Lys Ser Asn Val Ala Ser Thr Ser Tyr Lys
1               5                   10                  15

Arg Lys Val Gly Pro Lys Pro Glu Leu Thr Glu Asp Gln Lys Gln Glu
                20                  25                  30

Val Arg Glu Ala Phe Asp Leu Phe Asp Ser Asp Gly Ser Gly Thr Ile
            35                  40                  45

Asp Val Lys Glu Leu Lys Val Ala Met Arg Ala Leu Gly Phe Glu Pro
        50                  55                  60

Arg Lys Glu Glu Met Lys Lys Met Ile Ser Glu Val Asp Lys Glu Ala
65                  70                  75                  80

Thr Gly Lys Ile Ser Phe Asn Asp Phe Leu Ala Val Met Thr Gln Lys
                85                  90                  95

Met Ala Glu Lys Asp Thr Lys Glu Glu Ile Leu Lys Ala Phe Arg Leu
            100                 105                 110

Phe Asp Asp Asp Glu Thr Gly Lys Ile Ser Phe Lys Asn Leu Lys Arg
        115                 120                 125

```
Val Ala Asn Glu Leu Gly Glu Ser Leu Thr Asp Glu Leu Gln Glu
    130             135             140
Met Ile Asp Glu Ala Asp Arg Asp Gly Asp Gly Glu Val Asn Glu Glu
145             150             155             160
Glu Phe Leu Lys Ile Met Lys Lys Thr Asn Leu Tyr
                165             170

<210> SEQ ID NO 59
<211> LENGTH: 172
<212> TYPE: PRT
<213> ORGANISM: Homo sapiens

<400> SEQUENCE: 59

Met Ala Ser Asn Phe Lys Lys Ala Asn Met Ala Ser Ser Ser Gln Arg
1               5                   10                  15

Lys Arg Met Ser Pro Lys Pro Glu Leu Thr Glu Glu Gln Lys Gln Glu
                20                  25                  30

Ile Arg Glu Ala Phe Asp Leu Phe Asp Ala Asp Gly Thr Gly Thr Ile
            35                  40                  45

Asp Val Lys Glu Leu Lys Val Ala Met Arg Ala Leu Gly Phe Glu Pro
    50                  55                  60

Lys Lys Glu Glu Ile Lys Lys Met Ile Ser Glu Ile Asp Lys Glu Gly
65                  70                  75                  80

Thr Gly Lys Met Asn Phe Gly Asp Phe Leu Thr Val Met Thr Gln Lys
                85                  90                  95

Met Ser Glu Lys Asp Thr Lys Glu Glu Ile Leu Lys Ala Phe Lys Leu
                100                 105                 110

Phe Asp Asp Asp Glu Thr Gly Lys Ile Ser Phe Lys Asn Leu Lys Arg
            115                 120                 125

Val Ala Lys Glu Leu Gly Glu Asn Leu Thr Asp Glu Glu Leu Gln Glu
    130                 135                 140

Met Ile Asp Glu Ala Asp Arg Asp Gly Asp Gly Glu Val Ser Glu Gln
145                 150                 155                 160

Glu Phe Leu Arg Ile Met Lys Lys Thr Ser Leu Tyr
                165                 170
```